United States Patent
Aung-Din

(10) Patent No.: US 10,632,064 B2
(45) Date of Patent: *Apr. 28, 2020

(54) TOPICAL REGIONAL NEURO AFFECTIVE THERAPY WITH CANNABINOID COMBINATION PRODUCTS

(71) Applicant: Afgin Pharma, LLC, Sarasota, FL (US)

(72) Inventor: Ronald Aung-Din, Sarasota, FL (US)

(73) Assignee: Afgin Pharma, LLC, Sarasota, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/506,363

(22) Filed: Jul. 9, 2019

(65) Prior Publication Data
US 2019/0343760 A1 Nov. 14, 2019

Related U.S. Application Data

(63) Continuation of application No. 16/192,219, filed on Nov. 15, 2018, now Pat. No. 10,383,816, which is a continuation of application No. 15/228,690, filed on Aug. 4, 2016, now abandoned, which is a continuation-in-part of application No. 15/058,946, filed on Mar. 2, 2016.

(60) Provisional application No. 62/299,260, filed on Feb. 24, 2016, provisional application No. 62/126,757, filed on Mar. 2, 2015.

(51) Int. Cl.
| | |
|---|---|
| *A61K 9/00* | (2006.01) |
| *A61K 31/473* | (2006.01) |
| *A61K 31/381* | (2006.01) |
| *A61K 31/34* | (2006.01) |
| *A61K 36/185* | (2006.01) |
| *C07D 487/04* | (2006.01) |

(52) U.S. Cl.
CPC ............ *A61K 9/0014* (2013.01); *A61K 31/34* (2013.01); *A61K 31/381* (2013.01); *A61K 31/473* (2013.01); *A61K 36/185* (2013.01); *C07D 487/04* (2013.01)

(58) Field of Classification Search
None
See application file for complete search history.

(56) References Cited

U.S. PATENT DOCUMENTS

| | | | |
|---|---|---|---|
| 3,598,122 A | 8/1971 | Zaffaroni | |
| 3,797,494 A | 3/1974 | Zaffaroni | |
| 4,144,317 A | 3/1979 | Higuchi et al. | |
| 4,201,211 A | 5/1980 | Chandrasekaran et al. | |
| 4,262,003 A | 4/1981 | Urquhart et al. | |
| 4,379,454 A | 4/1983 | Campbell et al. | |
| 4,511,563 A | 4/1985 | Schmolka | |
| 4,588,580 A | 5/1986 | Gale et al. | |
| 4,767,619 A | 8/1988 | Murray | |
| 4,806,341 A | 2/1989 | Chien et al. | |
| 4,816,470 A | 3/1989 | Dowie et al. | |
| 4,820,720 A | 4/1989 | Sanders et al. | |
| 4,861,760 A | 8/1989 | Mazuel et al. | |
| 4,883,660 A | 11/1989 | Blackman et al. | |
| 4,916,132 A | 4/1990 | Seibel | |
| 5,016,652 A | 5/1991 | Rose et al. | |
| 5,026,556 A | 6/1991 | Drust et al. | |
| 5,037,845 A | 8/1991 | Oxford | |
| 5,053,227 A | 10/1991 | Chiang et al. | |
| 5,069,909 A | 12/1991 | Sharma et al. | |
| 5,307,953 A | 5/1994 | Regan | |
| 5,318,780 A | 6/1994 | Viegas et al. | |
| 5,364,628 A | 11/1994 | Kissel et al. | |
| 5,466,699 A | 11/1995 | Robertson et al. | |
| 5,521,196 A | 5/1996 | Audia et al. | |
| 5,545,644 A | 8/1996 | MacOr et al. | |
| 5,554,639 A | 9/1996 | Craig et al. | |
| 5,562,917 A | 10/1996 | Durif et al. | |
| 5,698,571 A | 12/1997 | Audia et al. | |
| 5,705,520 A | 1/1998 | Craig et al. | |
| 5,719,197 A | 2/1998 | Kanios et al. | |
| 5,807,571 A | 9/1998 | List | |
| 5,814,653 A | 9/1998 | Flaugh et al. | |
| 5,827,571 A | 9/1998 | Harald | |
| 5,837,289 A | 11/1998 | Gasela et al. | |

(Continued)

FOREIGN PATENT DOCUMENTS

| | | |
|---|---|---|
| EP | 0303507 | 2/1989 |
| EP | 0636623 | 2/1995 |

(Continued)

OTHER PUBLICATIONS

Chepyala et al. "Treatment of Cyclic Vomiting Syndrome, Current Treatment OpTions in Gastroenterology" 2007, 10 abstract.
Remington's Pharmaceutical Sciences, 15th Edition, 1975, Mack Publishing Co. p. 1529.
Aung-Din et al "Transdermal sumatriptane effectiveness and convenience in migraineurs" Blackwell Science Ltd. Cephalagia, 2001, vol. 21; p. 412.
Bartsch and Goadsby, "Increased responses in trigeminocervical nociceptive neurons to cervical input after simulation of the dura mater" Brain, vol. 126, No. 8, oo. 1801-1813 (Aug. 2003).

(Continued)

*Primary Examiner* — Nannette Holloman
(74) *Attorney, Agent, or Firm* — Davidson, Davidson & Kappel, LLC

(57) ABSTRACT

A method of treating a disease state or condition in humans via topical brainstem afferent stimulation therapy via the administration of a cannabinoid drug(s) and a second therapeutically active agent(s) to the back of the neck of a human patient to provide regional neuro-affective therapy is disclosed. In certain preferred embodiments, the cannabinoid drug(s) are not psychoactive or substantially not psychoactive. In certain embodiments, the drugs are incorporated into a pharmaceutically acceptable topical carrier, e.g., a cream. In certain preferred embodiments, the cannabinoid drug(s) comprises cannabidiol.

19 Claims, 11 Drawing Sheets

(56) References Cited

U.S. PATENT DOCUMENTS

| | | |
|---|---|---|
| 5,855,907 A | 1/1999 | Peyman |
| 5,863,559 A | 1/1999 | Phillips et al. |
| 5,863,935 A | 1/1999 | Robertson et al. |
| 5,872,145 A | 2/1999 | Plachetka |
| 6,020,001 A | 2/2000 | Phillips et al. |
| 6,060,499 A | 5/2000 | Plachetka |
| 6,103,266 A | 8/2000 | Tapolsky et al. |
| 6,197,331 B1 | 3/2001 | Lerner |
| 6,203,796 B1 | 3/2001 | Papaprodromou |
| 6,221,377 B1 | 4/2001 | Meyer |
| 6,368,627 B1 | 4/2002 | Phillips et al. |
| 6,383,471 B1 | 5/2002 | Chen et al. |
| 6,384,034 B2 | 5/2002 | Simitchieva et al. |
| 6,455,557 B1 | 9/2002 | Pellegrini et al. |
| 8,329,734 B2 | 12/2012 | Aung Din |
| 8,592,424 B2 | 11/2013 | Aung Din |
| 8,883,830 B2 | 11/2014 | Aung Din |
| 9,012,480 B2 | 4/2015 | Aung Din |
| 9,044,390 B1 | 6/2015 | Speier |
| 9,345,659 B2 | 5/2016 | Hwang et al. |
| 2002/0115618 A1 | 8/2002 | Rosenbloom |
| 2002/0132827 A1 | 9/2002 | Nichols et al. |
| 2002/0165207 A1 | 11/2002 | Rosenbloom |
| 2003/0013753 A1 | 1/2003 | Aung-Din |
| 2003/0167556 A1 | 9/2003 | Kelley |
| 2004/0220205 A1 | 11/2004 | Wikstrom |
| 2006/0069059 A1 | 3/2006 | Schaller et al. |
| 2007/0065463 A1 | 3/2007 | Aung-Din |
| 2007/0275964 A1 | 8/2007 | Bartolini et al. |
| 2008/0038363 A1 | 2/2008 | Zaffaroni et al. |
| 2008/0280996 A1 | 11/2008 | Piankowski et al. |
| 2009/0247619 A1 | 10/2009 | Stinchcomb et al. |
| 2011/0052694 A1 | 3/2011 | Stinchcomb et al. |
| 2011/0178114 A1 | 7/2011 | Aung-Din |
| 2011/0178177 A1 | 7/2011 | Wolicki et al. |
| 2012/0202891 A1 | 9/2012 | Stinchcomb et al. |
| 2012/0202892 A1 | 9/2012 | Stinchcomb et al. |
| 2014/0030289 A1 | 1/2014 | Ofir et al. |
| 2014/0302148 A1 | 10/2014 | Winnicki |
| 2015/0051299 A1 | 2/2015 | Anavi-Goffer et al. |
| 2016/0106705 A1 | 4/2016 | Verzura et al. |

FOREIGN PATENT DOCUMENTS

| | | |
|---|---|---|
| EP | 0705600 | 10/1996 |
| EP | 2444081 A1 | 4/2012 |
| WO | 9118897 | 12/1991 |
| WO | 9206973 | 4/1992 |
| WO | 0500086 | 8/1992 |
| WO | 9426270 | 1/1994 |
| WO | 9505137 | 2/1995 |
| WO | 03/024456 | 3/2003 |
| WO | 03032983 | 4/2003 |
| WO | WO 03/032983 | 4/2003 |
| WO | 2004112723 | 12/2004 |
| WO | 2007128462 | 11/2007 |
| WO | 2010005507 | 1/2010 |
| WO | 2015068052 A2 | 5/2015 |
| WO | 2016014419 A1 | 1/2016 |

OTHER PUBLICATIONS

Bogduk et al. "Cervicogenic Headache: Anatomic Basis and Pathophysiologic Mechanisms" Current Pain and Headache Reports 2001, vol. 5 p. 382.

Aung-Din "Topical Delivery: Topical Regional Neuro-Affective (TRNA) Therapy: Novel Ground-Breaking Triptan Drug Delivery for Treating Migraines" Drug Delivery Technology, Sep. 2009, vol. 9, No. 8.

Pierce et al. "Zelrix: a novel transdermal formulation of sumatriptan" Headache, vol. 49, (Jun. 2009) pp. 815-817 abstract.

Patel et al. "Controlled non-invasive transdermal iontophoretic delivery of zolmitriptan hydrochloride in vitro and in vivo" Eur. J. Pharm. and Biopharm. vol. 72, (Feb. 2009) pp. 304-309; abstract.

Garg et al "Elastic liposomal formulation for sustained delivery of antimigraine drug: In vitro characterization and biological evaluation" Drug Dev. Ind. Pharm., vol. 34; Oct. 2008; pp. 1100-1110; abstract.

Messlinger, K; Hotta, H.; Pawlak, M.; Schmidt, R.F., Effects of the 5-HT1 receptor agonists, sumatriptan and CP 93,129, on dural arterial flow in the rat, Eur J Pharmacol, vol. 332 No. 2, Aug. 6, 1997 pp. 173-181.

Piovesan, et al., "Referred Pain After Painful Stimulation of the Greater Occipital Nerve in Humans: Evidence of Convergence of Cervical Afferences on Trigeminal Nuclei", Cephalalgia, 2001, 21, 107-109.

Rougier, et al. In vivo percutaneous penetration of some organic compounds related to anatomic site in humans; predictive assessment by the stripping method, J. Pharmac. Sci., vol. 76, No. 6, Jun. 1987, pp. 451-454.

Goodman & Gilman, The Pharmacological Basis of Therapeutics, Ninth Edition, (1996), Chapter 21, Peroutka, Drugs Effective in the Therapy of Migraine, pp. 487-502.

Methods Find Exp Clin Pharmacol 2002, 24(6): 371-391— Gateways to Clinical Trials—Jul.-Aug. 2002 M. Bayes, X. Rabasseda, J.R. Prous.

Schwarz, et al., Postdural Puncture Headache: Diagnosis, Prevention and Therapy Schmerz, vol. 13, No. 5, 1999—pp. 332-340; Abstract.

Aung-Din, Ronald, Transdermal Sumatriptan: A Novel Dosage Form Efficacious in the Treatment of Acute Migraine, Headache: The Journal of Head and Face Pain, vol. 45, No. 5, pp. 389-390, May 2002.

Aung-Din, Ronald, Transdermal Sumatriptan in Clinical Practice: The Experience of 42 Patients with Acute Migraine in an Outpatient Setting, Headache: The Journal of Head and Face Pain, vol. 43, No. 5, p. 523, May 2003.

Aung-Din, Ronald and Kinnard, Fred, Topical Tizanidine (Zanaflex) Gel Effective in Migraine and Tension-Type Headache, Headache: The Journal of Head and Face Pain, vol. 44, No. 5, p. 509, May 2004.

Norton, Patrice G.W., Transdermal Sumatriptan May Relieve Migraines, Internal Medicine News, vol. 36, Issue 19, p. 14, Oct. 1, 2003.

Tennant, F., "Topical Use of Morphine", Practical Pain Management, Oct. 2008, pp. 42-43.

Katzenschlager et. al., Movement Disorders, 2005, Movement Disorder Society, vol. 20, No. 2, pp. 151-157.

Merello et. al., Journal of Neurology, Neurosurgery, and Psychiatry, 1994, BMJ Publishing Group, vol. 57, pp. 1503-1509.

Trojanowski et. al., Annals of the New York Academy of Sciences, 2003, New York Academy of Sciences, vol. 991, pp. 107-110.

CAS STN abstract; Reches et. al., Advances in Neurology, 1984, vol. 40, pp. 171-179.

Cousins et. al., European Journal of Pharmacology, 1997, Elsevier, vol. 322, pp. 137-145.

Lorenzo Priano, et al. "Transdermal apomorphine permeation from microemulsions: A new treatment in Parkinson's disease" Movement Disorders, vol. 19, No. 8, pp. 937-942, Jan. 1, 2004.

Stacy M. et al. "Amomorphine for the acute treatment of "off" episodes in Parkinson's disease" Parknsonism and Related Disorders, vol. 14, No. 2, pp. 85-92, Jul. 16, 2007.

Pfeiffer R F. "Transdermal drug delivery in Parkinson's Disease" Aging Health, vol. 3, No. 4, p. 473, col. 2, paragraph 2; p. 476, col. 2, paragraph 3; p. 477, col. 2, paragraph 2. Aug. 4, 2007.

Ceballos-Baumann. "Update Parkinson's disease—Pharmacotherapy, activating therapies, deep brain stimulation" Pyschoneuro, vol. 34, No. 1. pp. 10-22. 2008.

Ronald Aung-Din. "Nuchal topical neuro-affective therapy: A novel treatment for parkinson's disease using apomorphine" Drug Delivery Technology, vol. 19, No. 8. pp. 48-55. Oct. 2010.

Vickers, James C., "A Vaccine Against Alzheimer's Disease— Developments to Date", Drugs Aging, 2002, vol. 19(7), pp. 587-494.

International Search Report from International PCT Application No. PCT/US2017/047122 dated Feb. 28, 2019.

Third Party Observation for EP application No. 16759411.8-1112 / 3265081 dated May 20, 2019.

(56) References Cited

OTHER PUBLICATIONS

International Written Opinion from International PCT Application No. PCT/US16/20446 dated May 17, 2016.

TOPICAL REGIONAL NEURO AFFECTIVE
THERAPY WITH CANNABINOID
COMBINATION PRODUCTS

This application is a continuation of U.S. patent application Ser. No. 16/192,219, filed Nov. 15, 2018, which is a continuation of U.S. patent application Ser. No. 15/228,690, filed Aug. 4, 2016, which is a continuation in part of U.S. application Ser. No. 15/058,946 filed Mar. 2, 2016, which claims the benefit of U.S. Provisional Patent Application No. 62/299,260, filed Feb. 24, 2016 and U.S. Provisional Patent Application No. 62/126,757, filed on Mar. 2, 2015, the disclosures of which are hereby incorporated by reference in their entirety.

This application claims priority to U.S. Application No. 62/126,757, filed on Mar. 2, 2015 and U.S. Application No. 62/299,260, filed on Feb. 24, 2016; the disclosures of which are hereby incorporated by reference herein.

FIELD OF THE INVENTION

The invention relates to topical regional neuro-affective therapy ("TRNA THERAPY") with cannabinoids, such as cannabidiol (CBD). This is accomplished via administration of effective amounts of these agents on the back of the neck.

BACKGROUND OF THE INVENTION

The approximate 212 pound human brain is comprised of the most complex material known to man. The neuron, the primary functional cell of the nervous system, operates on the basis of electrical impulses that result in the release of neurochemical substances (neurotransmitters) at specific receptors: dopamine, serotonin, acetylcholine, norepinephrine, gamma-amino butyric acid (GABA), and many others. There are estimated to be 80-100 billion (10 times the world population) neurons in the average human brain. These neurons, in turn, make 200-300 billion coded connections with other neurons to accomplish the complex tasks of the human body.

The brainstem serves as the vital pathway for relay and processing of neural impulses flowing continuously between the brain and the rest of the body. It is about the size of the thumb and contains the most dense and complicated wiring systems in the human body. In addition to the axons and dendrites (wires) that carry nerve impulses, the brainstem also contains critical nuclei that function as electrical generators and relays. Some of the nuclei are related to cranial nerve function while others serve as generators and impulse centers for pain perception, the autonomic system "fight or flight" response, wakefulness and alertness, as well as cardio-respiratory and related autonomic functions.

The endocannabinoid system (ECS) is involved in regulating a variety of physiological processes including appetite, pain and pleasure sensation, immune system, mood, and memory. Endocannabinoid receptors in the brain interact with cannabinoids from different sources, including (endocannabinoids (brain derived, e.g., from foods (Omega-3s and Omega-6s); phytocannabinoids (plant derived, e.g., from buds, tinctures, extracts, including tetrahydrocannabinol (THC), cannabidiol (CBD), cannabinol (CBN), etc.); and synthetic cannabinoids (such as tetrahydrocannabinol (THC)). Cannabinoids are a diverse class of chemical compounds that act on cannabinoid receptors on cells and influence neurotransmitter release in brain. These receptor proteins include endocannabinoids produced naturally in humans and animals, phytocannabinoids in *cannabis* and some other plants, and chemically manufactured synthetic cannabinoids. Phytocannabinoid A9-tetrahydrocannabinol (THC) is the primary psychoactive compound of *cannabis*. Cannabidiol (CBD) is another major constituent of the plant, and comprises up to 40% extracts of plant resin. At least 85 different cannabinoids isolated from *cannabis* exhibit varied effects.

There is no greater example of a "double-edged sword" in medical therapeutics than medical marijuana. While benefits for treating symptoms of diverse neurologic and psychiatric conditions have been known and practiced by ancient civilizations for thousands of years, marijuana's psychoactive effects have also led to abuse and labeling as a "gateway drug" for more addictive compounds. There is no class of therapeutic compounds with more controversy and stigma than cannabinoids, active components of the *cannabis* plant.

The U.S. Government has indicated there is no medical benefit for marijuana and classified it Controlled Substance Category 1, as heroin. It is considered by federal law, illegal to possess or use *cannabis* and its associated products. However, increasing number of states have challenged this position and legalized *cannabis* within their territories with varying restrictions and conditions for use. Even then, within individual states, such as in Colorado, marijuana laws vary greatly from county to county.

Although defined under U.S. federal law as having no medical use, U.S. Pat. No. 6,630,507 is held by the United States Department of Health and Human Services, covering use of cannabinoids for treating a wide range of diseases. It is directed to a method of treating diseases caused by oxidative stress comprising administering a therapeutically effective amount of a cannabinoid (e.g., cannabidiol) that has substantially no binding to the NMDA receptor to a subject who has a disease caused by oxidative stress.

SUMMARY OF THE INVENTION

It is an object of the present invention to provide a method of treatment in humans with topical afferent neural activation therapy via the regional administration of one or more cannabinoids useful for the treatment of such diseases or conditions that may be treated via such therapy.

It is an object of the present invention to provide a method for the treatment of seizures; encephalopathy, including lethargy, focus/attentional problems, and cognitive issues: spasticity; weakness; pain, including radiculopathy and neuropathy; numbness; anxiety and other mood disorders; hypertension; Parkinson's disease; insomnia; as well as any other disease or condition that may be treated with a cannabinoid.

It is an object of the present invention to provide a method for the treatment of seizures; epilepsy; encephalopathy, including lethargy, focus/attentional problems, and cognitive issues; spasticity; weakness (e.g., muscle weakness); pain, including radiculopathy and neuropathy, lower back pain, and fibromyalgia; numbness and/or tingling; anxiety and other mood disorders; hypertension and autonomic dysfunction; Parkinson's disease and tremors; insomnia; Bell's palsy and facial nerve dysfunction; glaucoma, AIDS; cancer; PTSD; trigeminal neuralgia; hemi-facial spasms; Autism/Asperger's; attention Deficit Disorder and Hyperactivity; social isolation; occipital neuralgia; TMJ dysfunction related symptoms; cognitive problems including memory disturbance; headaches (migraine and tension); peripheral neuropathy; as well as other conditions or disease states mentioned herein or any other disease or condition that may be treated with a cannabinoid.

The above objects and others are attained by virtue of the present invention, which is directed in part to a method of treating a disease state or condition in a human patient via topical regional neuro-affective (TRNA) or regional neuro-affective (RNA) therapy via administration of a drug at the back of the neck region, or the back of the neck, e.g., at the hairline (BONATH). The drug is one or more cannabinoids, along with a second therapeutically active agent, administered at the back of the neck at the hairline in close proximity to and under or on the area of skin above the brain stem to provide regional neuro-affective therapy to the human patient.

In certain preferred embodiments, the cannabinoid drug(s) is derived from an endocannabinoid, a phytocannabinoid, a synthetic cannabinoid, or mixtures of any of the foregoing. In certain preferred embodiments, the cannabinoid comprises cannabidiol.

In certain preferred embodiments, the cannabinoid drug mixture concentrate includes from about 0 to about 3% tetrahydrocannabinol, from about 0 to about 1% tetrahydrocannabinolic acid, from about 20 to about 50% cannabidiol, from about 0 to about 1% cannabidiolic acid, and from about 0 to about 1% cannabinol, for a total active cannabinoid level of from about 20% to about 50%, and the remaining cannabinoids are substantially therapeutically inactive.

In certain preferred embodiments, the cannabinoid drug(s) are incorporated into a pharmaceutically acceptable topical formulation along with a second therapeutically active agent (e.g., as described herein). In certain preferred embodiments, the cannabinoid drug(s) in the topical pharmaceutical formulation are at a concentration from about 0.75% to about 5%, by weight. In certain embodiments, the unit dose of the cannabinoid drug(s) includes from about 1 mg to about 200 mg cannabinoid drug(s) and the cannabinoid drug(s) comprise at least 80% cannabidiol. In certain preferred embodiments, a unit dose of the topical pharmaceutical formulation comprises from about 3 mg to about 50 mg cannabidiol.

In certain preferred embodiments, the pharmaceutically acceptable topical formulation comprises a topical aqueous-based carrier, with an optional penetration enhancer.

In certain preferred embodiments, the method further comprises applying a sufficient amount of the topical pharmaceutical formulation to the back of the neck region of the human patient such that the onset of a therapeutic effect occurs in less than about 30 minutes, or in less than 15 minutes. The topical pharmaceutical formulation may be administered (applied to the back of the neck region) on a once a day basis, or on a twice a day basis, a three times a day basis, or on a four times a day basis.

In certain embodiments, the patient is treated for a condition or disease state selected from the group consisting of seizures, encephalopathy, spasticity, weakness, pain, numbness, anxiety, hypertension, Parkinson's disease, multiple sclerosis, and insomnia. In other embodiments, wherein the patient is treated for a condition selected from the group consisting of lethargy, focus/attentional problems, and cognitive issues. In other embodiments, the patient is treated for a condition selected from the group consisting of radiculopathy and neuropathy. In yet other embodiments, the patient is treated for numbness, or a mood disorder.

In certain embodiments, the method further comprises further comprises topically administering at the back of the neck region (e.g., BONATH) together with, sequentially, or simultaneously but in separate formulations, an additional drug(s) selected from the group consisting of: an anti-epileptic, an anxiolytic, a neuroleptic, an anti-psychotic, an analgesic, an anti-inflammatory, an anti-Parkinson's disease/syndrome drug, a drug for the treatment of dystonia, a drug for the treatment of spastic conditions, a drug for the treatment of benign essential/familial tremor, a drug for the treatment of tremor related to MS, a drug for the treatment of chronic encepahalopathies, a drug for the treatment of congenital CNS degeneration conditions/cerebral palsy, a drug for the treatment of cerebellar degeneration syndromes, a drug for the treatment of neuropathic and/or neurogenic pain, a drug for appetite suppression, a drug for neurodegenerative conditions, a drug for the treatment of multiple sclerosis, a drug for the treatment of insomnia, a drug for the treatment of fatigue, a drug for the treatment of vertigo, nausea and/or dizziness, a drug for the treatment of writer's cramp and restless leg syndrome, other drugs which can beneficially be added to the treatment in order to provide an additive or synergistic effect with respect to treating the patient's disease state or condition; and a combination of any of the foregoing. In certain embodiments, the additional drug(s) is a dopamine agonist selected from the group consisting of apomorphine, pramipexole, ropinirole, bromocriptine, cabergoline, pergolide, rotigotine, entacapone, tocapone, seligiline, dopamine, and mixtures of any of the foregoing. In other embodiments, the disease state or condition is Parkinson's disease and/or related syndromes/diseases. In other embodiments, the additional drug(s) is selected from the group consisting of the drug is a dopamine agonist, COMT inhibitors, MAO-B inhibitors, and mixtures of any of the foregoing. In other embodiments, the additional drug(s) is an anti-epileptic drug selected from the group consisting of Valproic acid, Leviteracetem, Lamotrigene, Topiramate, Pregabalin, Gabapentin, Carbamazepine, Oxcarbazepine, Phenobarbital and other barbiturates, Tiagabine, Retigabine, Lacosamide, Perampanel, and mixtures of any of the foregoing; or the additional drug(s) is an anxiolytic, a neuroleptic and/or an antipsychotic; or the additional drug(s) is an analgesic and/or an anti-inflammatory; or the additional drug(s) is used in the treatment of neuropathic and/or neurogenic pain; or the additional drug(s) is for multiple sclerosis; or the additional drug(s) is for insomnia; or the additional drug(s) is for fatigue; or the additional drug(s) is for vertigo, nausea and/or dizziness; or the additional drug(s) is for writer's cramp and restless leg syndrome; or the additional drug(s) is a tricyclic antidepressant (TCA), a tetracyclic antidepressant, or an atypical antipsychotic.

In certain preferred embodiments, the drug is formulated in a pharmaceutically acceptable immediate release topical carrier. In certain preferred embodiments, the topical carrier is aqueous based, and may be a cream or gel.

In certain preferred embodiments, the method further comprises formulating the cannabinoid drug(s) in a pharmaceutically acceptable immediate release aqueous-based carrier. In other embodiments, the the cannabinoid drug(s) is administered in a topical pharmaceutical formulation comprising liposomes.

In certain preferred embodiments where the cannabinoid drug(s) are administered in a topical pharmaceutical formulation, the method further comprises applying a sufficient amount to the back of the neck region, e.g., BONATH of the human patient such that the onset of clinical effect occurs in less than about 30 minutes, and in certain preferred embodiments in less than about 15 minutes.

In certain preferred embodiments, the therapeutically effective amount of the cannabinoid drug(s) is applied as a unit dose comprising from about 0.25 mg to about 80 mg.

In certain preferred embodiments, the cannabinoid drug(s) is incorporated into a sustained release transdermal delivery system which is capable of delivering from about 0.25 mg to about 1000 mg of the cannabinoid drug(s) through the skin of a human patient over a 24 hour period, the transdermal delivery system being capable of delivering the cannabinoid drug(s) in such amounts for a time period from about 1 to about 7 days.

In certain embodiments, the cannabinoid drug(s) is administered via implantation or injection at the BONATH, or is administered via injection in an immediate release pharmaceutically acceptable carrier for injection. In certain embodiments, the cannabinoid drug(s) is administered via injection or implantation in a controlled release carrier to provide a prolonged effect of the cannabinoid drug(s). In certain embodiments, the cannabinoid drug(s) is administered to create a depot under the skin at the BONATH.

Certain embodiments of the invention are directed to a topical formulation, comprising a cannabinoid drug(s) in a pharmaceutically acceptable aqueous-based carrier, the cannabinoid drug(s) being incorporated into the carrier in at least one unit dose comprising from about 0.25 mg to about 80 mg cannabinoid drug(s). Preferably, when applied in a unit dose to the back of the neck of the human patient the topical formulation provides an onset of clinical effect occurs in less than about 30 minutes.

The invention is also directed to a topical formulation, comprising a cannabinoid drug in a formulation suitable for administration at the back of the neck at the hairline in close proximity to and under or on the area of skin above the brain stem of a human patient to provide regional neuro-affective therapy to the patient. The topical formulation may be prepared as an immediate, controlled or sustained release formulation.

The drug formulations useful in the present invention may be in a form selected from a topical formulation (e.g., a cream, ointment or gel); a transdermal device; or an implantable or injectable formulation.

The invention is further directed to the use of a cannabinoid drug in the preparation of a medicament for providing regional neuro-affective therapy to a human patient, wherein the drug is administered at the back of the neck at the hairline in close proximity to and under or on the area of skin above the brain stem to provide regional neuro-affective therapy to the patient.

In certain embodiments, the cannabinoid drug is applied to the posterior cervical region of the human in order to initiate the brainstem afferent stimulation therapy. Most preferably, the topical formulation or topical therapeutic system is applied to the back of the neck, preferably in close proximity to or on the area of skin above the brain stem.

In other embodiments, the cannabinoid drug is administered via implantation or injection at the back of the neck, e.g., on the back of the neck at the hairline (BONATH). In such embodiments, the therapy is accomplished via the availability of the drug(s) at the free nerve endings under the epidermis. In such embodiments, the drug may be incorporated into an implantation device or may be incorporated into a carrier such as a gel or matrix that will provide a prolonged release/effect of the cannabinoid drug(s) at the site. The carrier may be a hydrophilic or hydrophobic material, a colloidal material, and may be in a state ranging from a viscous liquid to a solid polymeric insert.

Certain embodiments of the invention are directed to a method of treatment, comprising delivering a cannabinoid drug(s) through regional neuro-affective therapy by application as a cream/gel or a sustained release patch applied at the back of the neck, or via administration under the skin at the back of the neck via an implantable or injectable drug formulation or device.

In certain embodiments, the method further provides for a therapeutically effective treatment through topical regional neuro-affective (TRNA) therapy by application of a drug(s) as a cream/gel or a sustained release patch applied at the back of the neck without the side-effects and the other draw-backs of the current injection method.

In certain preferred embodiments, the cannabinoid drug(s) is administered at the back of the neck (e.g., BONATH) in an immediate release topical formulation in a dose comprising from about 0.25 mg to about 200 mg of the cannabinoid drug(s), and in certain embodiments more preferably from about 1 to about 50 mg of the cannabinoid drug(s). In certain preferred embodiments, the cannabinoid drug(s) are in a more potent form (e.g., crystallized CBD from a herbal source), and the dose is from about 10 mg to about 20 mg. In certain other embodiments, the immediate release topical formulation includes from about 1 mg to about 10 mg cannabidiol, preferably from about 2 mg to about 6 mg cannabidiol, and most preferably about 4 mg cannabidiol.

In certain preferred embodiments, the method of treatment further comprises administering the cannabinoid drug(s) to other areas of the spine and/or peripheral nerves in addition to administration on or at the back of the neck, in order to provide an additive or synergistic effect and further modulate afferent neural input to the brain to affect efferent outflow for relief of symptoms.

In certain preferred embodiments, the method of treatment further comprises topically administering at the back of the neck together with, sequentially, or simultaneously but in separate formulations, one or more additional active agents ("drugs") which may be chosen from the following: an anti-epileptic, an anxiolytic, a neuroleptic, an anti-psychotic, an analgesic, an anti-inflammatory, an anti-Parkinson's disease/syndrome drug, a drug for the treatment of dystonia, a drug for the treatment of spastic conditions, a drug for the treatment of benign essential/familial tremor, a drug for the treatment of tremor related to MS, a drug for the treatment of chronic encepahalopathies, a drug for the treatment of congenital CNS degeneration conditions/cerebral palsy, a drug for the treatment of cerebellar degeneration syndromes, a drug for the treatment of neuropathic and/or neurogenic pain, a drug for appetite suppression, a drug for neurodegenerative conditions, a drug for the treatment of multiple sclerosis, a drug for the treatment of insomnia, a drug for the treatment of fatigue, a drug for the treatment of vertigo, nausea and/or dizziness, a drug for the treatment of writer's cramp and restless leg syndrome, and other drugs which can beneficially be added to the treatment in order to provide an additive or synergistic effect with respect to treating the patient's disease state or condition.

For purposes of the present invention, the term "back of the neck" or "back of the neck region" is intended to encompass the area or region extending from (behind) one ear to the other ear of the human patient and from the back of the head (i.e., above the neck) to below the hairline at the back of the neck of the human patient.

For purposes of the present invention, a "topical formulation" includes, for example, ointments, creams, lotions, pastes, gels, etc., which releases one or more drugs (e.g., cannabinoid drug(s)s) at a predetermined rate over a defined period of time to a defined site of application.

For purposes of the present invention, an "injectable" formulation includes, for example, an injectable solution, suspension, gel or the like and may be in immediate release form or may provide a controlled or sustained release of the drug at the site of administration.

For purposes of the present invention, the term "immediate release" means that the cannabinoid drug(s) is administered at the site of application (e.g., the back of the neck) and is available for immediate absorption at the site of application. In other words, the term "immediate release" is meant to convey in terms of a topical formulation the fact that there is nothing in the formulation (e.g., a sustained release carrier) that would delay or slow the availability of the drug at the site of application (in contrast to, e.g., a transdermal device or patch).

For purposes of the present invention, an "implantable" formulation includes, for example, a solid, semisolid or liquid drug formulation which can be administered at the back of the neck (e.g., BONATH) either via injection and/or via surgical implantation. The solid may comprise microspheres, microcapsules, pellets, discs, and the like. The implantable formulations of the invention may provide a controlled or sustained release of the drug at the site of administration.

For purposes of the present invention, a "transdermal therapeutic system" is defined as a drug-containing device (including e.g., patch, disc, etc.) which releases one or more drugs at a predetermined rate over a defined period of time to a defined site of application.

For purposes of the present invention, "transdermal" delivery is the delivery by passage of a drug through the skin and into the bloodstream ("traditional" transdermal delivery) and is termed "transdermal systemic drug delivery (TSD therapy).

For purposes of the present invention, the term "topical neuro-affective therapy" is synonymous with the more accurately termed topical regional neuro-affective therapy (or "TRNA therapy"). This term describes important aspects of this delivery method: topical, regional (near brainstem and cervical spinal cord), and affecting the free nerve endings of the afferent nervous system, thereby not requiring the presence of drug in the blood, as with systemic therapies which includes the transdermal patch wherein the skin is used to have drug enter into the bloodstream through a continuous application patch. In such situations, an ionotophoretic electric current generator may be required to cause drug entry into blood against a concentration gradient.

For purposes of the present invention "therapeutically effective" or "effective" amount is meant to be a nontoxic but sufficient amount of a cannabinoid compound(s) to provide the desired therapeutic effect.

For purposes of the present invention, an "effective" amount of a permeation enhancer as used herein, for example, means an amount that will provide the desired increase in skin permeability and, correspondingly, the desired depth of penetration, rate of administration, and amount of drug to be delivered.

For purposes of the present invention, the term "delivers" when used with respect to the topical formulation or transdermal therapeutic system means that the formulation or system provides a mean relative release rate or flux of the drug out of the formulation or system and through the skin of the patient.

By "predetermined area of skin" is intended a defined area of intact unbroken living skin. In certain embodiments of the present invention, the predetermined area will be in the range of about 1 cm2 to about 100 cm2, preferably in the range of about 10 cm2 to about 100 cm2, more preferably in the range of about 20 cm2 to about 60 cm2. However, it will be appreciated by those skilled in the art of topical delivery that the area of skin through which drug is administered may vary significantly, depending on the formulation, dose, the application of the formulation, and the like.

"Penetration enhancement" or "permeation enhancement" for purposes of the present invention relates to an increase in the permeability of skin to a pharmacologically active agent, i.e., so as to increase the rate at which the drug permeates through the skin and enters the bloodstream. The enhanced permeation effected through the use of such enhancers can be observed by measuring the rate of diffusion of drug through animal or human skin using a diffusion cell apparatus.

For purposes of the present invention, the "brainstem afferent stimulation therapy region" is defined as the skin region of the head and/or at the frontotemporal region and/or upper posterior cervical area. In certain preferred embodiments, the treatment area is the post cervical area in close proximity to the brain stem. Preferably this area is a relatively hairless area of the patient's head and/or neck.

For purposes of the present invention, the drug may be in the form of the base, or may be provided as a pharmaceutically acceptable salt (inorganic or organic) or complex. It may be in an optically pure form or a mixture of stereoisomers.

DETAILED DESCRIPTION

Figure 1:
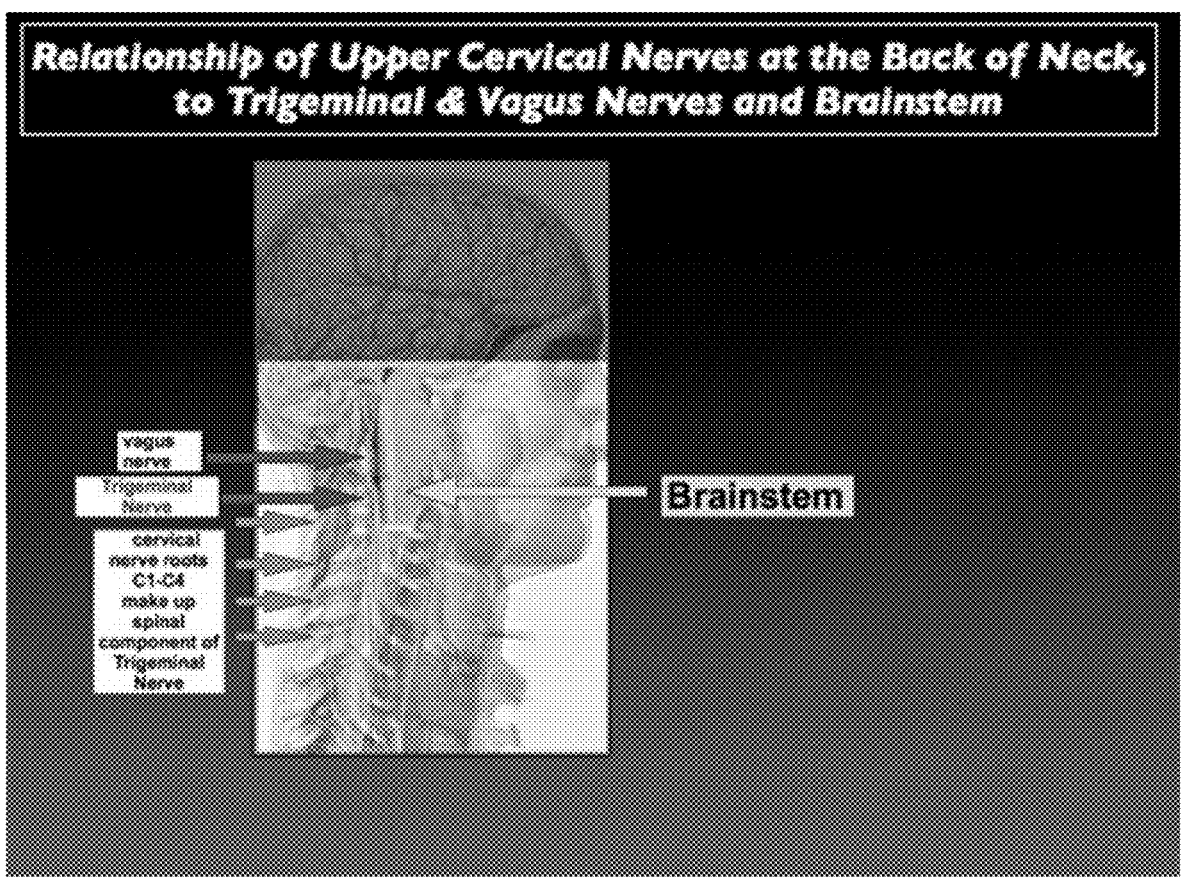
FIG. 1 is a sectional side view of a human showing the relationship of upper cervical nerves at the back of the neck, to the trigeminal and vagus nerves and brainstem.

The therapeutically active agents used in the formulations and methods of the invention comprise cannabinoid drug(s). Cannabinoids are a diverse class of chemical compounds that act on cannabinoid receptors on cells and influence neurotransmitter release in brain. These receptor proteins include endocannabinoids produced naturally in humans and animals, phytocannabinoids in *cannabis* and some other plants, and chemically manufactured synthetic cannabinoids. Endo, phyto and/or synthetic cannabinoids cause neurotransmitter release which results in nerve transmission. Phytocannabinoid A9-tetrahydrocannabinol (THC), is primary psychoactive compound of *cannabis*. Cannabidiol (CBD) is another major constituent of the plant, up to 40% extracts of plant resin. Cannabidiol (CBD) is one of many active cannabinoids in *cannabis*. The cannabinoid may be derived from endocannabinoids (derived, e.g., from foods (Omega-3s and Omega-6s); phytocannabinoids (plant derived, e.g., from buds, tinctures, extracts, including tetrahydrocannabinol (THC), cannabidiol (CBD), cannabinol (CBN), etc.); and synthetic cannabinoids (such as tetrahydrocannabinol (THC)). At least 85 different cannabinoids isolated from *cannabis* exhibit varied effects. In certain preferred embodiments, the cannabinoid drug(s), or are not psychoactive or are substantially not psychoactive (meaning that if included in the formulation, they are not in sufficient amount that a unit dose of the formulation would cause the patient to have a psychoactive effect). In certain preferred embodiments, as will be explained further below, the cannabinoid drug is actually a mixture of two or more cannabinoids (e.g., CBD and THC together in a CBD:THC ratio that provides a therapeutic effect while substantially not psychoactive or not psychoactive at all).

The endocannabinoid system ("ECS") consists of a group of endogenous cannabinoid receptors located in mammalian brain and throughout the central and peripheral nervous systems. These entail neuromodulatory lipids and their associated receptors. As the body's "endogenous," cannabinoid system, ECS is involved in a variety of physiological processes including neurological functions dealing with pain, mood, memory; and, movement, and sensation. The body's immune function and cell homeostasis is also maintained by ECS. It mediates the psychoactive effects of the *cannabis* (marijuana) plant. Cannabinoids are a diverse class of compounds that include many of the unique compounds found in marijuana.

Cannabinoids produce physiological and behavioral effects through interaction with specific membrane-bound receptors. Two primary endocannabinoid receptors have been identified: CB1 and CB2. There is mounting evidence that more endocannabinoid receptors exist. CB 1 receptors are found predominantly in brain (specifically in basal ganglia and limbic system, including hippocampus) and nervous system, as well as in peripheral organs and tissues. These are acted on by the endocannabinoid binding molecule Anandamide. Of G protein-coupled type receptors (GPCR) in human brain, cannabinoid receptors are the most plentiful. CB1 receptors responsible for euphoric and anti-convulsive effects of *cannabis*. CB2 receptors found only in peripheral nervous system appear responsible for anti-inflammatory effect such as pain relief. One other main endocannabinoid is 2-Arachidonoylglycerol (2-AG), active at both CB1 and CB2 cannabinoid receptors. Its mimetic phytocannabinoid is cannabidiol (CBD), while that of Anandamide is THC, responsible for psycho-active effects. 2-AG and CBD are involved in regulation of appetite, immune system functions and pain management.

Tetrahydrocannabinol (THC) has been the primary focus of *cannabis* research since 1964, when Raphael Mechoulam isolated and synthesized it. More recently, the synergistic contributions of cannabinoids to *cannabis* pharmacology and analgesia have been scientifically demonstrated. Other phytocannabinoids, including tetrahydrocannabivarin, cannabigerol and cannabichromene, exert additional effects of therapeutic interest. Innovative conventional plant breeding has yielded *cannabis* chemotypes expressing high titres of each component for future study.

Cannabidiol (CBD) is considered the "medical component" of *cannabis* and hemp. CBD is considered to have a wide scope of medical applications. It acts as 5-HT1A receptor agonist which may explain its antidepressant, anxiolytic, and neuroprotective effects. Cannabidiol modulates opioid receptors involved with pain perception. CBD is not psychoactive and relieves convulsion, inflammation, anxiety, and nausea. It has also been found to play a role in preventing short-term memory loss from THC. Antipsychotic effects of cannabidiol represent potential treatment of schizophrenia. Oral CBD formulation received orphan drug status in US as treatment for Dravet syndrome, an intractable seizure disorder also known as Severe Myoclonic Epilepsy of Infancy (SMEI). Nabiximols, trade name Sativex, is an aerosolized mist for oral administration containing 1:1 ratio of CBD and THC approved 2005 in Canada for multiple sclerosis associated pain. CBD has a greater affinity for CB2 than CB 1 receptor.

CBD acts as serotonin (5-HT1A) receptor agonist which may explain its antidepressant, anxiolytic, and neuroprotective effects. CBD modulates opioid receptors involved with pain perception. CBD is not psychoactive and relieves convulsion (seizures), inflammation, anxiety, and nausea. It has been found to play a role in preventing short-term memory loss from THC. Antipsychotic effects of cannabidiol represents potential treatment of schizophrenia. CBD has a greater affinity for CB2 than CB 1 receptors.

Strains of *cannabis* containing higher CBD concentrations did not produce short-term memory impairment compared to those with similar concentrations of THC, but lower CBD concentrations. Attenuation of memory effects attributed to CBD's function as CB 1 antagonist. Transdermal CBD has been shown to be neuroprotective in animals. Antioxidant properties of cannabidiol have been shown to play a role in its neuroprotective and anti-ischemic effects. Animal experiments indicate CBD may help in treating Parkinson's disease.

It is known to those skilled in the art that studies have suggested that many cannabinoid compounds work together to produce a synergy of effects. This is known as the 'entourage effect." Thus, in certain preferred embodiments, the formulations of the invention contain more than one cannabinoid compound, which provide an "entourage effect."

CBD has anti-psychotic effects which may counteract psychotomimetic effects of THC, euphoric and hallucinogenic component of *cannabis*. Reports show CBD safe and well-tolerated alternative treatment for schizophrenia. A double blind trial comparing purified cannabidiol to atypical antipsychotic amisulpride in acute paranoid schizophrenia showed both treatments were associated with significant decrease in psychotic symptoms after 2 weeks; but cannabidiol was associated with significantly fewer side effects. Studies show cannabidiol affects limbic system, decreasing symptoms of social anxiety and isolation. Cannabidiol has demonstrated antidepressant-like effects in animal models of depression.

In certain preferred embodiments, the cannabinoid is not psychoactive, or only mildly psychoactive. Cannabidiol (CBD) is not psychoactive, and therefore in certain preferred embodiments, the active cannabinoid drug comprises cannabidiol, or consists essentially of cannabidiol, or consists of cannabidiol. In other preferred embodiments, cannabidiol comprises from about 5% to about 99.9% of the total amount of cannabinoid drug(s) included in the formulations and treatments of the present invention. In other preferred embodiments, cannabidiol comprises about 20%, about 30%, about 40%, about 50%, about 60%, about 70%, about 80%, about 90% or more, or greater than about 95% of the total amount of cannabinoid drug(s) included in the formulations and treatments of the present invention. In certain embodiments, the CBD is derived from crystalline powder, such that the powder is about 95% pure CBD or greater. In other preferred embodiments, cannabidiol comprises at least about 20% of the total amount of cannabinoid drug(s) included in the formulations and treatments of the present invention. In other embodiments, the cannabinoid drug comprises cannabinol (which is only mildly psychoactive). In certain embodiments, the cannabinoid drug(s) contained in the formulations of the invention is hemp CBD. In other embodiments, the cannabinoid drug(s) is *cannabis*-based and comprises a THC-CBD (and optionally other cannabinoid combinations derived from *cannabis*). As CBD and THC have different mechanisms of action, they may act synergistically, e.g., to control seizures. In such embodiments, the therapeutic effect may be via the "entourage effect".

In other embodiments, the drug is a cannabinoid such as an endocannabinoids (derived, e.g., from foods (Omega-3s and Omega-6s); a phytocannabinoid (plant derived, e.g., from buds, tinctures, extracts, including tetrahydrocannabinol (THC), cannabidiol (CBD), cannabinol (CBN), etc.); and synthetic cannabinoids (such as tetrahydrocannabinol (THC)), mixtures thereof, and the like. Further representative cannabinoids useful in the present invention include cannabigerol (CBG), cannabichchromene (CBC), cannabicyclol (CBL), tetrahydrocannabivarin (THCV), cannabidivarin (CBDV), cannabichromevarin (CBCV), cannabigerovarin (CBGV), delta-8-tetrahydrocannabinol, delta-9-tetrahydrocannabinol (Dronabinol), cannabigerol monomethyl ether (CBGM), nabilone, rimonabant (SR141716, a selective cannabinoid ($CB_1$) receptor inverse agonist), JWH-018, JWH-073, CP-55940, dimethylheptylpyran, HU-331, SR 144528 (a selective $CB_2$ receptor agonist), levonantradol, AM-2201, beta-caryophyllene, lipophilic alkamides (alylamides) which have affinity for the $CB_2$ receptor, and chemical derivatives of any of the foregoing. In certain embodiments, a synthetic cannabinoid is used. Synthetic cannabinoids encompass a variety of distinct chemical classes: the classical cannabinoids structurally related to THC, including the nonclassical cannabinoids (cannabimimetics) including the aminoalkylindoles, 1,5-diarylpyrazoles, qualene18p, and arylsulfonamides, as well as eicosanoids related to the endocannabinoids. Cannabigerol ("CBG") is non-psychotomimetic but still impacts the overall effects and affects of *cannabis*. CBG acts as a alpha2-adrenergic receptor agonist, 5-HT1A receptor antagonist, CB 1 receptor antagonist, and also binds to the CB2 receptor. CBC is non-psychoactive, and exhibits anti-inflammatory and analgesic properties. Evidence suggests that CBC may play a role in anti-inflammatory and anti-viral effects, may have antidepressant effects, may promote neurogenesis, and may contribute to the overall analgesic effects of *cannabis*. Delta-9-tetrahydrocannabinol (Dronabinol; commercially available in the U.S. under the tradename Marinol) is used as an appetite stimulant, anti-emetic, and analgesic. Nabilone (Cesamet, Canemes), a synthetic cannabinoid and an analog of Marinol; Rimonabant (SR141716), a selective CB 1 receptor inverse agonist once used as an anti-obesity drug under the tradename Acomplia, and was also used for smoking cessation.

In certain embodiments, the cannabinoid drug(s) is industrial hemp or a non-psychoactive hemp product.

In yet further embodiments, the cannabinoid drug(s) comprises a natural cannabinoid compound, a synthetic cannabinoid compound, a semi-synthetic cannabinoid compound, or mixtures thereof. Illustrative of such compounds are cannabinoids or cannabinoid analogues selected from the group consisting of cannabinol, cannabidiol, delta 9-tetrahydrocannabinol, delta 8-tetrahydrocannabinol, hydroxy-tetrahydrocannabinol, 11-hydroxy-9-tetrahydrocannabinol, levonantradol, delta 11-tetrahydrocannabinol, tetrahydrocannabivarin, dronabinol, amandamide, nabilone, a natural or synthetic analogue thereof, a natural or synthetic molecule with a basic cannabinoid structure, and mixtures of any of the foregoing.

In certain embodiments, the cannabinoid drug(s) included in the treatment and/or formulations of the present invention comprise a ligand that binds to the $CB_1$ or the $CB_2$ receptor.

*Cannabis* terpenoids (e.g., limonene, myrcene, α-pinene, linalool, β-caryophyllene, caryophyllene oxide, nerolidol and phytol) share a precursor with phytocannabinoids, and are all 19quale and fragrance components common to human diets that have been designated Generally Recognized as Safe by the US Food and Drug Administration and other regulatory agencies. Terpenoids are quite potent, and affect animal and even human 19qualene when inhaled from ambient air at serum levels in the single digits ng·Ml-1. They display unique therapeutic effects that may contribute meaningfully to the entourage effects of *cannabis*-based medicinal extracts. Thus, in certain embodiments, the formulations and treatments of the present invention include an active drug component which comprises both a phytocanna binoid(s) and a terpenoid(s). Phytocannabinoid-terpenoid interactions may produce synergy with respect to treatment of pain, inflammation, depression, anxiety, addiction, epilepsy, cancer, fungal and bacterial infections (including methicillin-resistant *Staphylococcus aureus*).

Administration at the Back of the Neck

The cannabinoid drug formulations of the present invention are preferably applied at the back of the neck region of the human patient. In its broadest sense, the term "back of the neck" or "back of the neck region" is intended to encompass the area or region extending from (behind) one ear to the other ear of the human patient and from the back of the head (i.e., above the neck) to below the hairline at the back of the neck of the human patient. More preferably, the administration of the cannabinoid drug(s) is located more directly at the back of the neck in the area above the cervical nerve roots, C1-C4 (and optionally including C5) such that administration of the cannabinoid drug(s) are in the area at or above the skin where the afferent components of trigeminal nerve system, cervical sympathetic nerves, and vagus nerve are located. In certain preferred embodiments, the back of the neck is more specifically the back of the neck at or around the hairline of the patient, which is an area more directly above the C1-C4 cervical nerve roots (this area is referred to herein as "BONATH"). It is to be understood that application at the back of the neck is not an exact art, and application of part or all of the dose in proximity to the back of the neck (e.g., behind the ears or on the skin higher (on the back of the head) or lower (below the hairline, and even below the C5 area) than directly above the C1-C4 cervical nerve roots will still provide a therapeutically effective dose in accordance with the invention; however, such locations are not optimal and may cause a lessening of the therapeutic effect or a delay in onset of therapeutic effect. All such treatments are considered to fall within the definition of "back of the neck" for purposes of the present invention.

The administration of a cannabinoid drug(s) at the back of the neck is a novel way to deliver cannabinoids. This is believed to be accomplished by activation of cutaneous afferent pathways through neuro-chemical receptors existing on free nerve-endings. The hypothesis of this therapeutic modality is based on presence of numerous (hundreds of thousands to millions) of free nerve-endings below the skin surface (stratum corneum) at upper posterior cervical region, the back of the neck or "nuchal" region. There exist at this location, direct connections through cervical nerve roots, C1-C4, and occasionally, C5, to afferent components of trigeminal nerve system, cervical sympathetic nerves, and vagus nerve providing significant input to CNS. At no other location on the human body is such a magnitude of afferent neural input accessible through skin nerve-endings than here. Modulated CNS efferent neural outflow in response to afferent activation manifests as improvement in clinical symptoms of MS and other conditions of brain and spinal cord impairment. By using direct nerve pathways, by-passing blood flow and avoiding restrictions of "blood-brain-barrier," onset of therapeutic time is greatly reduced and systemic side effects are avoided.

The inventor has observed rapid therapeutic onset of action, generally, less than 10 to 15 minutes administration of cannabinoid drug(s) at the back of the neck, with maximal benefit noted well within 30 minutes. In certain embodiments, a prolonged therapeutic effect has been noted, e.g., about 4 to about 12 hours or more, depending on condition and severity of the condition being treated.

The peripheral nervous system (PNS) communicates with central nervous system (CNS, consisting of brain, brainstem, and spinal cord) through dorsal root ganglia which reside just outside the spine and act as neural relay areas between PNS and CNS. The human skin has free nerve endings just below the skin surface (stratum corneum), which are the peripheral end components of spinal dorsal root ganglia. As skin and CNS are both derived from the same embryological tissue, neuro-ectoderm, receptors to neurotransmitters and other substances used in neural communication are similarly represented on both free nerve endings and CNS. This makes sense as the skin needs to communicate directly with CNS with respect to external stimuli. In fact, these receptors are on the cell surface of skin free nerve endings, making them readily accessible to compounded drug applications to the skin for neural effect, "topical neuro-affective therapy." The binding of the topically administered cannabinoid drug(s) to these receptors results in electrical action potential generation and propagation to CNS, causing therapeutic effects to occur. As such, these same drug compounds do not need to enter the bloodstream to reach their sites of activity, as it is with systemic delivery. Systemic side effects and drug activity at sites other than intended are therefore not present. Further, by working through established neural pathways than through the blood stream, the therapeutic effects are rapid, generally with 15-30 minutes or less. Many of the current drugs used systemically for peripheral conditions such as pain are thought to work by their effect on dorsal root ganglia, modulating neural impulses to brain. With topical neuro-affective therapy the effects on dorsal root ganglia are direct and immediate as free nerve endings are peripheral extensions of the ganglia.

An important aspect of the benefits of "TRNA" or "RNA" therapy in CNS drug delivery for brainstem related disorders lies in the anatomy of the region. The free nerve endings with receptors for the neuro-chemicals dopamine, serotonin, norepinephrine, and others are located just below the surface of the skin, easily assessable to drugs compounded in an appropriate dermal penetration enhancing medium and topically applied to the skin.

To understand the concept of "peripheral neural afferent stimulation therapy" as it applies to the brainstem and how topical drug delivery to the back of the neck works requires a review of the neuro-anatomy and the neuro-physiology of the region. As indicated above, this area of the nervous system is very complicated, compact and highly inter-active and inter-related.

The Trigeminal Nerve System is a component of the brainstem which coordinates pain input from the face, head, and the back of the neck. As such, it intimately influences the production of other symptoms associated with syndromes attributed to dysfunction within the trigeminal complex. These include the photophobia, phonophobia, nausea, anxiety, allodynia, and other focal sensory symptoms which may accompany a migraine attack. Similarly, episodes of trigeminal neuralgia (tic douloreux) frequently involve significant affective (emotional) and visceral components. Because of proximity and connections to other structures in the brainstem, abnormalities of temperature regulation, thirst, alertness, and mood are common. Some of these symptoms may be as equally disabling as the head and face pain.

In addition to receiving pain and sensory (afferent) input from the face, nasal and para-nasal sinuses, the teeth, scalp, the dura of the anterior and middle cranial fossa, the trigeminal system receives similar input from the soft tissues of the posterior cervical region. The free nerve endings in the back of the neck are just below the surface of the skin, easily accessible to topically delivered drugs formulated in an appropriate dermal penetration enhancing compounding medium. The free nerve endings, via the small un-myelinated and myelinated "C-fibers" (pain fibers) carry pain impulses through afferent sensory nerves back to the Trigeminal Nucleus Caudalis (TNC). TNC is the pain processing center extending from the pons through the entire extent of the brainstem to the upper cervical spinal cord. After synapsing at the thalamus, pain impulses from TNC travel to the somatosensory cortex, where pain is perceived.

As providing important afferent input to the brain, the trigeminal system also receives afferent input from the rest of the body. Afferent input is defined as any neural impulses coming back to the brain from the body. As such it provides information to the brain for processing and interpretation: pain, sensation, autonomic functions. Efferent output, on the other hand, consists of impulses originating in the central nervous system (brain, brainstem, and spinal cord) flowing to the body for function: movement, response, action.

FIG. 1 is a sectional side view of a human showing the relationship of upper cervical nerves at the back of the neck, to the trigeminal and vagus nerves and brainstem. The vagus nerve includes both efferent and afferent fibers and is attached to the lower brainstem (medulla oblongata) via 8-10 radicles. The afferent fibers arise in the jugular and the nodose vagus ganglia. The somatic afferent fibers terminate in the nucleus of the trigemino-spinal tract (TNC). Both the jugular and the nodose ganglia are connected with the superior cervical sympathetic gangion through inter-communicating rami. The superior cervical sympathetic ganglion is located between the internal carotid artery and the jugular vein on the ventral aspects of the transverse processes of the 2nd, $3^{rd}$, and the $4^{th}$ cervical vertebrae. It is the largest of the sympathetic trunk ganglia.

Sympathetic roots arising from the ganglion join the 1st and the 2nd cervical nerves; frequently the 3rd, and occasionally, the 4th. In addition to nerve fibers which extend rostrally from the superior cervical sympathetic ganglion, the sympathetic innervation of the head includes fibers which join the plexi on the common carotid and the vertebrtal arteries. The one on the vertebral artery is continuous with the plexus on the basilar artery. Rami derived from the internal carotid plexus join the trigeminal nerve and the cavernous plexus in addition to the other structures such as the abducens and deep petrosal nerves. From the cavernous plexus, located in the middle cranial fossa, sympathetic fibers join the oculomotor, trochlear, and the ophthalmic nerves. Fibers from the plexus also accompany blood vessels into the hypophysis. The spheno-palatine gangion, located in the pterygo-palatine fossa, receives sypmpathetic fibers from the face with rami distributed to the mucous membranes of the nares, mouth, the pharynx, and some orbital structures.

From the above, it is clear that cervical nerve function is intimately related to vagal afferents and afferents from the face, head, and the dura of cranial fossae associated with migraine and other head and face pain syndromes.

It has been long reported that vagal nerve stimulation (VNS) in the neck down-regulates abnormal discharges from epileptic foci and treats seizures. VNS is now approved as adjunct to medical therapy in certain forms of intractable epilepsy. It is also of benefit in severe depression resistant to traditional drug therapy. Studies with VNS in migraine, anxiety, and fibromyalgia have been underway and have shown preliminary promise in benefit. The mechanism of action appears to be the down-regulation of hyper-excitable, dysfunctional neuronal systems by increased inhibitory input to brainstem and associated connections through stimulation of the afferent system. Afferent stimulation, by feed-back through TNC, causes reduction in efferent output from the brainstem, resulting in resolution of clinical symptoms through down-regulation of hyper-active neuronal structures.

In the same way the electrical stimulation of VNS accomplishes its effect on the brainstem, topical drug therapy to the posterior cervical region, in close proximity to the brainstem and its afferent inputs, is theorized to provide effect for the conditions mentioned above.

It is hypothesized that benefits of the present method of topical drug delivery of central nervous system (CNS) active drugs lies in the fact that drug concentration gradients and blood flow factors are un-involved in the therapeutic process. In contrast, the proposed delivery operates through direct nerve connections between skin peripheral nerves at the back of the neck, for example at the hairline (BONATH) and brainstem structures. Active drug compounded in an appropriate "dermal penetration enhancing" medium topically applied to the skin at the back of neck has effect on the free nerve endings of peripheral nerves located immediately below the skin surface. Receptors to dopamine, serotonin, norepinephrine, and other neuro-transmitters/neuro-chemicals involved with neural transmission are located on these free nerve endings. Therefore, topically applied drug has near immediate therapeutic effect as direct neural impulses are involved—the concept of brainstem afferent stimulation through topical regional neuro-affective (TRNA) therapy. All prior art and methods of drug delivery to the CNS have involved blood flow and therapeutic drug blood level requirements. The inventive method does not require such, which are the source of undesirable systemic and CNS side-effects. The present drug delivery process operates on the principle of an electrical capacitor whereas the prior relied on those fluid dynamics and reservoir principles.

The factors which determine the success of TRNA therapy include: the drug being considered, the compounding substance (surfactant/dermal penetration enhancer), the disease process, and the location of application. The free nerve endings in the skin at the back of the neck are important components of the cervical nerves with rich connections to the trigeminal, vagal, and sympathetic systems communicating with brainstem structures and other components of the central nervous system. These are the areas pain and other symptoms related to neuro-chemical release are processed and perceived.

The skin at the upper part of the back of the neck, at the hairline, is innervated by (supplied by nerves) the cervical nerve roots C1-3 that are also part of the Trigeminal Nerve system of the brainstem. These cervical nerves (the wires) have their cell bodies (their generators) within the Nucleus Caudalis (Spinal Nucleus) of the Trigeminal Nerve in the cervical spinal cord and the brainstem. Accordingly, they have direct neural connections with brainstem processing areas. At the same time, the peripheral nerve receptor sites for these nerves, the free nerve endings, reside under the skin surface at the back of the neck. The nerves in the soft tissues of the back of the neck, representing the C1, C2, and C3 segments of the cervical spinal cord are unique in that they have intimate connections with pathways directly affecting brainstem and autonomic system function. There are direct connections with the Trigeminal Nerve system of the brainstem which provides for pain and other sensory input and interpretation from the head, face, sinus cavities, the dural covering of the brain, and the back of the neck. There are also connections with the vagus nerve and the sympathetic nervous system through the sympathetic ganglia. It is through these connections, which are nowhere else in the body as inter-related or at such close proximity to the surface of the human skin, that the potential for the delivery of CNS acting drugs through the skin at the back of the neck (BONATH) is realized. Finally, skin is embryologically derived from neuro-ectoderm which is also responsible for the formation of the brain and other aspects of the CNS. Thus, the nerves in the human skin have a particularly direct relationship with these structures. This provides for the efficacy noted with TRN/back of the neck therapy. At the same time, systemic and other CNS side-effects are reduced or avoided. Thus, drugs topically applied to the skin in this region have ready access to brainstem and other CNS structures without the requirement of drug in the bloodstream reaching target sites.

In addition to the upper cervical nerves having direct relation to the Trigeminal Nerve System, they also contribute to the Cervical Sympathetic Ganglia and the Vagal Nerve Systems through direct connections. These latter two systems provide some of the most significant afferent feed-back to the brainstem and other portions of the CNS from the rest of the body. This allows for additional brainstem afferent stimulation potential through TRNA therapy at the back of the neck. Although skin at other areas of the face and head have eventual neural feed-back to the brainstem, the intimate connections to afferent feed-back systems are lacking.

The question arises then: does TRNA therapy work with drug application to the forehead, face, or other regions of the head. The answer is perhaps—in some disease states such as migraine and face pain; but not as effective and efficient as at the back of the neck or at the back of the neck at the hairline (BONATH). Free nerve endings are also present at these other locations but the distance back to involved brainstem structures is greater and there is not the added advantage of rich afferent neural connections to the trigeminal, vagal, and sympathetic nerve systems that are associated with the posterior cervical region.

TRNA therapy at the back of the neck or at the BONATH delivery differs from traditional therapy (whether oral, injection, nasal spray, inhalation, or rectal) in that it has no reliance on the systemic or cerebral blood flow. Nor does it require therapeutic blood levels of drug. These latter factors are responsible for systemic and CNS side-effects as drug is delivered to areas not intended to be affected in the therapeutic process. Transdermal systemic delivery by patch, although similarly applied to the skin as in TRNA therapy, differs significantly in its reliance on a drug concentration gradient for absorption into the systemic capillary and venous blood. TRNA therapy is unaffected by dermal vessels or systemic blood flow. It relies solely on the function of the free nerve endings of cutaneous nerves and their connections at the point of application of compounded drug.

"Traditional" transdermal drug delivery by patch and TRNA are both "transdermal" in that in both, drug penetrates the skin (epidermis) for eventual clinical effect. The difference lies in the fact that in "traditional" transdermal patch therapy, drug enters the systemic circulation through a concentration gradient and establishes a therapeutic drug blood level. Although measuring a blood level gives assurance drug is being taken or delivered systemically, allowing for checking compliance, it is also the source of undesirable side-effects and drug interactions. Of necessity, with systemic transdermal patch therapy, drug applied to the skin surface must be absorbed through the small vessels in the dermis for eventual presence in the systemic venous blood for measurement of drug level. With TRNA therapy, the cannabinoid drug(s) need only be available at the free nerve endings under the epidermis. No concentration gradients or systemic blood levels are necessary. Drug delivery is unaffected by cardiac output or cerebral blood flow factors. Of significance, persons afflicted with Parkinson's disease are typically elderly with concomitant cardiac and cerebral vascular disease.

Thus, in certain embodiments, the methods and formulations of the invention deliver an amount of drug (e.g., cannabinoid drug(s)) in the TRNA therapy that would provide sub-therapeutic plasma levels if administered orally, but which is therapeutically effective when administered via TRNA therapy at the back of the neck or at the BONATH.

It is hypothesized by the inventor that a principal reason TRNA therapy is rapid in the onset of clinical effect (e.g., less than about 10-15 minutes) for is that it operates through an "electro-chemical" process. Active drug compounded in an appropriate dermal penetration enhancing medium acts at free nerve endings, changing the neurochemistry of receptors at the neural synapse: apomorphine (dopamine and norepinephrine agonist), increasing dopamine and norepinephrine levels and improving neural transmission. After a point of receptor stimulation, neural (electrical) impulses are generated back to neuronal cell bodies residing in the spinal cord and brainstem: "afferent feed-back". The nervous system functions through neurons generating electrical impulses and the release of neurochemicals/neuro-transmitters (serotonin, norepinephrine, dopamine, and acetylcholine, being the major ones) at neural receptor sites called "synaptic clefts". Accordingly, the process in TRNA therapy may be considered analogous to an electrical capacitor discharging to perform a function, such as turning on a light switch. Viewed from this perspective, the rapid onset of clinical effect observed in TRNA therapy makes sense.

Alternatively, transdermal systemic patch delivery operates on the principles of chemical gradients and fluid dynamics. These processes have variability and inherent idiosyncrasies, fluctuating heart function as a pump for blood flow being one. Thus, despite the advantage of measurable drug levels, a more circuitous route with slower clinical effect is observed. This makes systemic transdermal patch delivery inappropriate for acute therapy.

Therapeutic Applications

Potential clinical applications of cannabinoids applied at the back of the neck in accordance with the present invention include the following: seizures; epilepsy; encephalopathy, including lethargy, focus/attentional problems, and cognitive issues; spasticity; weakness (e.g., muscle weakness); pain, including radiculopathy and neuropathy, lower back pain, and fibromyalgia; neuropathic pain; numbness and/or tingling; anxiety and other mood disorders; hypertension and autonomic dysfunction; Parkinson's disease and tremors, including Essesntial Tremor; insomnia; Bell's palsy and facial nerve dysfunction; glaucoma (marijuana is known to reduce pressure in the eye); multiple sclerosis (an extract that relieves pain and muscle spasms in MS patients has been approved in Europe and Canada, though not in the U.S. iNabiximols, trade name Sativex, an aerosolized mist for oral administration containing 1:1 ratio of CBD and THC)); AIDS (one of the FDA-approved synthetic versions of a substance found in marijuana, $(-)$-trans-$\Delta^9$-tetracydocannabinol (generally referred to as dronabinol) helps increase appetite and treat weight loss in patients with the disease); cancer (dronabinol is also marketed in the U.S. to treat nausea associated with chemotherapy; researchers have reported CBD's ability to "turn off" the activity of ID1, a gene responsible for metastasis in breast and other types of cancers, including aggressive triple negative breast cancer; PTSD; trigeminal neuralgia; hemi-facial spasms; Autism/Asperger's; Attention Deficit Disorder and Hyperactivity; social isolation; occipital neuralgia; TMJ dysfunction related symptoms; cognitive problems including memory disturbance; headaches (migraine and tension); peripheral neuropathy; Dravet syndrome (an intractable seizure disorder also known as Severe Myoclonic Epilepsy of Infancy (SMEI)—an oral CBD formulation received orphan drug status in US as treatment for this condition); apnea (including central sleep apnea, obstructive sleep apnea syndrome, and mixed apneas (having components of central and obstructive sleep apneas); smoking cessation; arthritis, including rheumatoid arthritis; depression; emesis; anti-obesity; nausea; vomiting; alcohol use disorders; dystonia; inflammatory bowel syndrome; neuropathic pain associated with post-herpetic neuralgia; diabetic neuropathy; shingles; burns; actinic keratosis; oral cavity sores and ulcers; post-episiotomy pain; psoriasis; pruritis; contact dermatitis; eczema; bullous dermatitis herpetiformis; exfoliative dermatitis; mycosis fungoides; pemphigus; severe eryththema multiforme; seborrheic dermatitis; ankylosing spondylitis; psoriatic arthritis; Reiter's syndrome; gout; chondrocalcinosis; joint pain; dysmenorrhea; musculoskeletal pain; molymyositis; bursitis; epicondylitis; osteoarthritis; synovitis; pancreatitis; and other disease states and conditions which will be apparent to those skilled in the art.

In certain preferred embodiments, the cannabinoid drug(s) is formulated in a vehicle that allows for the drug to be immediately absorbable and available for the free nerve endings of the trigeminal nervous system which reside under the skin surface at the back of the neck when the formulation is, e.g., applied to the back of the neck of a human patient in the form of a cream, gel or ointment. On the other hand, it is contemplated in certain embodiments of the invention that the topical or implantable cannabinoid drug(s) formulation can be administered in the form that provides a prolonged release at the back of the neck, for example, in the form of a transdermal patch. The uniqueness of this particular area of the human anatomy which allows this delivery method to work. In further embodiments, the cannabinoid drug(s) is applied (i) in a topical form that provides a therapeutically effective dose of the cannabinoid drug(s) immediately absorbable at the site (back of the neck), and (ii) a further therapeutically effective dose(s) in a prolonged or sustained release formulation (e.g., a transdermal patch or contained in liposomes) that releases the cannabinoid drug(s) over time such that the cannabinoid drug(s) is absorbed at the back of the neck in therapeutically effective amounts over a span of multiple dosage time intervals (e.g., 1-7 days).

A unit dose of the topical formulation(s) of cannabinoid drug(s) used in accordance with the present invention preferably includes from about 1 mg to about 200 mg cannabinoid drug(s), based on the cannabinoid drug comprising at least 80% cannabidiol, in certain preferred embodiments at least 90% cannabidiol, and in certain further preferred embodiments at least 95% cannabidiol. In certain preferred embodiments, the amount of psychoactive cannabinoid drug(s) present in the topical formulations of the present invention is less than 20%, more preferably less than 10% or less than 5% of the total active cannabinoids in the topical formulation.

A representative cannabinoid drug mixture concentrate may include with respect to total active cannabinoids, for example, from about 0 to about 3% tetrahydrocannabinol, from about 0 to about 1% tetrahydrocannabinolic acid, from about 20 to about 50% cannabidiol, from about 0 to about 1% cannabidiolic acid, and from about 0 to about 1% cannabinol, for a total active cannabinoid level of from about 20% to about 50%. A particular cannabinoid concentrate useful in the formulations of the present invention may include, e.g., about 0.84% tetrahydrocannabinol, about 0.23% tetrahydrocannabinolic acid, about 26.41% cannabidiol, about 0% cannabidiolic acid, and about 0.09% cannabinol, for a total active cannabinoid level of about 27.58%, as detected using full spectrum cannabinoid profiling and analysis utilizing High Performance Liquid Chromatography (HPLC/UV), and is commercially available from CannaVest. Such a cannabinoid drug mixture may provide the afore-mentioned entourage effect.

In certain embodiments, the topical cannabinoid formulation of the present invention is administered at the back of the neck on the human patient and a therapeutic effect is preferably provided within about 45 minutes, preferably within about 30 minutes, or 25 minutes, or 20 minutes, or 15 minutes, or 10 minutes after the administration. In certain preferred embodiments, a therapeutic effect is noticed within about 10 to about 15 minutes after the administration (e.g., application of the topical formulation to the back of the neck).

In certain embodiments, the topical cannabinoid formulation is administered on an "as needed" basis. In other embodiments, the topical cannabinoid formulation is administered on a once a day basis, or on a twice a day basis, or on a three times a day basis, or on a four times a day basis.

In certain preferred embodiments, a unit dose of the topical cannabinoid drug(s) formulation provides a cannabinoid (e.g., CBD) dose from about 0.1 mg to about 200 mg, and in certain embodiments more preferably from about 3 mg to about 50 mg or from about 7.5 mg to about 30 mg. This may be administered in a topical cream, ointment, gel or the like. For example, the topical formulation may be administered as a unit dose in an amount from about 0.5 g to about 1 g at a cannabinoid (e.g., CBD) concentration from about 0.1% to about 5% (or more).

Combination Therapy

In certain preferred embodiments of the invention, the cannabinoid(s) is administered together with (e.g., in the same formulation), or simultaneously (but separately) or sequentially with an additional active agent(s) ("drug(s)") suitable for treating the patient's disease state or condition. Classes of drugs which would be suitable as an additional active agent(s) include, but are not limited to:

1. Anti-Epileptic drugs: Examples of a second therapeutic agent(s) include Valproic acid (Depacon®/Depakot®e), Leviteracetem (Keppra®), Lamotrigene (Lamictal®), Topiramate (Topamax®), Pregabalin (Lyrica®), Gabapentin (Neurontin®), Carbamazepine (Tegretol®), Oxcarbazepine (Trileptal®), Phenobarbital and other barbiturates, Tiagabine (Gabatril®), Retigabine™ (Valeant Pharmaceuticals), Lacosamide® (Schwarz Biosciences), and Perampanel® (Eisai) are in development as anti-epileptics and neuromodulators for other associated neurological, pain, and psychiatric conditions.
2. Anxiolytic drugs: Benzodiazepines: Examples of a second therapeutic agent(s) include lorazepam (Ativan®), diazepam (Valium®), clonazepam (Klonopin®), chlordiazepoxide (Librium®), and alprazolam (Xanax®).
3. Neuroleptics/Anti-Psychotic drugs: Examples of a second therapeutic agent(s) include chlorpromazine (Thorazine®), haloperidol (Haldol®), risperidone (Risperdal®), olanzapine (Zyprexa®) and quetiapine (Seroquel®).
4. Analgesics/Anti-Inflammatory drugs: Examples of a second therapeutic agent(s) include prednisone, solumedrol, and other steroids, naproxen, aspirin, acetaminophen, voltaren, ketoprofen, ibuprofen, other NSAID's.
5. Parkinson's Disease/Similar or Related Syndrome (e.g., tremors, spasticity and spasms, dystonia) drugs: Examples of a second therapeutic agent(s) include dopamine agonists such as apomorphine.
6. Dystonia (cervical and otherwise), which sometimes occur in conjunction with spasmdic torticollis and spastic conditions: Examples of a second therapeutic agent(s) include dopamine agonists such as apomorphine.
7. Benign essential/familial tremor, tremor related to MS, chronic encepahalopathies such as from stroke or head injuries, congenital CNS degeneration conditions/cerebral palsy, cerebellar degeneration syndromes, and spasicity conditions from the above: Examples of a second therapeutic agent(s) of a second therapeutic agent(s) include dopamine agonists such as apomorphine.
8. Neuropathic/Neurogenic pain drugs: Examples of a second therapeutic agent(s) include carbamazepine, gabapentin, topiramate, zonisamide, phenytoin, desipramine, amitriptyline, imipramine, doxepin, protriptyline, pentoxifylline, and hydroxyzine.
9. Smoking Cessation drugs: Examples of a second therapeutic agent(s) include drugs such as varenicline.
10. Appetite Suppressant drugs: Examples of a second therapeutic agent(s) include drugs such as Sibutramine.
11. Neurodegenerative Diseases: Examples of a second therapeutic agent(s) include Aricept/donepezil, Exelon/rivastigmine, Reminyl/Razadyne/galantamine, and Namenda/memantine and their naturally occurring counterparts, as well as NMDA antagonists.

12. Multiple Sclerosis (MS): Examples of a second therapeutic agent(s) include drugs such as 4-aminopyridine.
13. Insomnia: Examples of a second therapeutic agent(s) include drugs such as zolpidem or melatonin.
14. Fatigue: Examples of a second therapeutic agent(s) include drugs such as pemoline and Modafinil.
15. Vertigo, Nausea and/or Dizziness: Examples of a second therapeutic agent(s) include drugs such as as meclizine, dimenhydrinate, prochlorperazine, scopolamine and diphenhydramine.
16. Writer's cramp and restless leg syndrome: Examples of a second therapeutic agent(s) include dopamine agonists such as apomorphine.
17. Migraine: examples of a second therapeutic agent(s) include serotonin agonists, such as sumatriptan; ergot alkaloids such as ergotamine; skeletal muscle relaxants such as tizanidine; and combinations of any of the foregoing.
18. Muscle spasms and spasticity: examples of a second therapeutic agent(s) include skeletal muscle relaxants such as tizanidine, as a norepinephrine alpha-adrenergic receptor agonist; 4-amino pyridine, with agonist and antagonist activities at neurochemical receptor sites affecting glutamate, dopamine, serotonin function in CNS, as well as that of other neurotransmitters to improve nerve conduction, reduce spasticity, and improve neurological function in multiple sclerosis, MS, stroke; and brain and spinal cord injuries.
19. Peripherally applied, topical 4-amino pyridine found useful in diabetic peripheral neuropathy, DPN, and other peripheral neuropathic conditions.
20. ADD/ADHD and/or Tourette's syndrome: an example of a second therapeutic agent(s) would be phentermine.
21. Anxiety and/or panic attacks and/or mood disorders: an example of a second therapeutic agent(s) is milnacipran.

In certain embodiments, the additional drug(s) includes a dopamine agonist such as apomorphine (Apokyn®, APO-Go®), pramipexole (Mirapexin®), ropinirole (Requip®), bromocriptine (Parlodel®), cabergoline (Cabaser®, Dostinex®), pergolide (Permax®, Celance®) rotigotine (Neupro®), mixtures of any of the foregoing, or other dopamine agonists known to those skilled in the art. One skilled in the art will appreciate that dopamine agonists other than apomorphine may be used in the formulations and methods of the present invention, and all such agents are meant to be encompassed by the term "dopamine agonists." For example, such drugs include, but are not limited to, carbidopa (Sinemet®), dopamine agonists (Requip®, Rotigotine®, Mirapex®), COMT inhibitors (Entacapone®, Tocapone), rasagiline (Azilect®) (MAO inhibitors) and MAO-B inhibitors (Selegiline (Eldepryl®). In certain preferred embodiments, the concentration of dopamine agonist included in the topical unit dose is from about 0.25 mg to about 4 mg, based on apomorphine, or an therapeutically equivalent amount of another dopamine agonist as described herein.

In other embodiments, the additional drug(s) includes an opioid such as morphine, codeine, dihydrocodeine, hydrocodone, hydromorphone, nicomorphine, oxycodone, oxymorphone, fentanyl, alphamethylfentanyl, alfentanil, sufentanil, remifentanyl, carfentanyl, ohmefentanyl, thebaine, oripavine, diacetylmorphine (heroin), phenylpiperidines such as pethidine (meperidine) and ketobemidone, allylprodine, prodine, propoxyphene, dextropropoxyphene, dextromoramide, bezitramide, piritramide, methadone, dipipanone, levomethadyl Acetate (LAAM), loperamide, diphenoxylate, dezocine, pentazocine, phenazocine, buprenorphine, dihydroetorphine, etorphine, butorphanol, nalbuphine, levorphanol, levomethorphan, lefetamine, meptazinol, tilidine, tramadol, tapentadol, mixtures thereof, and the like.

In yet other embodiments, the additional drug(s) is tarpentadol (a centrally acting oral analgesic having two mechanisms of action combining mu-opioid receptor agonism and norepinephrine reuptake inhibition).

In yet other embodiments, the additional drug(s) is a selective norepinephrine reuptake inhibitor, such as Atomoxetine (Strattera®), Mazindol (Mazanor®, Sanorex®), Nisoxetine (LY-94939), Reboxetine (Edronax®, Vestra®), Viloxazine (Vivalan®), mixtures thereof, and the like.

In yet other embodiments, the additional drug(s) is a benzodiazepine, such as lorazepam (Ativan®), diazepam (Valium®), clonazepam (Klonopin®), chlordiazepoxide (Librium®), alprazolam (Xanax®), temazepam (Restoril®), mixtures thereof, and the like. In other embodiments, the drug is a neuroleptic or psychotropic such as chlorpromazine (Thorazine®), haloperidol (Haldol®), risperidone (Risperdal®), olanzapine (Zyprexa@) and quetiapine (Seroque®).

In other embodiments, the additional drug(s) is an agent that treats depression and/or anxiety, for example, selective serotonin reuptake inhibitors (SSRIs) such as fluoxetine (Prozac), sertraline (Zoloft®), venlafaxine (Effexor®), citalopram (Celexa®), parocetine (Paxil), mixtures thereof, and the like (such as trazodone (Desyrel)), and/or serotonin-norepinephrine reuptake inhibitors (SNRI), such as Desvenlafaxine (Pristiq®), Duloxetine (Cymbalta®), Milnacipran (Ixel®, Savella®), Venlafaxine (Effexor®), mixtures thereof, and the like.

In yet other embodiments, the additional drug(s) is a norepinephrine-dopamine reuptake inhibitor (NDRI), such as Amineptine (Survector®), an aminoketone antidepressant such as Bupropion (Wellbutrin®, Zyban®), Dexmethylphenidate (Focalin), Methylphenidate (Ritalin®, Concerta®), Nomifensine (Merital®), a phenylpiperazine antidepressant such as nefazodone (Serzone®), a piperazinoazepine antidepressant such as mirtazapine (Remeron®), mixtures thereof, and the like.

In yet other embodiments, the additional drug(s) may be an NMDA receptor antagonist. Phencyclidine, ketamine, and dextromethorphan, are used as recreational drugs. At subanesthetic doses, however, these drugs have mild stimulant effects, and these agents have shown promise for the treatment of conditions that involve excitotoxicity, including traumatic brain injury, stroke, and neurodegenerative diseases such as Alzheimer's, Parkinson's, and Huntington's.

Additionally, the additional drug(s) may be an agent that treats neuropathic/neurogenic pain (pain that arises from nerve dysfunction and not as a result of injury, e.g., trigeminal neuralgia), such as carbamazepine, gabapentin, topiramate, zonisamide, phenytoin, desipramine, amitriptyline, imipramine, doxepin, protriptyline, pentoxifylline, and hydroxyzine.

In other embodiments, the additional drug(s) treats insomnia, such as zolpidem (Ambien®).

In other embodiments, the additional drug(s) treats fatigue. Such drugs include central nervous system stimulants such as pemoline (Cylert®) and Modafinil (Provigil®).

In yet other embodiments, the additional drug(s) treats vertigo, nausea and/or dizziness, such as meclizine (Antivert®), dimenhydrinate (36qualene36), prochlorperazine (36qualene36®), scopolamine (Transderm®) and diphenhydramine (Benadryl®).

In yet other embodiments, the drug is a serotonin-norepinephrine reuptake inhibitor (SNRI), such as Desvenlafaxine (Pristiq®), Duloxetine (Cymbalta®), Milnacipran (Ixel®, Savella®), Venlafaxine (Effexor®), mixtures thereof, and the like.

In yet other embodiments, the additional drug(s) is a tricyclic antidepressant (TCA), such as Amitriptyline (Elavil®), Butriptyline (Evadene®, Evadyn® e), Clomipramine (Anafranil®), Desipramine (Norpramin®, Pertofrane), Dosulepin (Prothiade), Doxepin (Adapin, Sinequan), Imipramine (Tofranil®), Lofepramine (Feprapax®, Gamanil®, Lomont®), Nortriptyline (Aventyl®, Nortrilen®, Pamelor®), Protriptyline (Vivacti® l), Trimipramine (Surmontil®), mixtures thereof, and the like.

In yet other embodiments, the additional drug(s) is a tetracyclic antidepressant, such as Amoxapine (Asendin®), Maprotiline (Ludiomil®), Mianserin (Tolvon®), mixtures thereof, and the like.

In yet other embodiments, the additional drug(s) is an atypical antipsychotic, such as Ziprasidone (Geodon®, Zeldox®), Nefazodone (Serzone®), and the like.

In yet other embodiments, the additional drug(s) is an anti-convulsant or anti-epileptic drug such as arylsulfonimide analogues such as Acetazolimide (Diamox)®, tricyclic iminostilbene derivatives such as carbamazepine (Tegreto®), benzodiazepines such as clonazepam (Klonopin®), clorazepate dipotassium (Tranxene®), lorazepam (Ativan®) and diazepam (Valium®), carboxylic acid derivatives such as valproic acid (Depakene®) and divalproex sodium (Depakote®), succinimide derivatives such as ethosuximide (Zarontin®), carbamate esters of 2-phenyl-1,3-propanediol such as felbamate (Felbatol®), hydantoins such as phenytoin (Dilantin®), phenytoin sodium (Dilantin®) and fosphenytoin sodium (Cerebyx®), structural analogues of GABA such as gabapentin (Neurontin®) and pregabalin (Lyrica®), phenyltriazines such as lamotrigine (Lamictal®), pyrrolidine derivatives such as levitiracetam (Keppra®), tricyclic iminostilbene derivatives such as 37qualene37pine (Trileptal), barbiturates such as Phenobarbital, desoxybarbiturates such as primidone (Mysoline®), nipecotic acid derivatives such as tiagabine hydrochloride (Gabitril®), sulfamated monosaccharides such as topiramate (Topamax®), oxazolidinedione derivatives such as trimethadione (Tridione®), and methanesulfonamides such as zonisamide (Zonigran®). Additional drugs such as Retigabine® (Valeant Pharmaceuticals), Lacosamide® (Schwarz Biosciences), and Perampanel® (Eisai) are in development as anti-epileptics and neuromodulators for other associated neurological, pain, and psychiatric conditions, and thus are further examples of potentially useful drugs in the present invention.

In yet other embodiments, the additional drug(s) is an analgesic/anti-inflammatory agent such as acetaminophen; prednisone, solumedrol, and other steroids; naproxen, aspirin, voltaren, ketoprofen, ibuprofen, nabumetone, and other NSAID's. The NSAID may be COX-1, COX-2 or mixed COX-1/COX-2 inhibitors. Examples of COX-2 inhibitors include oxicam, meloxicam, and the more selective celecoxib, rofecoxib, valdecoxib, parecoxib and etoricoxib. Further examples of corticosteroids include methylprednisolone, prednisolone, dexamethasone, and adrenocorticotrophic hormone (ACTH), corticotropin.

Additionally, the additional drug(s) may be an agent that treats neuropathic/neurogenic pain (pain that arises from nerve dysfunction and not as a result of injury, e.g., trigeminal neuralgia), such as carbamazepine, gabapentin, topiramate, zonisamide, phenytoin, desipramine, amitriptyline, imipramine, doxepin, protriptyline, pentoxifylline, and hydroxyzine, mixtures thereof, and the like.

In other embodiments, the additional drug(s) is 4-aminopyridine (4-AP; also known as Fampridine®) or a pharmaceutically acceptable and therapeutically active derivative thereof. This drug has been shown to have the ability to improve the communication between damaged nerves, which may result in increased neurological function in the treatment of conditions such as multiple sclerosis (MS). An example of another such drug is 3,4 diaminopyridine. In certain preferred embodiments, the 4-AP is included in the formulation in an amount from about 1 mg to about 40 mg, preferably about 2 to about 10 mg, and in certain embodiments most preferably about 5 mg.

In other embodiments, the additional drug(s) is useful for the treatment of Dementia/Alzheimer's disease, such as Aricept®/donepezil, Exelon®/rivastigmine, Reminyl®/Razadyne®/galantamine, and Namenda®/memantine, their naturally occurring counterparts, and mixtures thereof.

In other embodiments, the additional drug(s) is a serotonin agonist useful for the treatment of migraine, such as for example and without limitation, sumatriptan, naratriptan, eletriptan, rizatriptan, zolmitriptan, almotriptan, frovatriptan, pharmaceutically acceptable salts thereof, mixtures thereof, and derivatives thereof. Preferably the serotonin agonist is sumatriptan (3-(2-(dimethylamino)ethyl)-N-methyl-1H-indole-5-methanesulfonamide), one of its salts or derivatives. For migraine use, the additional drug(s) may further comprise an ergot alkaloid, such as for example and without limitation bromocriptine, ergocristine, ergocristinine, ergotamine, ergotaminine, ergocryptine, ergocryptinine, ergocornine, ergocorninine, ergosine, ergosinine, ergonovine, ergometrinine, dihydroergotamine, lisuride, d-lysergic acid, d-isolysergic acid, lysergol, lergotrile, metergoline, methysergide, methylergonovine pharmaceutically acceptable salts thereof, mixtures thereof, and derivatives thereof. Preferably the ergot alkaloid is ergotamine, dihydroergotamine, methysergide, salts, derivatives, active metabolites or prodrugs thereof e.g., dihydroergotamine mesylate. As used herein, the identification of an agent(s) to be delivered includes not only the ergot alkaloid per se but also its topically administrable prodrugs, active metabolites and prodrugs of the active metabolites.

In certain embodiments of the present invention, the serotonin agonist is in an amount of from about 0.5 mg to about 200 mg, preferably the serotonin agonist is in an amount of from about 0.5 mg to about 100 mg, and most preferably from about 10 mg to about 100 mg. In certain preferred embodiments, the formulations of the present invention contain sumatriptan base or a pharmaceutically acceptable salt thereof (e.g., sumatriptan succinate). When the serotonin agonist is sumatriptan or a pharmaceutically acceptable salt thereof, the amount of sumatriptan is in an amount of from about 0.5 mg to about 200 mg, preferably in an amount of from about 5 mg to about 200 mg, from about 5 mg to about 100 mg, from about 5 mg to about 50 mg, or from about 5 mg to about 25 mg, and most preferably is in an amount of 12.5 mg, 25 mg, 50 mg or 100 mg. Comparative oral doses of certain triptans are as follows: sumatriptan, 50 mg; rizatriptan, 10 mg; naratriptan, 2.5 mg; zolmitriptan, 2.5 mg; and eletriptan, 40 to 80 mg. Therefore, one skilled in the art can readily determine therapeutically equivalent doses of serotonin agonists that may be useful in the present invention.

In other embodiments, the additional drug(s) is a skeletal muscle relaxant. Useful skeletal muscle relaxants include centrally acting skeletal muscle relaxants, and are not limited to for example and without limitation, afloqulone, baclofen, botulin toxins, carisoprodol, chlormezanone, chlorphenesin carbamate, chlorzoxazone, cyclobenzaprine, clonazepam, diazepam, eperisone, idrocilamide, inaperisone, mephenesin, mephenoxalone, methocarbamol, metaxalone, mivacurium chloride, orphenadrine, phenprobamate, pridinol mesylate, quinine, tetrazepam, thiocolchicoside, tizanidine, tolperisone, pharmaceutically acceptable salts thereof, active metabolites thereof, prodrugs thereof and mixtures thereof. Preferably the skeletal muscle relaxant is tizanidine base, tizanidine hydrochloride or any pharmaceutically acceptable salts thereof, prodrugs thereof or mixtures thereof. In certain preferred embodiments where the skeletal muscle relaxant is tizanidine, the amount of tizanidine included in the formulation is from about 1 mg to about 10 mg, preferably about 5 mg. One skilled in the art can readily determine therapeutically equivalent doses of other skeletal muscle relaxants such as those mentioned herein that may be useful in the present invention.

In certain embodiments, the topical formulation is used to treat insomnia, and a therapeutically effective amount of a cannabinoid (e.g., CBD) and a therapeutically effective amount of melatonin. The therapeutically effective amount of melatonin may be, for example, from about 0.05 mg to about 30 mg, and in certain preferred embodiments about 5 mg.

In certain embodiments, the topical formulation is used to treat Parkinson's disease, tremors and/or dystonia. In such embodiments, the topical formulation comprises a therapeutically effective amount of a cannabinoid (e.g., CBD) and a therapeutically effective amount of apomorphine. The therapeutically effective amount of apomorphine may be, for example, from about 0.25 mg to about 4 mg, and in certain preferred embodiments about 2 mg.

In certain embodiments, the topical formulation is used to treat ADD/ADHD and/or Tourette's syndrome. In such embodiments, the topical formulation comprises a therapeutically effective amount of a cannabinoid (e.g., CBD) and a therapeutically effective amount of phentermine. The therapeutically effective amount of phentermine may be, for example, from about 5 mg to about 40 mg, and in certain preferred embodiments about 10 mg.

In certain embodiments, the topical formulation is used to treat anxiety and panic attacks, or mood disorders. In such embodiments, the topical formulation may comprise a therapeutically effective amount of a cannabinoid (e.g., CBD) and a therapeutically effective amount of an antidepressant (such as milnacipran or another serotonin-norepinephrin reuptake inhibitor (SNRI). The therapeutically effective amount of milnacipran may be, for example, from about 12.5 mg to about 100 mg, and in certain preferred embodiments about 25 mg.

In certain embodiments, the topical formulation is used to treat diabetic peripheral neuropathy (DPN) and other peripheral neuropathic conditions. In such embodiments, the topical formulation may comprise a therapeutically effective amount of a cannabinoid (e.g., CBD) and a therapeutically effective amount of 4-aminopyridine or a therapeutically active derivative thereof. The therapeutically effective amount of 4-aminopyridine may be, for example, from about 5 mg to about 40 mg, and in certain preferred embodiments about 10 mg.

In certain embodiments, the topical formulation is used to treat spasticity and/or spasms. In such embodiments, the topical formulation may comprise a therapeutically effective amount of a cannabinoid (e.g., CBD) and a therapeutically effective amount a dopamine agonist (e.g., apomorphine). The therapeutically effective amount of dopamine agonist may be, for example, from about 0.25 mg to about 4 mg, and in certain preferred embodiments about 2 mg. One skilled in the art can readily determine therapeutically equivalent doses of other dopamine agonists such as those mentioned herein that may be useful in the present invention.

In certain embodiments, the topical formulation is used to great migraine and/or tension headache. In such embodiments, the topical formulation may comprise a therapeutically effective amount of a cannabinoid (e.g., CBD) and a therapeutically effective amount of a dopamine agonist such as sumatriptan and (optionally) a skeletal muscle relaxant (e.g., tizanidine). The therapeutically effective amount of skeletal muscle relaxant may be, for example, from about 0.25 mg to about 50 mg, and in certain preferred embodiments about 5 mg. One skilled in the art can readily determine therapeutically equivalent doses of other skeletal muscle relaxants such as those mentioned herein that may be useful in the present invention.

Formulations

All currently approved therapies for the conditions described above reach the central nervous system through the systemic circulation. Cerebral blood flow to brainstem structures is through the posterior circulation, via the vertebral and basilar arteries and their branches. In view of the undesirable side-effects associated with this form of drug delivery to the brain, it makes sense that targeted regional delivery to the brainstem is sought. Topical delivery of currently used drugs compounded in an appropriate "dermal penetration enhancer" and applied in cream/gel form or as a sustained-release patch at the posterior cervical region (back of the neck) at the hairline is such a method. Lipoderm® is an example of an effective commercially available compounding medium. However, one skilled in the art will recognize that topical carriers meeting the specific chemical requirements of an individual drug can be formulated for maximum efficiency in topical delivery.

The formulations of the present invention are prepared such that the drug(s) may be delivered acutely as single dose applications as cream/gel/ointment or as a sustained release topical patch, depending on the condition treated and associated symptom complex in the individual patient. The critical point, again, is in the location of the application: at the back of neck at the hair-line for access to posterior cervical afferents with free nerve endings under the surface of the skin. Through feedback connections with vagal and trigeminal afferent systems, this results in ultimate effect on brainstem structures.

By virtue of the method of treatment described herein, the disease state/condition to be treated may be treated much faster and more effectively than such prior art modes of administration.

In certain embodiments of the present invention, the method of treating a human patient comprises applying a topical formulation which comprises a drug suitable for topical administration, which is useful for the treatment of a disease state or condition treatable via the topical brainstem afferent stimulation (de-afferentation) drug therapy described herein.

The methods of the present invention may also, if desired, involve pre-treatment of the skin with an enhancer to increase the permeability of the skin to the applied drug. The methods of the present invention may include pre-treatment or "prepping" of the skin area with a substance that opens up the skin pores. Additionally, the methods of the present invention may include, if desired, pre-treatment or "prepping" of the skin with an alcohol swab or the like to rid the area of dirt, make-up, oil, and the like, prior to application of the drug.

In certain embodiments, the topical formulation of the present invention comprises a drug in an amount which is therapeutically effective when administered topically at the at the back of neck at the hair-line for access to posterior cervical afferents with free nerve endings under the surface of the skin, but which provides a plasma concentration which is sub-therapeutic if orally administered.

In certain embodiments, by applying the formulation of the present invention comprising a dose of drug at the back of neck at the hair-line for access to posterior cervical afferents with free nerve endings under the surface of the skin, it may be possible for the use of lower doses of drug or faster relief of the headache than if applied to the trunk or limbs of a human patient, and the lower plasma levels of drug which result from lower doses may thereby reduce unwanted side effects of the drug.

The topical formulations of the present invention (e.g., ointment, gel, cream, or the like), must be suitable for topical administration of a drug, i.e., must contain pharmaceutically acceptable excipients compatible with application to the skin tissue, and may optionally contain a sufficient amount of an enhancer composition as described hereinafter.

In certain embodiments, in addition to the drug (e.g., cannabinoid drug(s)), the topical formulations and/or transdermal therapeutic systems of the present invention may include at least one adjuvant such as a penetration enhancer, anti-oxidant, stabilizer, carrier, or vehicle. Additionally or alternatively, the present invention may include the application of electric current (iontophoresis) for enhancing permeation of the cannabinoid drug(s).

Suitable penetration enhancers useful in the formulations of the present invention include but are not limited to isostearic acid, octanoic acid, oleic acid, oleyl alcohol, lauryl alcohol, ethyl oleate, isopropyl myristate, butyl stearate, methyl laurate, diisopropyl adipate, glyceryl monolaurate, tetrahydrofurfuryl alcohol polyethylene glycol ether, polyethylene glycol, propylene glycol, 2-(2-ethoxyethoxy)ethanol, diethylene glycol monomethyl ether, diethylene glycol monoethyl ether, alkylaryl ethers of polyethylene oxide, polyethylene oxide monomethyl ethers, polyethylene oxide dimethyl ethers, dimethyl sulfoxide, glycerol, ethyl acetate, acetoacetic ester, N-alkylpyrrolidone, and terpenes.

In certain embodiments, the topical formulations comprising a drug in an ointment, gel, cream or the like, will typically contain on the order of about 0.001 to about 80% by weight, preferably 0.01 wt. % to 50 wt. % drug (i.e., cannabinoid drug(s) plus optional additional drugs as described herein), and about 0 wt. % to about 50.0 wt. %, preferably from about 1 wt. % to about 30 wt. % of a permeation enhancer composition, with the remainder of the composition comprising a carrier or vehicle. In certain preferred embodiments, the drug is included in a cream or gel or ointment in a concentration of, e.g., 1 mg drug/ml of carrier (e.g., Lipoderm). However, it is to be understood that one skilled in the art can increase the amount of carrier or change the carrier and maintain or improve efficacy of the topical formulation for TRNA therapy. In certain preferred embodiments, the drug is applied as a unit dose at the back of the neck or at the BONATH in immediate release form (e.g., cream, ointment or gel) for acute treatment with a cannabinoid drug as would be beneficial to a human patient. In such instances, it is preferred that the concentration of cannabinoid drug(s) included in the unit dose is from about 1 mg to about 100 mg, based on cannabidiol, or an therapeutically equivalent amount of another cannabinoid drug(s) as described herein. In certain preferred embodiments, a unit dose of cannabinoid (e.g., CBD) is from about 5 mg to about 50 mg or from about 7.5 mg to about 30 mg. This may be administered in a topical cream, ointment, gel or the like. For example, the topical formulation may be administered as a unit dose in an amount from about 0.5 g to about 1 g at a cannabinoid (e.g., CBD) concentration from about 0.1% to about 5% (or more).

In certain embodiments, the topical formulations comprising a cannabinoid drug(s) with or without additional drugs (collectively referred to herein as "drug(s)") in an ointment, gel, cream or the like, will typically contain on the order of about 0.001 to about 80% by weight, preferably 0.01 wt. % to 50 wt. % drug(s) or from about 0.5% to about 5% drug(s); and about 0 wt. % to about 50.0 wt. %, preferably from about 1 wt. % to about 30 wt. % of a permeation enhancer composition, with the remainder of the composition comprising a carrier or vehicle. In certain preferred embodiments, the drug comprises CBD and is included in a cream or gel or ointment in a concentration of, e.g., 1 mg drug/ml of carrier (e.g., Lipoderm). However, it is to be understood that one skilled in the art can increase the amount of carrier or change the carrier and maintain or improve efficacy of the topical formulation for TRNA therapy.

Suitable (optional) permeation enhancers may also be included in the formulations. Such enhancers include, but are not limited to, dimethylsulfoxide (DMSO), N,N-dimethylacetamide (DMA), decylmethylsulfoxide (C10 MSO), polyethylene glycol monolaurate (PEGML), propylene glycol (PG), PGML, glycerol monolaurate (GML), lecithin, the 1-substituted azacycloheptan-2-ones, particularly 1-n-dodecylcyclazacycloheptan-2-one (available under the trademark Azone® from Whitby Research Incorporated, Richmond, Va.), alcohols, and the like. The permeation enhancer may also be a vegetable oil as described in U.S. Pat. No. 5,229,130 to Sharma. Such oils include, for example, safflower oil, cotton seed oil and corn oil.

Additional optional enhancers for use in conjunction with the present invention are lipophilic compounds having the formula [RCOO]n R', wherein n is 1 or 2 and R is C1-C16 alkyl optionally substituted with 1 or 2 hydroxyl groups, and R' is hydrogen or C1-C16 alkyl optionally substituted with 1 or 2 hydroxyl groups. Within this group, a first subset of compounds are represented by the formula [CH3 (CH 2)m COO]n R' in which m is an integer in the range of 8 to 16, n is 1 or 2, and R' is a lower alkyl (C1-C3) residue that is either unsubstituted or substituted with one or two hydroxyl groups. Preferred enhancers within this group include an ester which is a lower alkyl (C1-C3) laurate (i.e., m is 10 and n is 1) such as "PGML". It will be appreciated by those skilled in the art that the commercially available material sold as "PGML" is typically although not necessarily a mixture of propylene glycol monolaurate itself, propylene glycol dilaurate, and either propylene glycol, methyl laurate, or both. Thus, the terms "PGML" or "propylene glycol monolaurate" as used herein are intended to encompass both the pure compound as well as the mixture that is typically obtained commercially. Also within this group is a second subset of compounds, namely, esters of fatty alcohols represented by the formula CH3 (CH2)m-O—CO—CHR1R2, in which R1 and R2 are independently hydrogen, hydroxyl, or lower alkyl (C1-C3), and m is as above. Particularly preferred enhancers within this group are lauryl lactate and myristyl lactate. In addition, a third subset of compounds within this group are analogous fatty acids, i.e., acids having the structural formula CH3 (CH2)m COOH where m is as above. A particularly preferred acid is lauric acid.

Other optional enhancer compositions are wherein a lipophilic compound as just described, particularly PGML is combined with a hydrophilic compound, such as a C2-C6 alkanediol. One preferred hydrophilic enhancer within this group is 1,3-butanediol. Such enhancer compositions are described in detail in PCT Publication No. WO 95/05137, published Feb. 23, 1995, herein incorporated by reference. Another hydrophilic enhancer that may be included in these compositions is an ether selected from the group consisting of diethylene glycol monoethyl ether (Transcutol) and diethylene glycol monomethyl ether. Such enhancer compositions are described in detail in U.S. Pat. Nos. 5,053,227 and 5,059,426 to Chiang et al., the disclosures of which are herein incorporated by reference.

Other optional enhancer compositions may include mixture or combinations of any of the aforementioned enhancers, and the like.

One preferred topical formulation comprises the cannabinoid drug(s) in oil, together with a suitable amount of a penetration enhancer, dimethyl sulfoxide and a base. For example, such a formulation may include the CBD oil, and about 3 ml dimethyl sulfoxide in 30 g of base. The CBD can be incorporated at a concentration of, e.g., from about 0.5% to about 5% of the topical formulation in a preferred embodiment, and most preferably from about 1.5% to about 3% in a certain embodiment. The dose of such a formulation would be, e.g., from about 0.5 g to about 1 g applied topically on the back of the neck of the human patient.

U.S. Patent Publication No. 20080112895, hereby incorporated by reference, describes a room temperature stable aqueous cannabinoid formulation comprising an effective amount of a cannabinoid in a semi-aqueous solution buffered to a pH of about 5-1, the solution comprising water and an effective amount of an organic cosolvent to maintain the physical stability of the formulation, which may be incorporated into a pharmaceutically acceptable carrier.

In certain embodiments the topical formulation may include at least one water-insoluble, pharmacologically approved, alkyl cellulose or hydroxyalkyl cellulose, and the like. Alkyl cellulose or hydroxyalkyl cellulose polymers for use in this invention include ethyl cellulose, propyl cellulose, butyl cellulose, cellulose acetate, hydroxypropyl cellulose, hydroxybutyl cellulose, and ethylhydroxyethyl cellulose, alone or in combination. In addition, a plasticizer or a cross linking agent may be used to modify the polymer's characteristics. For example, esters such as dibutyl or diethyl phthalate, amides such as diethyldiphenyl urea, vegetable oils, fatty acids and alcohols such as acid oleic and myristyl may be used in combination with the cellulose derivative.

In certain embodiments, the topical formulation may further include hydrocarbons such as liquid paraffin, qualene, solid paraffin, microcrystalline wax, etc.; higher aliphatic alcohols such as cetyl alcohol, hexadecyl, alcohol, stearyl alcohol, oleyl alcohol, etc.; esters of higher fatty acids with higher alcohols such as beeswax, etc.; esters of higher fatty acids with lower alcohols such as isopropyl myristate, isopropyl palmitate, etc.; vegetable oils, modified vegetable oils, hydrous lanolin and its derivative, squalene, 47qualene; higher fatty acids such as palmitic acid, stearic acid, etc. and the like.

In certain embodiments, the topical formulation may further include emulsifiers and dispersing agents which include, for example, anionic, cationic and nonionic surfactants. Nonionic surfactants are preferred because of their low levels of irritation to skin. Typical of nonionic surfactants are fatty acid monoglycerides such as glyceryl monostearate, etc.; sorbitan fatty acid esters such as sorbitan monolaurate, etc.; sucrose fatty acid esters; polyoxyethylene fatty acid esters such as polyoxyethylene stearate, etc.; and polyoxyethylene higher alcohol ethers such as polyoxyethylene cetyl ether, polyoxyethylene oleyl ether, etc.

In certain preferred embodiments, the topical TRNA formulation is aqueous-based.

In certain embodiments of the present invention, the topical formulation may include a gelling agent such as methylcellulose, ethylcellulose, hydroxyethylcellulose, hydroxypropyl-cellulose, hydroxypropylmethylcellulose, carboxymethylcellulose, carbomer, and the like. Examples of pharmaceutical compositions which rely upon an aqueous gel composition as a vehicle for the application of a drug are U.S. Pat. Nos. 4,883,660; 4,767,619; 4,511,563; 4,861,760; and 5,318,780, the disclosures of which are herein incorporated by reference.

The topical formulation may further include one or more preservatives, stabilizers, or anti-oxidants.

Examples of preservatives that may be used in a formulation according to the present invention include, but are not limited to, bacteriostatic compounds and other preservatives suitable for topical administration including various alcohols, sorbic acid and salts and derivatives thereof, ethylenediamine, monothioglycerol, and thimerosal.

Examples of stabilizers that may be present in a formulation according to the present invention include pH buffers suitable for topical administration, complexing agents, chelating agents and the like.

Examples of anti-oxidants that may be used in a formulation according to the present invention include ascorbic acid and its derivatives, e.g., ascorbyl palmitate, as well as butylated hydroxyanisole, butylated hydroxytoluene, sodium bisulfite, sodium metabisulfite, and others.

Other adjuvants that may be included in the drug formulation include carriers, tackifiers, pigments, dyes, and other additives that do not adversely affect the mechanical or adhesive properties of the formulation.

"Carriers" or "vehicles" as used herein refer to carrier materials suitable for transdermal drug administration, and include any such materials known in the art, e.g., any liquid, gel, emulsion, solvent, liquid diluent, solubilizer, or the like, which is nontoxic and which does not interact with other components of the composition in a deleterious manner. The term "carrier" or "vehicle" as used herein may also refer to stabilizers, crystallization inhibitors, dispersing agents or other types of additives useful for facilitating transdermal drug delivery. It will be appreciated that compounds classified as "vehicles" or "carriers" may sometimes act as permeation enhancers, and vice versa, and, accordingly, these two classes of chemical compounds or compositions may sometimes overlap.

Carrier materials suitable for use in the instant compositions include those well-known for use in the cosmetic and medical arts as bases for ointments, lotions, salves, aerosols, suppositories and the like. Suitable carriers include, for example, water, liquid alcohols, liquid glycols, liquid polyalkylene glycols, liquid esters, liquid amides, liquid protein hydrolysates, liquid alkylated protein hydrolysates, liquid lanolin and lanolin derivatives, and like materials commonly employed in cosmetic and medicinal compositions. Other suitable carriers herein include for example alcohols, including both monohydric and polyhydric alcohols, e.g., ethanol, isopropanol, glycerol, sorbitol, 2-methoxyethanol, diethyleneglycol, ethylene glycol, hexyleneglycol, mannitol, and propylene glycol; ethers such as diethyl or dipropyl ether; polyethylene glycols and methoxypolyoxyethylenes (carbowaxes having molecular weight ranging from 200 to 20,000); polyoxyethylene glycerols, polyoxyethylene sorbitols, stearoyl diacetin, and the like. In certain preferred embodiments, the carrier is an aqueous based cannabidiol cream is produced using Lipoderm® as the carrier. Lipoderm®/LIP is a whitish cream with no smell, commercially marketed compounding agent (from PCCA, Pharmaceutical Compounding Centers of America) having the following ingredients: Ethoxydiglycol, Water (Aqua), Glycerin, C12-isAlkyl Benzoate, Glyceryl Stearate, Dimethicone, Cetearyl Alcohol, Cetearyl Glucoside, Polyacrylamide, Cetyl Alcohol, Magnesium Aluminum Silicate, Xanthan Gum, Aloe Vera (Aloe Barbadensis), Tocopheryl Acetate (Vitamin E Acetate), *Prunus* Amygadalus *Amara* (Bitter Almond) Kernel Oil, *Vitis Vinifera* (Grape) Seed Extract, *Triticum Vulgare* (Wheat) Germ Oil, Retinyl Palmitate (Vitamin A Palmitate), Ascorbyl Palmitate (Vitamin C Palmitate), Pro-Lipo Multi-emulsion Liposomic System, Tetrasodium EDTA, Phenoxyethanol, and Sodium Hydroxymethylglycinate.

In certain embodiments of the invention, part or all of the dose of cannabinoid drug(s) may be encapsulated within liposomes. For example, U.S. Patent Publication No. 2015/0302148, hereby incorporated by reference, describes fast-acting liposomal and micelle formulations of cannabinoids which are prepared by (a) dissolving one or more cannabinoids or cannabinoid analogues in ethanol to obtain an ethanol cannabinoid solution; (b) adding a phospholipid to the ethanol cannabinoid solution to obtain an ethanol-phospholipid cannabinoid solution; (c) injecting the ethanol-phospholipid cannabinoid solution into distilled water to obtain a liposomal cannabinoid suspension; and (d) removing the ethanol from the liposomal cannabinoid suspension, thereby producing a stable liposomal suspension of one or more cannabinoids or cannabinoid analogue. In certain embodiments, the method further comprises the step of adding sodium alginate to the liposomal suspension of one or more cannabinoids or cannabinoid analogues to obtain an alginate liposomal cannabinoid suspension that has a final alginate concentration of 2% w/v, followed by the addition of calcium chloride to the alginate liposomal cannabinoid suspension to obtain a calcium alginate-encapsulated liposomal cannabinoid suspension. This suspension is then cold-pressed and air-dried to remove the water so as to obtain a dry cannabinoid powder. The dry cannabinoid powder can be re-suspended in citrate buffer to obtain an aqueous cannabinoid solution. The amount of cannabinoid or cannabinoid analogue in the aqueous cannabinoid solution is greater than 40%.

In certain preferred embodiments of the present invention where it is desired that the drug is administered chronically, the formulations of the present invention may be formulated as a transdermal delivery system (also referred to herein as a transdermal therapeutic system) such as a transdermal patch, a transdermal plaster, a transdermal disc, iontophoretic transdermal device, or the like. Such formulations are recognized by those skilled in the art as providing a release of drug and absorption into the skin of the patient in a sustained manner over an extended period of time (e.g., 1-7 days). In such embodiments of the present invention, the transdermal delivery system comprises, e.g., a cannabinoid drug(s) contained in a reservoir or a matrix, and an adhesive which allows the transdermal patch to adhere to the skin, allowing the passage of the active agent from the transdermal patch through the skin of the patient. In preferred embodiments, the transdermal patch is applied topically at the back of the neck so as to achieve topical regional neuro-affective therapy ("TRNA THERAPY") as described herein. In embodiments in which the drug is contained in a transdermal patch, it is contemplated that the drug will be absorbed more slowly and the transdermal patch will provide a sustained release and prolonged therapeutic effect, as compared, e.g., to a cream or ointment intended to provide an immediate release of the drug and rapid onset of the TRNA therapy. In such embodiments, the dose of cannabinoid drug(s) may be that which is sufficient to provide a therapeutically effective dose to the back of the neck (e.g., non-systemic dose) over the course of e.g., from about 1, 2, 3, 4, 5, 6 or 7 days. In certain embodiments, the dose of cannabinoid drug(s) contained in the transdermal delivery system is from about 0.5 mg to about 1000 mg. In certain preferred embodiments, the dose of the cannabinoid drug is from about 1 mg to about 100 mg. In certain preferred embodiments in which the cannabinoid drug is cannabidiol, the dosage is from about 8 mg to about 80 mg, and in certain preferred embodiments, about 40 mg. As there are only a finite number of receptors on the skin, once these receptors are bound, the rest of the active drug is contained in the (e.g., topical) preparation is superfluous. Therefore, there is no possibility of "over-dosing," only of extra drug of potentially irritating the skin surface. Accordingly, in preferred embodiments, the methods and formulations of the present invention provide reduced side effects as compared to a systemic administration of the same drug.

In certain embodiments, the transdermal delivery devices, as well as other transdermal delivery systems in accordance with the invention can be made in the form of an article such as a tape, a patch, a sheet, a dressing or any other form known to those skilled in the art. Generally the device will be in the form of a patch of a size suitable to deliver a unit dose of serotonin agonist through the skin. The drug may be introduced into a transdermal therapeutic system in different forms (solid, in solution, in dispersion); it may also be microencapsulated.

In certain embodiments the present invention provides a transdermal therapeutic system comprising a cannabinoid drug(s) in an amount that would provide sub-therapeutic plasma levels if administered orally, but is therapeutically effective when administered via transdermal delivery at the back of the neck.

A transdermal delivery system for use in accordance with the present invention can also be constructed with an enhancer composition and other ingredients described hereinabove with respect to the topical formulation. Preferably, the transdermal delivery system is formulated for the prolonged delivery of the cannabinoid drug(s). The targeted skin flux for delivery of the cannabinoid drug(s) can be achieved by adjusting vehicle composition and vehicle loading, as well as by adjusting the surface area through which the compositions are administered to skin.

In certain preferred embodiments, the transdermal delivery system (e.g., patch) is formulated to deliver from about 1 mg to about 800 mg of the cannabinoid drug(s) per each 24 hours through the skin of the patient, based on cannabidiol (CBD), or a therapeutically equivalent amount of a suitable alternative cannabinoid(s) as described herein. In embodiments in which the transdermal delivery system is intended to be applied to the skin at the back of the neck for multiple days, the transdermal delivery system (e.g., patch) is formulated to provide a flux rate over the useful life of the system such that a similar amount (e.g., mean dose) is delivered on a daily basis until the system is removed and replaced with a fresh system.

The transdermal delivery system used in the present invention may be prepared, for example, in accordance with U.S. Pat. Nos. 5,069,909; 4,806,341; 5,026,556; 4,588,580; 5,016,652; 3,598,122; 4,144,317; 4,201,211; 4,262,003; and 4,379,454; all of which are incorporated herein by reference.

Additionally, the transdermal delivery system used in the present invention may be in accordance with U.S. Pat. No. 6,689,379, hereby incorporated by reference, which system is a matrix or reservoir system which comprises at least one pharmaceutical active agent and a pressure-sensitive adhesive comprising a polyacrylate polymer, wherein said polyacrylate polymer has a polyacrylate backbone containing monomer units selected from the group consisting of acrylic acid, methacrylic acid and ester derivatives of acrylic or methacrylic acid, and said monomer units comprise at least 50% (w/w) relative to a mean polymer mass of said polyacrylate polymer, a total amount of monomers selected from the group consisting of non-esterified acrylic acid and non-esterified methacrylic acid is 0.5 to 10.0% (w/w) relative to the mean polymer mass of said polyacrylate polymer, and the carboxyl groups of said non-esterified acrylic and methacrylic acid monomers are present stoichiometrically at 5 to 100% in the form of alkali salts or alkaline-earth salts, said salts being reaction products of a neutralization reaction of an alcoholic solution of an alkaline hydroxide or an alkaline-earth hydroxide with said acrylate polymer(s), or of a neutralization reaction of an alkali alcoholate or an alkaline-earth alcoholate with said acrylate polymer(s).

In certain embodiments, the dosage form can be a transdermal patch comprising a laminated composite for administering the drug (e.g., cannabinoid drug(s)) to an individual transdermally comprising: (a) a polymer backing layer that is substantially impermeable to the cannabinoid drug(s); and (b) a reservoir layer comprising a water-base acrylate pressure-sensitive adhesive, 1 to 12% by weight serotonin agonist and 2 to 25% by weight of a permeation enhancer comprising propylene glycol monolaurate in combination with capric acid or oleic acid, wherein the skin contact area of the composite is 10 to 100 cm2.

The dosage form can be a transdermal patch comprising (a) a polar solvent material selected from the group consisting of C3-C4 diols, C3-C6 triols, and mixtures thereof; and (b) a polar lipid material selected from the group consisting of fatty alcohol esters, fatty acid esters, and mixtures thereof; wherein said polar solvent material and said polar lipid material are present in a weight ratio of solvent material:lipid material of from about 60:40 to about 99:1.

In certain embodiments, the dosage form also comprises a transdermal plaster comprising: (1) a film layer which comprises a polyester film of 0.5 to 4.9 microns thickness, 8 to 85 g/mm strength, respectively in the two directions intersecting substantially at right angles, 30 to 150% elongation, in the two directions intersecting substantially at right angles and an elongation ratio of A to B of 1.0 to 5.0, wherein A and B represent data in two directions intersecting at right angles, and A is greater than B, and wherein said polyester film comprises 0.01 to 1.0% by weight, based on the total weight of said polyester film, of solid fine particles in which (a) the average particle size is 0.001 to 3.0 microns, and (b) the average particle size is substantially not more than 1.5 times the thickness of said polyester film; and (2) an adhesive layer (a) which is composed of an adhesive containing said serotonin agonist and further wherein said adhesive layer (a) is laminated on said film layer over the surface in a 2 to 60 microns thickness.

In certain embodiments, the dosage form can be a transdermal disc comprising: (a) a backing layer which is substantially impervious to the cannabinoid drug(s); and (b) a polymer matrix disc layer which is adhered to said backing layer and which has microdispersed therein said serotonin agonist, said polymer being bioacceptable and permitting said serotonin agonist to be transmitted for transdermal absorption, the cannabinoid drug(s) being stable in said polymer matrix.

In certain embodiments, the topical formulation or transdermal therapeutic system may further comprise another active ingredient in combination with the first drug (e.g., as previously described herein).

The present invention is contemplated to encompass all transdermal formulations, e.g., the technologies described above, with the inclusion of the cannabinoid drug(s), such that the administration of a drug useful for treatment of disease state or condition in humans via topical brainstem afferent stimulation (de-afferentation) therapy via topical administration. Therefore, modifications of the invention via, e.g., the choice and/or amount of drug are considered to be obvious variations of this disclosure and within the scope of the appended claims.

The present invention also contemplates the administration of the cannabinoid drug (s) directly below the skin to affect direct brainstem afferent stimulation to the free nerve endings under the epidermis. Such administration may be effected as an injection (e.g., subcutaneous injection) or implantation of the drug in immediate release or sustained release form. It will be appreciated by those skilled in the art that providing the drug in sustained release form and administering it in a suitable form below the skin may provide benefits, including less frequent administration (e.g., in chronic therapy).

In certain embodiments of the invention, the cannabinoid drug(s) can be formulated for controlled or sustained delivery at the back of the neck via incorporation into a biocompatible and implantable polymer which can be in the form of microparticles or an implantable insert, or a liquid that forms a gel or colloid or a semi-solid after injection (thereby encapsulating the drug and allowing it to be released in a prolonged and controlled manner at the desired site). For chronic conditions (e.g., Parkinson's) or desired prolonged effect, it is contemplated that a drug depot or reservoir may be created under the skin at the back of the neck, which then provides a sustained release of the drug in proximity to the desired nerve endings and which may be replenished or replaced at the end of the dosing interval. It is contemplated that such administrations of the drug may provide a prolonged therapeutic effect for at least about 3 days, preferably at least about 7 days, or longer. Such formulations may be administered in certain embodiments as, for example, a subcutaneous depot.

Implants are placed subcutaneously by making an incision in the skin and forcing the implants between the skin and the muscle. At the end of their use, if not dissolved, these implants are surgically removed. U.S. Pat. No. 4,244,949, hereby incorporated by reference, describes an implant which has an outer matrix of an inert plastic such as polytetrafluoroethylene resin. Examples of this type of implantable therapeutic system are Progestasert IUD and Ocusert system. It is contemplated that such systems can be appropriately modified by one skilled in the art for use in conjunction with the present invention. A commercially available product, Norplant®, which is an implant having a core containing levonorgestrel as the active substance, and where the core it surrounded by a membrane of a silicone elastomer of poly(dimethylsiloxane) (PDMS). Another preparation of this kind is Jadelle®, in which the core is a poly(dimethylsiloxane) based matrix with levonorgestrel dispersed therein. The membrane is an elastomer made from PDMS and silica filler, which, besides giving necessary strength properties to the membrane, also retards the permeation of the active agent through the membrane. U.S. Pat. No. 3,854,480, hereby incorporated by reference, describes a drug delivery device, e.g. an implant, for releasing a drug at a controlled rate for a prolonged period of time. The device has a core of a matrix in which the drug is dispersed. The core is surrounded by a membrane that is insoluble in body fluids. The core matrix as well as the membrane are permeable to the drug by diffusion. The materials of the core and the membrane are chosen so that the drug diffuses through the membrane at a lesser rate than through the core matrix. Thus, the membrane controls the release rate of the drug. As a suitable polymer for the core matrix is mentioned poly(dimethylsiloxane) (PDMS), and as suitable polymers for the membrane are mentioned polyethylene and a copolymer of ethylene and vinyl acetate (EVA). It is contemplated that the above systems may be adapted by one skilled in the art to deliver the cannabinoid drug(s) in accordance with the present invention.

One device which may be adapted by one skilled in the art for use in the present invention is described in U.S. Pat. No. 5,968,542 (Tipton), hereby incorporated by reference, which describes a high viscosity liquid controlled delivery system as a medical or surgical device is provided that includes: (i) a non-polymeric, non-water soluble liquid carrier material (HVLCM) of viscosity of at least 5,000 Cp at 37° C. that does not crystallize neat under ambient or physiological conditions; and, optionally, (ii) a substance to be delivered.

The pharmaceutical compositions suitable for injectable use in accordance with this invention include sterile aqueous solutions or dispersions and sterile powders or lypholysates for the extemporaneous preparation of sterile injectable solutions or dispersions. The dosage forms must be sterile and it must be stable under the conditions of manufacture and storage. The carrier for injectable formulations is typically water but can also include ethanol, a polyol (for example, glycerol, propylene glycol and liquid polyethylene glycol), mixtures thereof, and vegetable oil.

Injectable formulations used in the present invention can also be formulated as injectable prolonged release formulations in which the active compound is combined with one or more natural or synthetic biodegradable or biodispersible polymers such as carbohydrates, including starches, gums and etherified or esterified cellulosic derivatives, polyethers, polyesters, polyvinyl alcohols, gelatins, or alginates. Such dosage formulations can be prepared for example in the form of microsphere suspensions, gels, or shaped polymer matrix implants that are well-known in the art for their function as "depot-type" drug delivery systems that provide prolonged release of the biologically active components. Such compositions can be prepared using art-recognized formulation techniques and designed for any of a wide variety of drug release profiles.

One example of a useful formulation which may be used in the methods of the present invention for providing a prolonged duration of action is described in U.S. Pat. No. 7,332,503 (Wikstrom, et al.), hereby incorporated by reference. Therein, apomorphine derivatives and the physiologically acceptable salts thereof as well as formulations thereof are described which provide a prolonged duration of action. The apomorphine pro-drugs can be suspended (as a neat oil or as crystals, or dissolved in a suitable and pharmaceutically acceptable solvent (e.g. water, ethanol, DMSO, i-PrOH or benzylbenzoate)) in a pharmaceutically acceptable depot oil (e.g. viscoleo, sesame oil or olive oil) and injected subcutaneously or intramuscularly with a syringe or a "pen injector". Alternatively, these drugs may, in a suitable composition and with a suitable vehicle (penetration enhancer), be applied to a patch for transdermal administration. The composition could include also a local anesthetic (e.g. lidocaine) to avoid injection pain, in particular at intramuscular injections. In one embodiment, the composition is in the form of a patch or an ointment for transdermal administration. The patch or ointment preferably also comprises stabilizers, solubilizers and permeation activators to facilitate the passage of the active principle through the skin. In another preferred embodiment, the composition is in the form of a depot preparation for subcutaneous or intramuscular administration comprising the cannabinoid drug(s) dissolved or suspended in an oil. In certain embodiments, in addition to the apomorphine derivative, the formulation further contains a local anesthetic. The formulations described in the '503 patent can be modified as understood by one skilled in the art to contain other active drugs as described herein for use at the back of the neck, e.g., BONATH.

An injectable depot formulation is a dosage form, which is generally intended to have a therapeutic activity for 2 to 4 weeks after administration (e.g. in sesame oil). In order to maintain effective drug plasma levels the dosage form should release the drug at a more or less constant rate during the desired dosing interval. The difference between such prior art depots and depots used in the present invention is that the in accordance with the present invention, the drug is not needed to be absorbed into the systemic circulation.

A suitable form of depot preparation is the subcutaneous or intramuscular administration of an oil solution and/or oil suspension of a lipophilic drug. This gives a slow transport over the oil-biofluid interface and a slow dissolution in the biophase. Thus, when the drug is dissolved in a polar solvent (e.g. oils), which is non-miscible with the aqueous biological fluids, the drug has to be transported over the oil/water interface. When the oil/water partition coefficient is high, the transport will be slow. For very lipophilic drugs, the release from the oil phase may last for up to several weeks. The use of depot preparations such as those described herein may be used to deliver the drugs described herein at the back of the neck, e.g., BONATH.

The maximum volume of an oil solution/suspension to be injected intramuscularly or subcutaneously is 2-4 Ml. This is feasible for the preparations of the cannabinoid drug formulations of the present invention. For example, the cannabinoid drug(s) may be dissolved or dispersed in 1 Ml of an oil (sesame oil, Viscoleo or another approved oil) and the mixture gently heated (max 50° C.) shaken in a test tube shaker and ultrasonicated for a short time (minutes) until the mixture becomes a homogeneous solution or suspension. If necessary, the cannabinoid drug(s) may first be dissolved in 50-300 al DMSO, water, t-BuOH, PEG, benzylbenzoate, or another suitable and approved solvent or mixtures thereof, before adding the oil to a total volume of 1 Ml.

Another example of a polymeric drug delivery system which may be adapted for use in the present invention by one skilled in the art is described in U.S. Pat. No. 5,601,835 (Sabel, et al.), hereby incorporated by reference, which describes a polymeric drug delivery system for delivery of any substance to the central nervous system. The delivery system is preferably implanted in the central nervous system for delivery of the drug directly to the central nervous system. These implantable devices can be used, for example, to achieve continuous delivery of dopamine, which cannot pass the blood brain barrier, directly into the brain for an extended time period. The implantable devices display controlled, "zero-order" release kinetics, a life time of a minimum of several weeks or months even when the devices contain water soluble, low molecular weight compounds, biocompatibility, and relative non-invasiveness. The polymeric devices are said to be applicable in the treatment of a variety of central nervous system disorders including Parkinson's disease, Alzheimer's dementia, Huntington's disease, epilepsy, trauma, stroke, depression and other types of neurological and psychiatric illnesses, and one skilled in the art can adapt that drug delivery system for delivering the drugs contemplated herein at the back of the neck, e.g., BONATH.

Yet another example of a system that may be adapted for use in the present invention is described in U.S. Pat. No. 5,601,835 (Sabel, et al.), hereby incorporated by reference, wherein an active compound is encapsulated within a polymer to form a polymeric device, the device formed of a biocompatible polymer that is plastically deformable selected from the group consisting of ethylene vinyl acetate, polyurethanes, polystyrenes, polyamide, polyacrylamide, and combinations thereof having a non-porous polymer coating thereon with one or more openings, with limited water sorptivity and slight permeability to the passage of small, aqueous-soluble molecules, wherein said compound is linearly released (e.g., zero order release) from said polymeric device over a sustained period of time of at least 65 days at a predetermined level and rate when implanted in a patient at a specific site within the central nervous system where the compound is released directly into the central nervous system and the device remains essentially intact throughout the release period. The delivery device is a two-phase system that is manufactured using standard techniques such as blending, mixing or the equivalent thereof, following selection of the biologically active material to be delivered and an appropriate polymer for formation of the matrix. The general method of solvent casting as disclosed by Siegel and Langer, "Controlled release of polypeptides and other macromolecules", Pharmaceutical Research 1, 2-10 (1984), is modified so that drug is dispersed within the devices to create channels and pores to the surface for release of the drug at the desired rate. Where appropriate, a coating impermeable to the drug is placed over a portion of the drug containing polymer matrix to further regulate the rate of release. One skilled in the art can adapt that drug delivery system for delivering the drugs contemplated herein at the back of the neck, e.g., BONATH.

Yet another formulation which may used to deliver the drug as set forth in the present invention at the back of the neck, e.g., BONATH, is described in U.S. Pat. No. 7,314,636 (Caseres et al.), hereby incorporated by reference, which describes injectable implants comprising glycolic acid and bio-compatible/bio-absorbable polymeric particles containing a polymer of lactic acid. The particles are small enough to be injected through a needle but large enough to avoid engulfment by macrophages. The injectables of this invention may be in a pre-activated solid form or an activated form (e.g., injectable suspension or emulsion).

It is further contemplated that the system described in U.S. Pat. No. 6,586,006 (Roser, et al.), hereby incorporated by reference, can be adapted by one skilled in the art for use in the present invention for delivery of drugs at the back of the neck, e.g., BONATH. Therein are described delivery systems suitable for delivery of bioactive materials to subcutaneous and intradermal, intramuscular, intravenous tissue, the delivery system being sized and shaped for penetrating the epidermis. The delivery systems comprise a vitreous vehicle loaded with the guest substance and capable of releasing the guest substance in situ at various controlled rates. Subdermal implantable therapeutic systems have also been formulated for slow release of certain pharmaceutical agents for extended periods of time such as months or years. A well-known example is Norplant® for delivery of steroid hormones.

In membrane permeation-type controlled drug delivery, the drug is encapsulated within a compartment that is enclosed by a rate-limiting polymeric membrane. The drug reservoir may contain either drug particles or a dispersion (or solution) of solid drug in a liquid or a matrix type dispersing medium. The polymeric membrane may be fabricated from a homogeneous or a heterogeneous nonporous polymeric material or a microporous or semipermeable membrane. The encapsulation of the drug reservoir inside the polymeric membrane may be accomplished by molding, encapsulation, microencapsulation, or other techniques. The implants release drugs by dissolution of the drug in the inner core and slow diffusion across the outer matrix. The drug release from this type of implantable therapeutic system should be relatively constant and is largely dependent on the dissolution rate of the drug in the polymeric membrane or the diffusion rate across or a microporous or semipermeable membrane. The inner core may substantially dissolve over time; however, in devices currently in use, the outer matrix does not dissolve.

Other implantable therapeutic systems involve matrix diffusion-type controlled drug delivery. The drug reservoir is formed by the homogeneous dispersion of drug particles throughout a lipophilic or hydrophilic polymer matrix. The dispersion of drug particles in the polymer matrix may be accomplished by blending the drug with a viscous liquid polymer or a semisolid polymer at room temperature, followed by cross-linking of the polymer, or by mixing the drug particles with a melted polymer at an elevated temperature. It can also be fabricated by dissolving the drug particles and/or the polymer in an organic solvent followed by mixing and evaporation of the solvent in a mold at an elevated temperature or under vacuum. The rate of drug release from this type of delivery device is not constant. Examples of this type of implantable therapeutic system are the contraceptive vaginal ring and Compudose implant. PCT/GB 90/00497 describes slow release glassy systems for formation of implantable devices. The described implants are bioabsorbable and need not be surgically removed. One skilled in the art can adapt these drug delivery systems for delivering the drugs contemplated herein at the back of the neck, e.g., BONATH.

In microreservoir dissolution-controlled drug delivery, the drug reservoir, which is a suspension of drug particles in an aqueous solution of a water-miscible polymer, forms a homogeneous dispersion of a multitude of discrete, unleachable, microscopic drug reservoirs in a polymer matrix. The microdispersion may be generated by using a high-energy-dispersing technique. Release of the drug from this type of drug delivery device follows either an interfacial partition or a matrix diffusion-controlled process. An example of this type of drug delivery device is the Syncro-Mate-C Implant.

Yet another formulation which may be adapted by one skilled in the art for use in the present invention is described in U.S. Pat. No. 6,576,263 (Truong, et al.), hereby incorporated by reference, which describes a preformed object for delivering an active agent for a subject, the preformed object including cross-linked protein, and methods of making and using.

Yet another formulation which may be adapted by one skilled in the art for use in the present invention is described in U.S. Pat. No. 6,287,588 (Shih, et al.), hereby incorporated by reference, which describes a composition and method for releasing a bio-active agent or a drug within a biological environment in a controlled manner. The composition is a dual phase polymeric agent-delivery composition comprising a continuous biocompatible gel phase, a discontinuous particulate phase comprising defined microparticles and an agent to be delivered. A microparticle containing a bio-active agent is releasably entrained within a biocompatible polymeric gel matrix. The bio-active agent release may be contained in the microparticle phase alone or in both the microparticles and the gel matrix. The release of the agent is prolonged over a period of time, and the delivery may be modulated and/or controlled. In addition, a second agent may be loaded in some of the microparticles and/or the gel matrix.

Yet another formulation which may be adapted by one skilled in the art for use in the present invention is described in U.S. Pat. No. 7,364,568 (Angel, et al.), hereby incorporated by reference, which describes a transdermal transport device includes a reservoir for holding a formulation of an active principle, and a needle with a bore extending along the length of the needle from a first end of the needle to a second end of the needle. The second end is substantially aligned to a plane parallel to a body surface of a biological body when the device is placed on the body surface. The device also includes an actuator which pumps the formulation through the bore of the needle between a target area of the body and the reservoir.

In yet other embodiments of the invention, the cannabinoid drug(s) is infused into the patient at the back of the neck using technology known to be useful for infusing other drugs, such as an insulin pump. One such system, U.S. Pat. No. 7,354,420 (Steil, et al.), hereby incorporated by reference, describes a closed loop infusion system controls the rate that fluid is infused into the body of a user. The closed loop infusion system includes a sensor system, a controller, and a delivery system. The sensor system includes a sensor for monitoring a condition of the user. The sensor produces a sensor signal, which is representative of the condition of the user. The sensor signal is used to generate a controller input. The controller uses the controller input to generate commands to operate the delivery system. The delivery system infuses a liquid into the user at a rate dictated by the commands from the controller. Preferably, the sensor system monitors the glucose concentration in the body of the user, and the liquid infused by the delivery system into the body of the user includes insulin.

The present invention is contemplated to encompass all implantable or injectable formulations, e.g., the technologies described above, with the inclusion of a drug(s) (e.g., cannabinoid drug(s)(s)), such that the administration of a drug useful for treatment of disease state or condition in humans via topical brainstem afferent stimulation (de-afferentation) therapy. Therefore, modifications of the invention via, e.g., the choice and/or amount of drug are considered to be obvious variations of this disclosure and within the scope of the appended claims.

Detailed Description of Preferred Embodiments

The present invention will now be more fully described with reference to the accompanying examples. It should be understood, however, that the following description is illustrative only and should not be taken in any way as a restriction on the generality of the invention specified above.

Example 1

Topical Formulation

An aqueous based cannabidiol cream is produced using Lipoderm® as the carrier. Lipoderm®/LIP is a commercially marketed compounding agent (from PCCA, Pharmaceutical Compounding Centers of America) having the following ingredients: Ethoxydiglycol, Water (Aqua), Glycerin, $C1_2$_isAlkyl Benzoate, Glyceryl Stearate, Dimethicone, Cetearyl Alcohol, Cetearyl Glucoside, Polyacrylamide, Cetyl Alcohol, Magnesium Aluminum Silicate, Xanthan Gum, Aloe Vera (Aloe Barbadensis), Tocopheryl Acetate (Vitamin E Acetate), *Prunus* Amygadalus *Amara* (Bitter Almond) Kernel Oil, *Vitis Vinifera* (Grape) Seed Extract, *Triticum Vulgare* (Wheat) Germ Oil, Retinyl Palmitate (Vitamin A Palmitate), Ascorbyl Palmitate (Vitamin C Palmitate), Pro-Lipo Multi-emulsion Liposomic System, Tetrasodium EDTA, Phenoxyethanol, and Sodium Hydroxymethylglycinate. The concentration is 4 mg of CBD in 1ml of Lipoderm. Lipoderm is a whitish cream with no smell. The cannabinoid drug(s) are incorporated into the Lipoderm cream in the form of a CBD oil product as described herein.

Example 2

A 60 g topical formulation of CBD is prepared by incorporating 2.2 g CBD (CBD-RSHO-Clear 43.5%), 20 g Pluronic 20%, 40 g Carbomer hydroalcoholic gel and 1 ml ethyl alcohol to obtain a CBD topical formulation having a 1.6% concentration of CBD.

Example 3—Oil-Based CBD

A 30 g topical formulation of CBD is prepared by incorporating CBD oil, Dimethyl sulfoxide 3 ml and enough base for total quantity of 30 grams. The CBD is incorporated in a concentration sufficient to yield an end product having a CBD concentration of 0.75%, 1%, 1.5%, 2% and 3%. The topical formulation is in the form of a cream. The oil-based CBD includes CBD oil commercially available from CannaVest. A unit dose of the topical CBD cream is from about 0.5 to about 1 g, with respect to formulations having a CBD concentration from 1.5%-3%. After initial application, the topical CBD formulation can be applied to the back of the neck of the human patient once a day, twice a day, three times a day, or four times a day depending on the condition to be treated and its severity.

Example 4—CBD Crystalline Powder

A 60 g topical formulation of CBD is prepared utilizing CBD crystalline powder (95%+ pure CBD). The CBD is incorporated into the topical formulation of Example 2 having a CBD concentration between 0.75% to about 10% CBD.

Example 5

The following patients were treated with a topical cannabidiol (CBD) formulation administered on the back of the neck on human patients at a 40 mg dose, as more specifically described below in Table 1:

TABLE 1

| # | Patient | Presentation | Outcome |
|---|---|---|---|
| 1 | 33 y/o Haitian male with neonatal brain damage, chronic encephalopathy and seizures. | Seizures, impulsive behavior, agitation, concentration and attentional problems. On Trileptal, Seroquel, Klonopin, Diamax, and Trazodone. Came in agitated and hyperactive as he had not had afternoon meds. | 10 minutes after topical CBD, settled down playing games on the phone and did not require usual meds without which he was usually intolerable. With continued use, mother states less agitated, more compliant, and sleeping better-all issues in the past. |
| 2 | 74 y/o female in Nursing Home with severe brain damage from multiple strokes. | Sitting in wheelchair with eyes open with blank stare, unresponsive, not following commands or verbalizing, neglect of left hemibody and not moving it. On Namenda, Depakote, and Trazodone. | 10-15 minutes after nuchal topical CBD, she "woke up" in front of RN daughter who called it "a miracle" smiling, responding verbally, following simple commands using both sides of her body. |
| 3 | 75 y/o female s/p head injury from fall in bathroom 2 months prior. | Slowed cognition, inattentive, flat affect with speech hesitancy. | More spontaneous and animated, conversant, near back to premorbid feisty personality. |
| 4 | 89 y/o female s/p hit by car with head injury. | Confusion, decreased memory, feeling "foggy" in thoughts, insomnia with visual hallucinations; mumbling speech. | More alert and less "fogginess" in thinking, speech spontaneous. |
| 5 | 66 y/o physician with daytime hyper somnolence and cognitive slowing. | s/p 4 cardiac surgeries under general anesthesia within short period of time with "perfusion pump syndrome" and hypoxic encephalopathy. | "felt more alert" more spontaneous and conversant within 15 minutes. |
| 6 | 58 y/o male successful financial advisor and stock broker with closed head injury from auto accident. | Cognitive impairment documented by formal neuropsychological testing and deemed disabled, unable to return to work. On disability with persistent seizures, lethargy, cognitive slowing, on Vyvanse, Gabapentin, Vimpat, Abilify, and tramadol. | Significant improved alertness, more conversational, improved memory also noted by wife who is a pharmacist "back to prior personality". Will begin process of reducing medications. |
| 7 | 66 y/o male Parkinson's diseases × 4 years with on-off phenomena and freezing episodes. | On apomorphine, selegiline, Comtan, Neupro patch and tizanidine and experiencing 10-12 freezing episodes per day. | With one dose of 40 mg topical CBD, no episodes of freezing for over 24 hours; also more spontaneous and with improved speech. Now on CBD 2x/day. |
| 8 | 68 y/o male s/p 2 strokes with left hand weakness and incoordination. | First right brain stroke 18 months ago with recovery. Second stroke 6 weeks ago with significant impairment of the left upper extremity. | 40 mg topical CBD resulted in significant improvement in left hand function within 15 minutes; patient also more alert and conversant. Had been complaining of lethargy when he came in, which resolved. |
| 9 | 48 y/o female with neck pain and right upper extremity numbness and weakness for a week after heaving exercise. | Exam showed decreased range of motion of neck to right with moderate weakness of the right upper extremity. Pain level was 7 of 10. | After 40 mg topical CBD, improved neck range of movement and right upper extremity strength. Pain level dropped to 2 of 10. Prior insomnia improved. |
| 10 | 55 y/o female s/p intracranial aneurysm rupture. | Uncontrollable central hypertension despite numerous medications with headaches and central pain syndrome. | 20 minutes after 40 mg topical CBD, NP dropped from 220/110 to 180/100. Patient could tell difference. |
| 11 | 14 y/o male inattention, focusing problems, agitation, oppositional defiant behavior. | Neonatal birth trauma with ICU stay for week, head injury at age 5. Recent EEG showed cortical irritability and potential for seizures. | 5 minutes after 40 mg topical CBD, remarkable change noted by father and teenage sister: calm, focused, not usual fidget behavior, and with eye contact. Patient recognized himself "more calm." |
| 12 | 58 y/o male bi-polar; cognitive problems, memory lapse, poor concentration, and impulsivity. | On Depakote, trazodone, Vilibryd, and Wellbutrin with abnormal EEG suggesting cortical irritability and seizures. | 40 mg topical CBD resulted in improved clarity of thoughts, better focus, and patient was brighter and more spontaneous. |
| 13 | 92 y/o female with anxiety disorder and panic attacks. | Patient takes Ativan/Lorazepam when she has panic attacks. She was in midst of an attack when seen. | Nuchal topical CBD 40 mg aborted panic attack and reduced anxiety from 7-8 of 10 to 4 of 10 in 5 minutes. The relief persisted. Patient liked it better than lorazepam. |
| 14 | 76 y/o female with dementia since 2008. | Patient had MRI today with Xanax as pre-op for agitation. She was slumped over unresponsive as result. | After 40 mg topical CBD, patient awoke and conversed with daughter-in-law. Dementia persisted but alerted from prior state. |

TABLE 1-continued

| | | |
|---|---|---|
| 15. 84 y/o female with multiple strokes and memory problems, attentional issues. | MRI brain with numerous infarcts, EEG with disorganized background. Patient disoriented with poor memory. | Improved focus, attention and memory. More responsive and spontaneous. Prior leg pains and itching resolved as did automatisms of picking her fingers. |
| 16. 53 y/o female with confusion, unsteadiness, and heaches. | Undergoing work-up for seizures Exam remarkable for unsteady gait with inability to tandem, walk heel-to-toe without falling to the right. Also anxious and jittery. | After 40 mg topical CBD, more calm and able to walk tandem, even with heels. Unable before with bare feet. |
| 17. 66 y/o female with memory problems and high BP. | MRI brain with atrophy.. EEG with disorganized background and frontal sharps. | BP 145/80. After 40 mg topical CBD, 130/60. |
| 18. 71 y/o female s/p stroke from AVM rupture 2 years ago. | Spastic left hemiparesis with upper extremity more affected. | 10-15 minutes after topical CBD, significant improvement in left hand function: increased strength and improved fine motor movements. |
| 19. 55 y/o female s/p viral meningitis and craniotomy with seizures, neuropathic pain, and anxiety. | Anxious with burning neuropathic pain of tongue and spasms of the jaw/dystonia. | Reduced anxiety and less burning pain and spasm of jaw. |
| 20. 72 y/o female with 12 yr. Parkinson's disease with multiple meds: Sinemet, Requip, Klonopin. | Fatigued, anxious, and with choreiform dyskinesias. | More alert and spontaneous with marked reduction in dyskinesias. |
| 21. 27 y/o female s/p auto accident with certical sprain and eye convergence problems. | Dizzy, tired, with neck spasm and pain; visual convergence difficulties. | Improved range of neck, more alert, and improve visual convergence. |
| 22. 53 y/o female with MS since 2002 on Copaxone, baclofen, recent steroids. | Left spastic hemiparesis with difficulty using hand and gait problems. | Significant improvement in left hemibody spasticity with better fine motor movements of hand and improved spastic gait in 10 minutes after topical CBD. |
| 23. 48 y/o female with ADHD and anxiety. | Treatment with Vyvanse discontinued secondary to palpitations; Strattera did not work. Now with moderate anxiety and focusing problems. Smoking marijuana daily for anxiety. | 40 mg topical CBD had profound effect on both anxiety and ADHD symptoms. |
| 24. 61 y/o female with dementia. Parkinson's disease, paranoia, lethargy. | On Namenda, Abilify, Paxil, apomorphine. | Dramatic improvement in affect with increased spontaneity, improved gait and general mobility. No change in memory but more responsive. |
| 25. 80 y/o male with dementia, impulsive behavior, agitation, anxiety. | On Lamictal, Risperdal, and Seroquel with agitation and pressured speech, inappropriate comments. | More calm, less agitated, and improved thought process and speech. |
| 26. 61 y/o female with cerebral palsy, seizures, and spastic right hemiparesis. | Marked contracturing of right arm and hand with spastic scissoring gait. On Depakote, Tegretol, Valium, Rozerem, Remeron, and imipramine. | Visibly improved right upper extremity function and gait. Also noted by her long term caretaker. |
| 27. 72 y/o female with dementia, PD, hallucinations. | Disoriented, lethargic, with speech hesitancy, and cognitive dysfunction. Tremors of head and hands. Rigid unstable gait. | More alert, responsive and conversant. Tremors and gait improved. |
| 28. 59 y/o female chronic encephalopathy and seizures. | Lethargic and mumbling speech on Keppra, Lyrica, Mysoline, Zonisamide. | More alert, and responsive with improved speech. |
| 29. 73 y/o female s/p accident with cervical disc herniation, headaches, seizures. | Experiencing headache and neck pain, 8 of 10. | Pain went to 3 of 10 in 15 minutes after topical CBD. |
| 30. 80 y/o male with PD 5 yrs. | On Sinemet, Azilect with anxiety and tremors of mouth/chin and hands. | After topical CBD, improved tremors and anxiety. |
| 31. 61 y/o female with MS since 1999 on Tysabri. | Foggy, floating feelings with detachment from environment, "as when she smoked marijuana in the remote past." | More clear and improved thought process. |
| 32. 40 y/o female with cerebral palsy, chronic encephalopathy, seizures, and retardation. | Infantile affect and thought processes with severe spastic scissoring gait with no arm swing. | Visibly improved gait with arm swing, more communicative. |

Example 6

The efficacy of a topical cannabidiol formulation was studied in a human patient (53 year old female s/p resection right clival meningioma) suffering from episodic severe post-operative neuralgic head pain suffering from severe right-sided neuralgic head pain every 15-20 seconds. The patient was treated with cannabidiol 40 mg applied to the BONATH in a topical formulation. There was attenuation of associated focal EEG abnormalities. The EEG prior to treatment showed a right temporal issue (disorganized slow sharp waves). After NUCHAL administration, her EEG showed attenuation of the right temporal waves to a more normal state. The neuralgic head pain was less severe by about 50% (frequency decreased to every 2-5 minutes). The EEG improvement lasted several minutes, but the clinical benefit lasted several hours.

Example 7

The efficacy of a topical cannabidiol formulation was studied in a human patient having a remote head injury, s/p 4 craniotomies and intractable seizures. The patient was treated with cannabidiol 40 mg applied to the BONATH in a topical formulation. There was attenuation of associated focal EEG abnormalities. The EEG prior to treatment showed a right fronto-central excessive beta and sharp waves. Post-treatment, the right fast activity and sharp waves were attenuated. The right abnormalities on the EEG were further attenuated after further topical nucal treatment with 25 mg milnacipran.

Example 8

In Example 8, 34 patients having seizures, encephalopathy, and/or spasticity were treated with topical CBD at the back of the neck. The treatment comprised a dose of either 15 mg or 30 mg cannabinoid drugs, with the majority being CBD, the source of the CBD being CBD oil commercially available from CannaVest. Table 2 below provides treatment information and results.

TABLE 2

| | |
|---|---|
| 1. 9 y/o female with cerebral palsy, seizures, and chronic encephalopathy. | After one application of CBD, spasticity decreased by 80% within 15 minutes. Now on chronic use. |
| 2. 73 y/o female with hydrocephalus, gait disorder, and anxiety; s/p VP shunt | After application of CBD, improved gait with increased confidence and less anxiety. |
| 3. 21 y/o male with autism/Aspergers. Poor impulse control, racing thoughts, and anxiety. Arrested for discharging gun in a pharmacy trying to refill Xanax Rx. | After CBD, resolution of racing thoughts, less anxious and with improved impulsivity. |
| 4. 37 y/o male with mood disorder, impulse and attentional issues, and memory problems. On Lamictal and Brintellix with some control of behavior. | After CBD application, patient felt more focused, more relaxed and less agitated with reduced neck tension: felt he was in "slow motion" and not in usual activated state. |
| 5. 15 y/o male with autism; and poor impulse control, agitation, and outbursts. On Lamictal and hydroxyzine. | After treatment with CBD, noticeably calmer, less reactive and impulsive. |
| 6. 76 y/o female with MS, trigeminal neuralgia, encephalopathy, and confusion. | Improved thought processes and mental state within 10 minutes. |
| 7. 8 y/o female with complex partial seizures, attention deficit disorder. | More focused and calmer after CBD. Prior abnormal EEG improved. Lamictal discontinued as response to CBD was superior; now on daily use CBD. |
| 8. 7 y/o male with absence/petit mal seizures with episodes of detachment, drop attacks and falls. MRI brain shows a thalamic hamartoma. | On chronic use of topical CBD 2x/day with resolution of seizure episodes. |
| 9. 6 y/o male with petit mal epilepsy Rx'd Ethosuximide/Zarontin with inattention and poor school performance, bed-wetting. | Initially started on topical CBD 2x/day, now once daily with improved attention and focus with objective improved school work noted by teachers (did not know he was on CBD). Resolved enuresis. Never took Zarontin. |
| 10. 72 y/o female with strokes from anti-phospholipid syndrome, concussion, encephalopathy, and anxiety. | After CBD, improved thought processes, less anxious and with improved sense of well-being. |
| 11. 61 y/o female with MS, seizures, unsteadiness and gait problems with falls. Depression from disabilities, | After CBD application, patient felt more in control of her body with improved gait and thought processes. She felt more positive and hopeful for first time. |
| 12. 21 y/o female with Aicardi syndrome, intractable seizures, agitation, and lack of social interaction. | After treatment with CBD, noticeably more spontaneous, interactive, and talkative. After 2 months use, seizure frequency reduced 60%. Prior doses of Lamicatal and Depakote reduced. |
| 13. 21 y/o female with cerebral palsy, mental retardation and chronic encephalopathy with anxiety and social isolation. | Improved interaction with others, less agitation, and decreased anxiety. Currently using CBD 2x/day. |
| 14. 61 y/o male with chronic encephalopathy from pesticide poisoning, adrenal insufficiency, and seizures with agitation. | Topical CBD made patient more coherent and appropriate, with reduced anxiety and agitation. |

TABLE 2-continued

| | |
|---|---|
| 15. 61 y/o female s/p intracranial aneurysm rupture with chronic encephalopathy and headaches. | On chronic use of topical CBD, more focused, resolved dizziness and chronic headaches. |
| 16. 54 y/o female with severe MS with quadriparesis and spasticity all 4 extremities; on Baclofen, Klonopin, and narcotics for pain. | Severe baseline spasticity improved 70% after one treatment with topical CBD to back of neck. Now continuing daily therapy. |
| 17. 72 y/o female with MS and cervical myelopathy with gait disturbance. | After CBD, improved walking, lifting feet, and standing more erect. Also with improved mood and significantly more talkative. |
| 18. 21 y/o male with autism/Asperger's with poor impulse control, inattention, and mood disorder. | After CBD application, became relaxed in a better mood, and less impulsive. |
| 19. 74 y/o cervical injury with paralysis and spasticity all extremities, lower worse. On high doses of Baclofen, Tizanidine, and Dantrolene for spastic contracturing pain. | After one treatment with CBD, reduction in spasticity by 30% from baseline. |
| 20. 18 y/o with anxiety precipitated complex partial seizures on Tegretol. | 3 minutes after topical CBD application, anxiety reduced over 30%. Will be using daily with plans to reduce Tegretol dose. |
| 21. 79 y/o female with neck pain, PTSD, and anxiety. | PTSD symptoms improved after CBD use 2×/day; neck pain and headaches reduced 80%. |
| 22. 36 y/o female s/p auto accident with head injury and seizures. Persistent complex partial seizures 3×/day with headaches, on Topamax. | On topical CBD 2×/day without further seizures and tapering off Topamax. Headaches also relieved. |
| 23. 53 y/o female with MS of 10 years with severe spasticity and gait problems | 30% reduction in spasticity in all 4 extremities after CBD application to back of neck. Will be using topical CBD 2×/day. |
| 24. 79 y/o female with 9 months of post-op encephalopathy with amnestic dementia, inattention, social withdrawal. Intolerant of Namenda for memory due to agitation. | After single dose of topical CBD to back of neck, became alert, more sociable and interactive, and increased awareness. Will use CBD 2×/day. |
| 25. 37 y/o male with cerebral palsy, lethargy, decreased interaction and responsiveness. | After a dose of topical CBD to back of neck, became more alert, less spastic, and interactive, with increased mobility. Will use CBD 2×/day. |
| 26. 77 y/o male s/p head injury and intracranial hemorrhage with dizziness, unsteadiness, and "foggy" thinking, | 30 minutes after topical CBD to back of neck, patient noted "clear vision, improved dizziness, and better able to walk" which lasted 8 hours. Now on 3×/day. |
| 27. 87 y/o female with spasticity, peripheral neuropathy, myoclonus, and restless legs with gait disorder. | Patient was more alert and responsive after topical CBD treatment and walked better. Prescribed 2×/day. |
| 28. 60 y/o male s/p auto accident with head injury and seizures, ADHD, neck pain for surgery, bi-polar disorder came in with severe anxiety after traumatic deposition with attorneys. | One dose of topical CBD relieved anxiety and focus problems 80% and also relieved neck pain~50%. Patient will use CBD 2×/day in addition to the Namenda, Vyvanse, Vimpat, and Abilify. |
| 29. 66 y/o female with MS and gait disturbance on Baclofen and Mirapex. Symptoms began in 20's. | After one dose of topical CBD to the neck, patient's stride improved: faster and more smooth without prior hesitancy, shuffling and stiff leg character. |
| 30. 78 y/o female with extensive strokes of the cerebral hemispheres and brainstem with 3 years of gait problems, now requiring a walker. | 15 minutes after application of topical CBD to the neck, gait visibly improved: less wide-based, picking up her feet, and more smooth. Improvement noted by patient and several other observers. |
| 31. 79 y/o female with MS, peripheral neuropathy and gait disorder. | After one dose of topical CBD to the neck, patient's gait became more brisk and smooth, with less hesitancy on turns. |
| 32. 47 y/o male s/p closed head injury with seizures, concentration problems, and anxiety. | After a dose of topical CBD to the back of the neck, became more relaxed and able to focus better. Neck tension also resolved. |
| 33. 56 y/o male s/p head injury with post-concussive syndrome and PTSD: agitation and poor concentration/focus. | 10 minutes after topical CBD to back of neck, more calm and focused and at ease for the first time in a while. |
| 34. 40 y/o male with neonatal hypoxia, attentional problems, seizures/cortical irritability, insomnia. | After topical CBD application to neck, sensation of "white noise" distracting him decreased and felt more focused. Will be using it 2×/day. |

Example 9

In Example 9, 13 patients having headaches and neck pain were treated with topical CBD at the back of the neck. The treatment comprised a dose of either 15 mg or 30 mg cannabinoid drugs, with the majority being CBD, the source of the CBD being CBD oil commercially available from CannaVest. Table 3 below provides treatment information and results.

TABLE 3

| | |
|---|---|
| 1. 45 y/o female s/p auto accident with intractable headaches and neck pain. Chronic migraines since high school. | Chronic daily headaches resolved after daily CBD cream use. Remains headache free and discontinued CBD. |
| 2. 69 y/o female with head injury and subdural hematoma with severe headaches and neck pain. | Headaches and neck pain improved 30% with CBD cream to neck. |
| 3. 73 y/o female with occipital neuralgia and trigeminal neuralgia of 3 years duration. | All pain symptoms resolved after 3 weeks of daily CBD use. |
| 4. 23 y/o female with long-standing severe TMJ pain. | 50% reduction in pain and improved mobility after CBD application to the TMJ and back of neck. |
| 5. 60 y/o female with 3 months of continuous headaches, getting no relief with chronic narcotic use, | After one treatment with CBD, headache pain diminished 50% for the first time. Prescribed topical CBD to the back of neck 3×/day. |
| 6. 24 y/o female with chronic headaches, s/p sinus surgeries, and attentional problems. Daily headaches for 10 years. | Within several minutes of topical CBD application to back of neck, headache relieved over 40%; mother noted her eyes were brighter and she was less tense. After week of daily use, headache free days for first time in 10 years. |
| 7. 70 y/o male s/p head injury with post-concussive syndrome, PTSD, neck pain and headaches; on regular use hydromorhone and hydrocodone. Used CBD mist in past. | 5 minutes after topical CBD to back of neck, reduction in head and neck pain by 50% with reduced size of knot in neck. Also, more calm, less anxious, and breathing easier. |
| 8. 39 y/o female s/p auto accident with head injury, headaches, neck pain, and cognitive problems. | Headache and neck pain resolved 5-10 minutes after topical CBD. Patient continues with 2×/day use. |
| 9. 48 y/o male with 10 days of right Bell's palsy and pain in back of neck. Finished 2 courses of oral steroids. | After CBD application to back of neck and region of stylomastoid foramen, right facial weakness and decreased sensation improved 30%. Neck pain resolved. |
| 10. 89 y/o female s/p auto accident with head and neck injury with persistent neck pain with right arm pain and weakness. | Has been using topical CBD to the neck 1-2×/day with benefit for past 2 months. Injury was over 2 years ago. |
| 11. 78 y/o female RN s/p fall 1 yr. ago with persistent neck pain and decreased ROM neck to the right. MRI shows spinal stenosis and severe spondylosis. | 5 minutes after topical CBD application to the neck, pain resolve and ROM improved 80%. Will continue to use daily. |
| 12. 51 y/o female with chronic headaches, previously on narcotics and pain pump. PTSD and mood disorder. | On 2 occasions of severe headache, used topical CBD application to the neck; with pain going from 8 to 2 of 10 and from 8 to 3 within 15 minutes. Now using regularly. |
| 13. 46 y/o female with 2 months daily headaches and neck pain. MRI brain consistent with pseudotumor cerebri. | One dose of topical CBD relieved chronic headache and improved range of motion of neck. |
| 14. 54 y/o female s/p auto accident with concussion and back injury 3 years ago. MRI shows lumbar disc herniation. | Chronic back pain improved 30% within 15 minutes after topical CBD application to the lower back. |
| 15. 41 y/o female with acute back pain with radiation into thigh from lifting injury. | Pain resolved after several treatments with topical CBD to the back. |
| 16. 62 y/o female with 2 years of severe post-herpetic neuralgia/shingles. | Thoracic pain reduced 30% within 10 minutes of topical CBD application to the thoracic spin in distribution of the pain. |

Example 10

In Example 10, 16 patients having back/spine pain, fibromyalgia, and/or extremity pain were treated with topical CBD at the back of the neck. The treatment comprised a dose of either 15 mg or 30 mg cannabinoid drugs, with the majority being CBD, the source of the CBD being CBD oil commercially available from CannaVest. Table 4 below provides treatment information and results.

TABLE 4

| | |
|---|---|
| 1. 63 y/o female with fibromyalgia, chronic back pain on narcotics. | Now off narcotics and on topical CBD to the back of neck and back 3x/day; pain relief within 2 minutes of application. |
| 2. 79 y/o female with fibromyalgia, peripheral neuropathy, and lumbar radiculopathy. | Pain relief lasts several days after single applications of topical CBD. |
| 3. 80 y/o female with cervical radiculopathy and chronic neck pain. | 50% reduction in pain in 5 minutes. |
| 4. 28 y/o female with 2 years of thoracic pain. | 60% reduction in chronic pain within a few minutes; now using daily. |
| 5. Cervical and lumbar degenerative disc disease with left arm and leg pain with poor posture. | After one treatment with CBD, decreased pain allowed patient to walk better and stand more erect. |
| 6. 52 y/o male s/p shoulder surgery on narcotics with persistent pain and immobility of shoulder. | Within several minutes of topical CBD application to shoulder and back of neck, pain diminished 40% with improved mobility. |
| 7. 74 y/o male with rheumatoid arthritis, peripheral neuropathy, and knee pain after surgery. | 30-40% knee pain relief in 5 minutes. |
| 8. 38 y/o male with right hand numbness and tingling, seizures | Right hand symptoms improved after topical CBD. |
| 9. 46 y/o female with persistent right knee pain. | Significant relief in knee pain within several minutes. |
| 10. 29 y/o male with 3 month history of intractable back and left leg pain, minimally responsive to steroid dose-pack. Has been unable to sleep as result of aching leg pain. | 6 of 10 left lower extremity pain reduced to 2/10 after 10 minutes with improved strength in left leg. |
| 11. 73 y/o female with long history of fibromyalgia, back pain, and peripheral neuropathy on Tramadol and Lyrica. | Topical CBD to the lower back provided pain relief better than Tramadol. |
| 12. 73 y/o male with lumbar spinal stenosis and neurogenic claudication. | Topical CBD to the lower back resulted in improved mobility and back pain relief within 10 minutes. |
| 13. 59 y/o female with 2 weeks of neck pain and immobility turning neck to right. MRI shows severe osteoarthritis of C1-2. | Within 15 minutes of topical CBD application to neck, improved range of motion and diminished pain. |
| 14. 54 y/o female s/p auto accident with concussion and back injury 3 years ago. MRI shows lumbar disc herniation. | Chronic back pain improved 30% within 15 minutes after topical CBD application to the lower back. |
| 15. 41 y/o female with acute back pain with radiation into thigh from lifting injury. | Pain resolved after several treatments with topical CBD to the back. |
| 16. 62 y/o female with 2 years of severe post-herpetic neuralgia/shingles. | Thoracic pain reduced 30% within 10 minutes of topical CBD application to the thoracic spine in distribution of the pain. |

Example 11

In Example 11, 6 patients having Parkinson's disease, tremors, or movement disorders were treated with topical CBD at the back of the neck. The treatment comprised a dose of either 15 mg or 30 mg cannabinoid drugs, with the majority being CBD, the source of the CBD being CBD oil commercially available from CannaVest. Table 5 below provides treatment information and results.

TABLE 5

| | |
|---|---|
| 1. 74 y/o female with long-term Parkinson's and tremors. | On topical CBD 3x/day, 50% decrease in tremors with less anxiety. |
| 2. 42 y/o female 4 yrs. Intractable left hemi-facial spasms s/p numerous Botox injections and different meds. | Facial twitching improved after 5 minutes; now using 3x/day. |
| 3. 68 y/o male with long history of familial/essential tremors. | Tremors improved 50% after 2 months use. |
| 4. 78 y/o female RN with life-long head tremors unresponsive to prior therapies | Head tremors improved 80% in 15 minutes after one application of topical CBD to back of neck. Will use daily. |
| 5. 77 y/o male, retired dentist with tremors, memory loss, and strokes. | Handwriting sample and alertness improved 10 minutes after topical CBD 3% application to the back of neck. |
| 6. 85 y/o male with strokes and Parkinson's disease with gait problems. On Sinemet and Azilect. | 10 minutes after topical CBD application to the back of neck, visible improvement in fluidity of gait with resolved festination/small steppage. |

Example 12

In Example 12, 19 patients having acute and chronic neurological and psychiatric conditions were treated with topical CBD at the back of the neck. The treatment comprised a dose of either 15 mg or 30 mg cannabinoid drugs, with the majority being CBD, the source of the CBD being CBD crystalline powder oil commercially available from CannaVest. Table 6 below provides treatment information and results.

TABLE 6

| | |
|---|---|
| 1. 65 y/o male with chronic neck, back, and leg pain on narcotics. | After one application of 1% CBD to neck and back, pain in previous areas decreased additional 30% from prior baseline. |
| 2. 62 y/o female with anxiety and mood disorder. | After application of 1% CBD to back of neck, visibly improved mood and less anxiety. Became "giggly." |
| 3. 78 y/o male with lumbar degenerative disc disease with left leg weakness | After application of 1% CBD to lower back, improved strength of left leg and resolved back pain. |
| 4. 28 y/o female with post-concussive syndrome, with lethargy, cognitive dysfunction and abnormal EEG. | 1% CBD application to back of neck improved EEG disorganization and patient became more alert and spontaneous. |
| 5. 55 y/o male s/p remote stroke with spastic right hemiparesis and expressive aphasia. | Within several minutes of 1% topical CBD application to back of neck and right forearm, spasticity improved with better movement of affected extremity. |
| 6. 24 y/o female with neck and back pain. | Pain and pressure went down 50% within 1 minute of applying 1% topical CBD to neck and back. |
| 7. 61 y/o female with long history of neck and back pain, headaches on narcotics and using 3% oil-based CBD topical cream. | 1% CBD application to back of neck improved pain within three minutes. Stated worked better than oil-based CBD she had been using. |
| 8. 29 y/o male with anxiety and left shoulder pain, smokes marijuana daily for relief of symptoms. | 1% topical CBD to neck and left shoulder reduced anxiety and decreased shoulder pain 20% within a few minutes. |
| 9. 81 y/o female with cognitive dysfunction and back pain. | Applied 0.75% topical CBD to neck and 1% to back with patient feeling more alert and responsive, back pain diminished. |
| 10. 20 y/o male with frontal head injury, agitation, and hallucinations of oil-based CBD topical cream, Lamictal. | 1.5% powdered topical CBD cream had more pronounced effect on anxiety and agitation. |
| 11. 24 y/o female s/p auto accident with neck tension and pain, | 1.5% topical CBD reduced neck tension and pain, improved range of motion. |
| 12. 72 y/o female with severe back and lower extremity neuropathic pain, | 2% topical CBD cream to lower back relieved back and lower extremity neuropathic pain. |
| 13. 80 y/o female with Parkinson's disease and tremors of head and left upper extremity. | 1% topical CBD applied to back of neck resulted in less anxiety, reduced tremors and improved gait with arm swing. |
| 14. 87 y/o female with cervical spondylosis, tremors of left hand. | Topical CBD 1% to back of neck improved range of motion and reduced tremors. |
| 15. 56 y/o male s/p head injury with cognitive problems, focus issues, mood swings. | 1% topical CBD to neck resulted in improved focus, clearer thinking, and reduced anxiety. |
| 16. 84 y/o female with multi-infarct state, dementia, and agitation with anxiety. | 1% topical CBD cream to back of neck improved agitation and patient became more cooperative. |
| 17. 42 y/o female with neck tension, pain, and headaches. | 2% topical CBD cream to back of neck relieved neck pain and tension from 8 of 10 to 2 in few minutes. |
| 18. 58 y/o female s/p numerous facial plastic surgeries with neuropathic pain over left eye brow. | 1.5% topical CBD cream to the left eye brow and back of neck reduced anxiety and relieved neuropathic pain. Had been using oil based CBD cream. |
| 19. 67 y/o female with strokes, s/p concussion, with anxiety and cognitive problems. | Had been using 3% topical oil-based CBD cream. 1.5% powdered CBD cream further relieved anxiety and improved demeanor. |

Example 13

Figure 2:
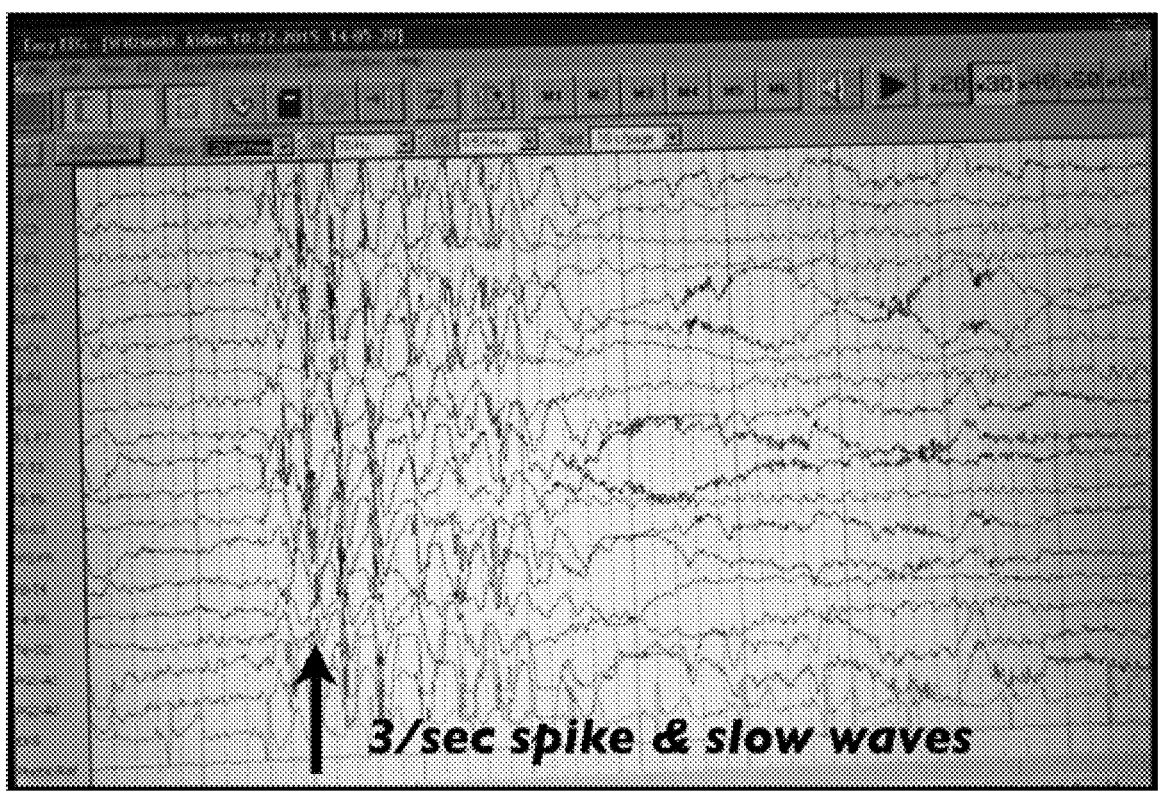
FIG. 2 is an EEG showing a baseline EEG of the patient of Example 13.

In Example 13, 6 year old male suffering from a cerebellar posterior fossa cyst, generalized seizure manifesting as standing and staring and unresponsive was treating in accordance with the present invention. FIG. 2 is an EEG showing a baseline EEG of the patient of Example 13. It revealed findings consistent with absent seizures, i.e., three per second spike and slow wave with generalized complexes. Previously, ethosuximide had been recommended for treatment, but the parents were reluctant to have the patient on a systemic convulsant therapy in view of the potential side effects. The patient was treated with a 2% CBD cream to the nuchal (back of the neck) region twice a day. After two weeks, the dosage regimen was changed to one application per day.

At the two week check-up, the patient was bright, awake, alert, oriented and nonfocal. The doctor was told that the patient was no long bed wetting, and significant improvement was noted by the patient's teachers (who had not been told that he was on a medication). His reading levels had increased two levels, and he was more focused and paying attention and his nomework time was much easier. No seizures were noted.

Figure 3:
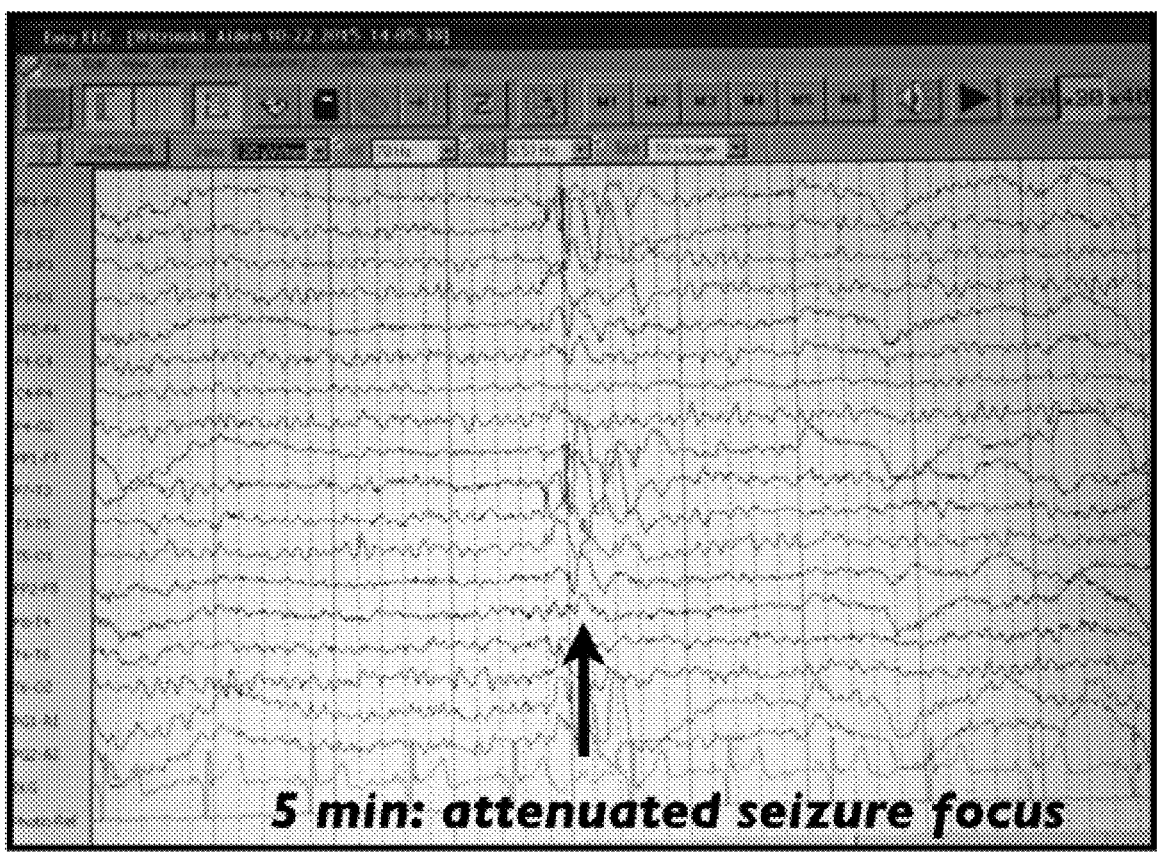
FIG. 3 is a post-treatment EEG (i.e., after application of a topical unit dose of cannabinoid drugs) of the patient of Example 13 at 5 minutes after the start of therapy.
Figure 4:
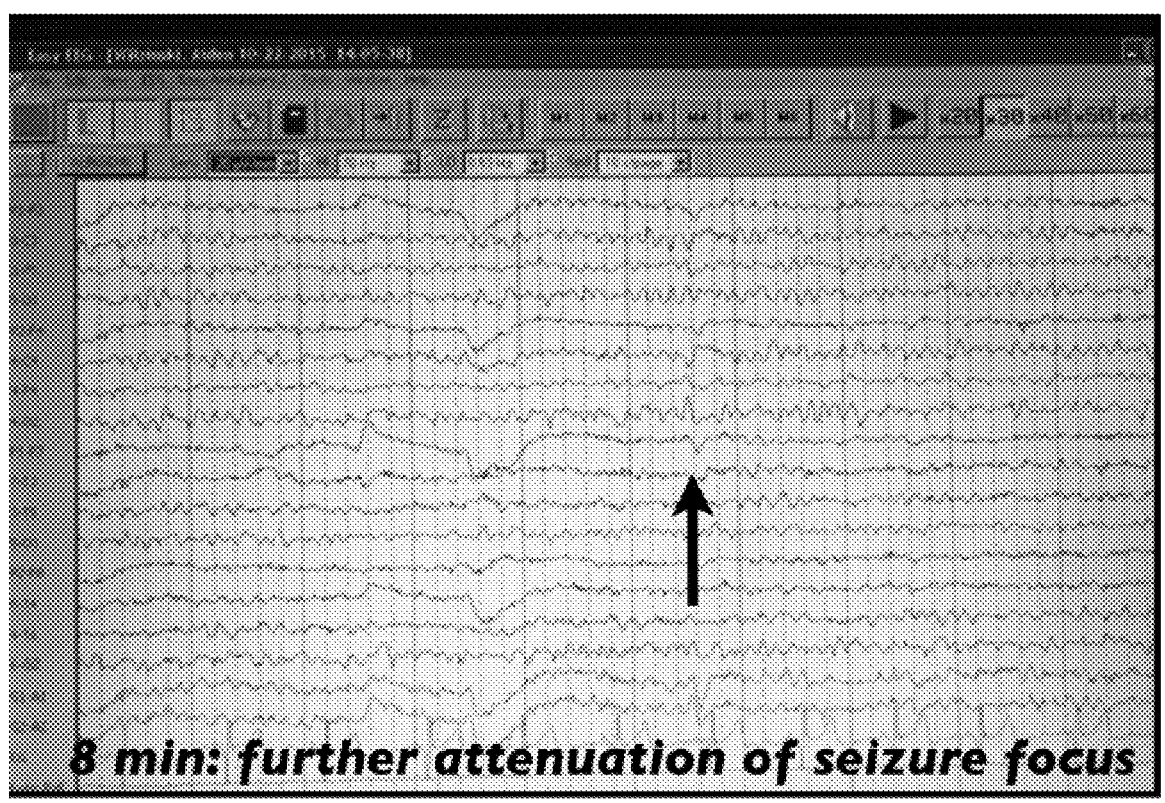
FIG. 4 is a post-treatment EEG (i.e., after application of a topical unit dose of cannabinoid drugs) of the patient of Example 13 at and 8 minutes after the start of therapy.

FIG. 3 is an EEG showing an EEG post-treatment (i.e., after application of a topical unit dose of cannabinoid drugs) of the patient of Example 13 at 5 minutes after the start of therapy. It showed attenuated seizure focus. FIG. 4 is an EEG showing the EEG post-treatment (i.e., after application of a topical unit dose of cannabinoid drugs) of the patient of Example 13 at 8 minutes after the start of therapy. It showed a further attenuation of seizure focus as compared to the EEG shown in FIG. 3.

Example 14

Figure 5:
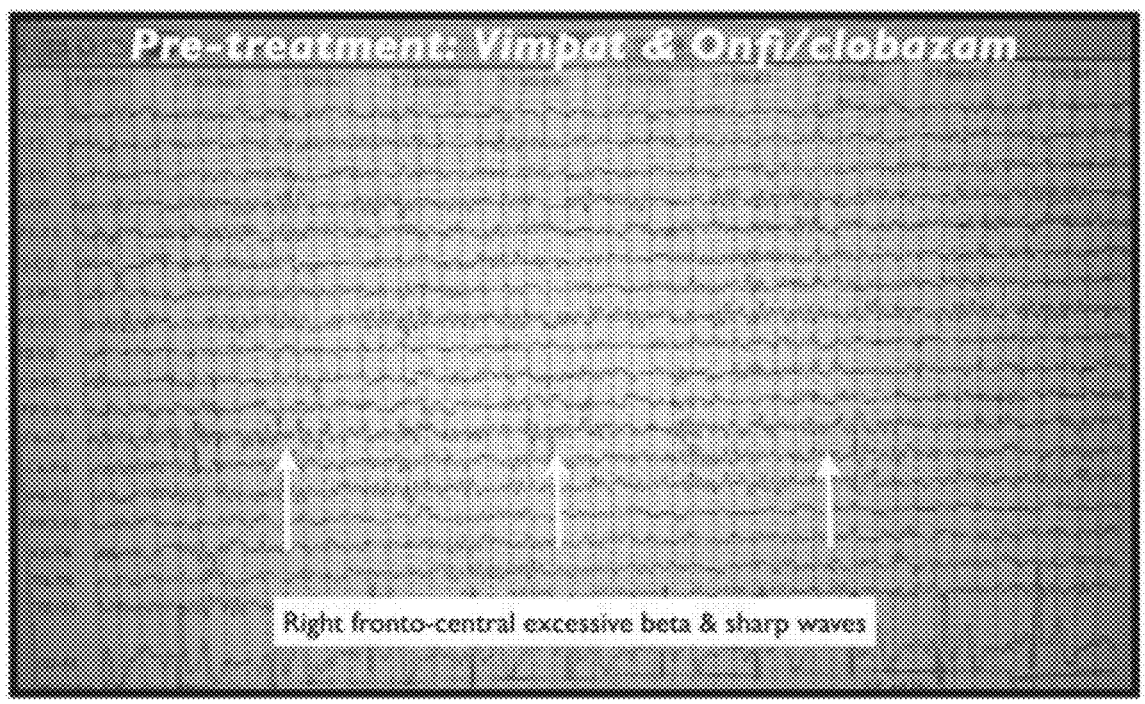
FIG. 5 is a pre-treatment EEG of the patient of Example 14 showing right fronto-central excessive beta and sharp waves.

In Example 14, a 24 year old male patient had a head injury at age 14 when he was run over by a truck. He presented with seizures (intractable complex partial seizures with secondary generalization; episodes of encephalopathy for 24 hours thereafter). As shown in FIG. 5, an EEG taken at initial examination (treatment with Vimpat and Onfi/clobazam only) showed right fronto-central excessive beta and sharp waves. He had had 5 craniotomies, and previously had been treated with Dilantin, Carbatrol, Keppra, Lamictal, and Depakote. His current medications were Vimpat and Onfi (clobazam).

Figure 6:
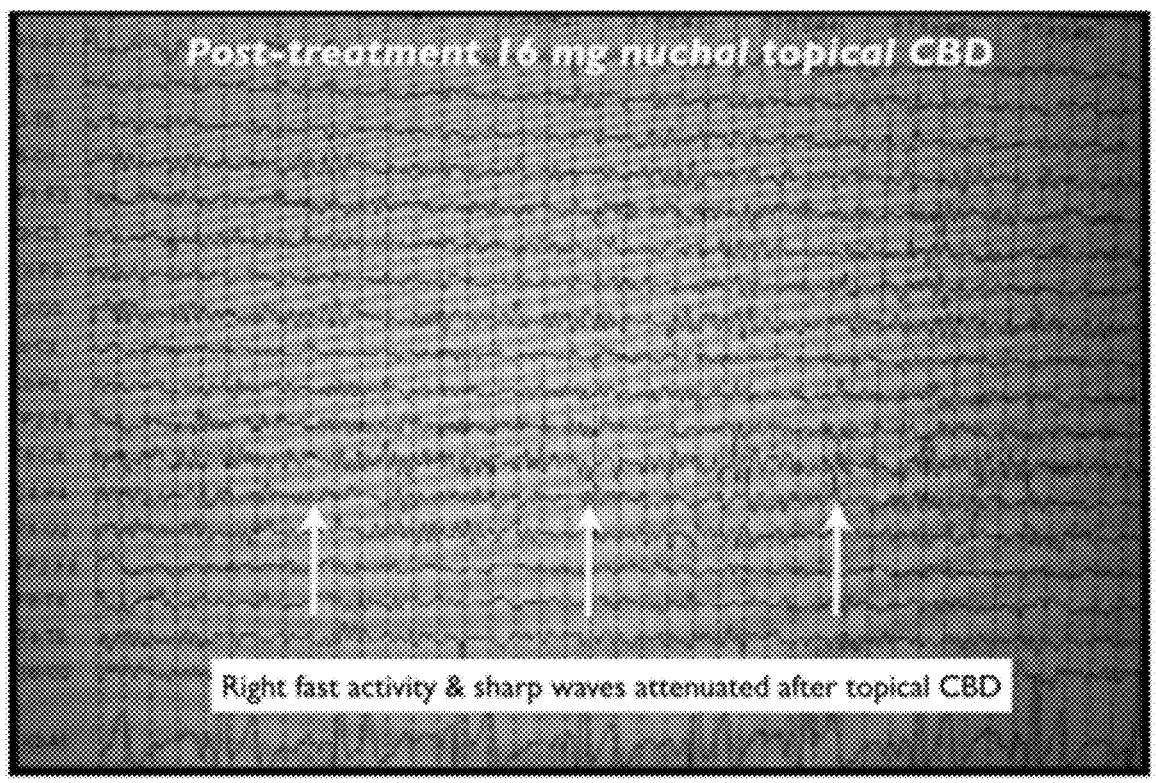
FIG. 6 is a post-treatment EEG of the patient of Example 14 showing right fast activity and sharp waves attenuated.

The patient was treated with 1 g of 1.6% CBD cream to the nuchal (back of the neck) region twice a day. At his one year follow-up examination, the patient was seizure-free. A follow-up EEG taken at that time (FIG. 6) post-treatment with the 16 mg nuchal topical CBD administration twice daily showed right fast activity and sharp waves attenuated. The follow-up EEG showed improvement: he was no longer showing seizure potential. The patient remained on Vimpat, and his dose of Onfi was reduced by half. At the time of patent filing, the patient was on continuous use of topical CBD for 20 months and remained seizure-free since June 2014.

Example 15

Figure 7:
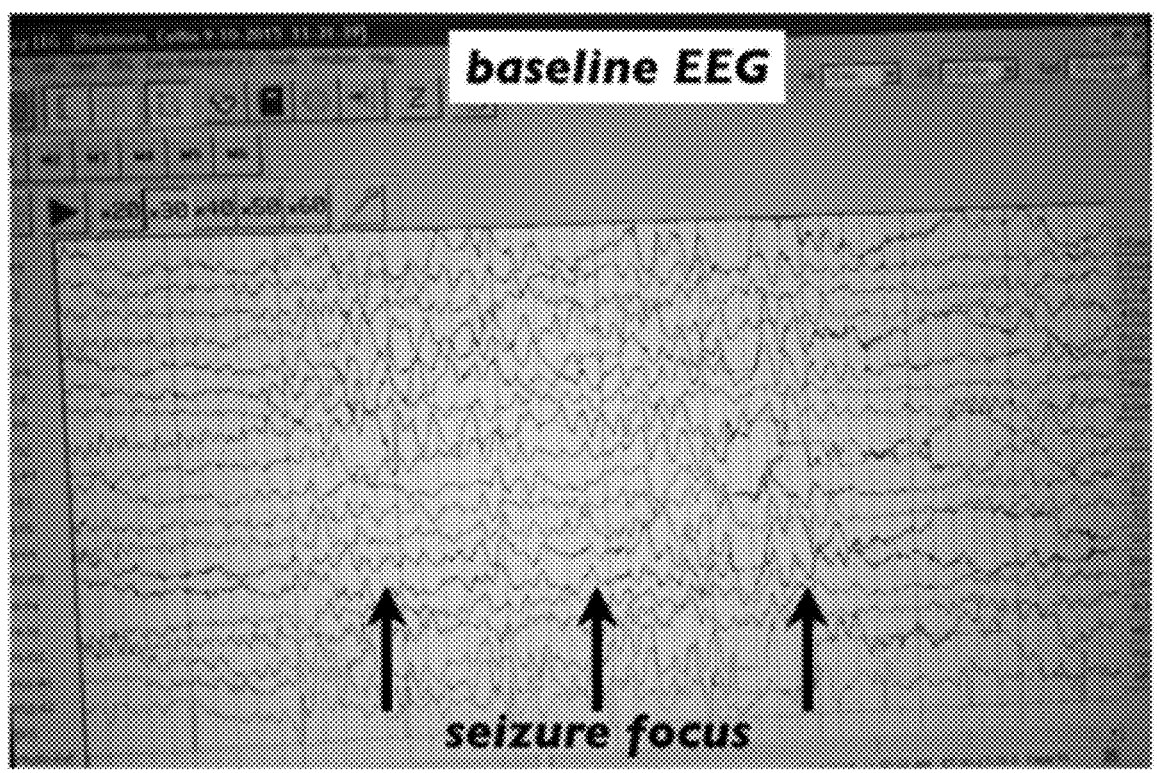
FIG. 7 is a pre-treatment EEG of the patient of Example 15 showing seizure focus.

In Example 15, a 16 year old male patient presented with autism and generalized seizures. He was uncontrolled on Lamictal, Depakote, Keppra, Zonegran, ethosuximide/Zarontin. When examined, he presented with seizures about every 2 weeks on Banzel, Onfi, and Topamax as antiepileptics. FIG. 7 is a baseline EEG taken at the initial examination, showing seizure focus, showing generalized slowing and disorganization with left frontal sharp waves and paroxysms of sharp waves and spikes.

Figure 8:
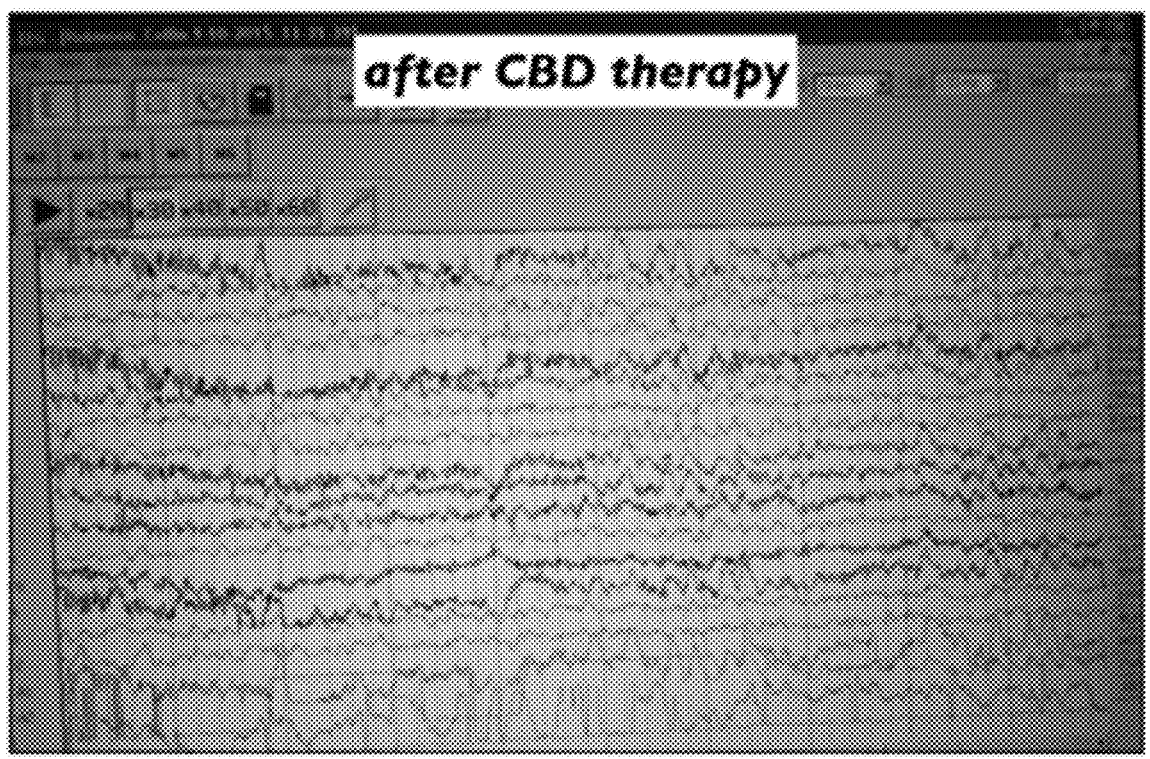
FIG. 8 is a post-treatment EEG of the patient of Example 15 showing right fast activity and sharp waves attenuated.

The patient was treated with 1 g of 2% CBD cream to the nuchal (back of the neck). Within one minute of CBD application, there was improvement in the EEG background without previous burst activity (see FIG. 8, which shows right fast activity and sharp waves attenuated). Clinically, the patient became more alert and interactive. He continued therapy with the topical CBD cream to the nuchal region twice daily, and the Topamax was tapered off, resulting in added overall improved encephalopathy. Seizure frequency also was reduced, but the patient still had behavioral issues remaining.

Example 16

Figure 9:
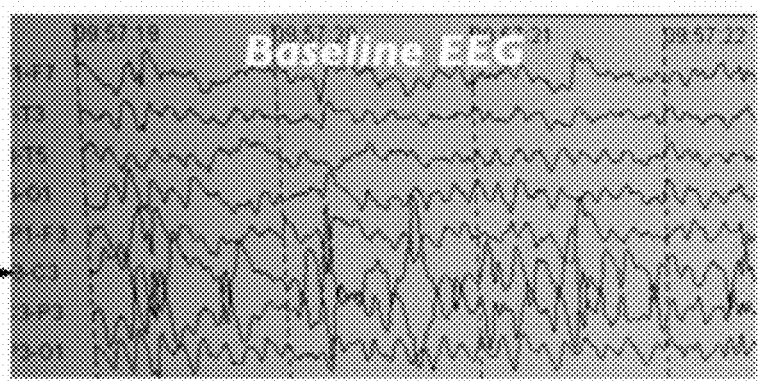
FIG. 9 is a pretreatment EEG of the patient of Example 16 showing left fronto-central seizure focus.

In Example 16, a 67 year old male patient presented with stroke and focal seizures. autism and generalized seizures. FIG. 9 is a baseline EEG taken at the initial examination, showing left fronto-central seizure focus.

Figure 10:
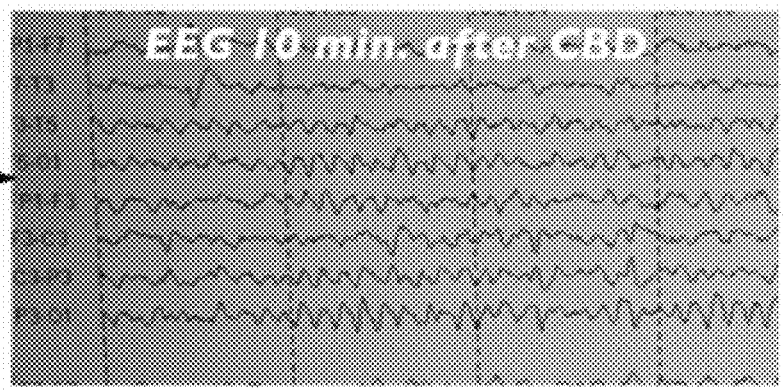
FIG. 10 is a post-treatment EEG of the patient of Example 16 showing attenuated seizure focus.

The patient was treated with 1 g of 1.6% CBD cream to the nuchal (back of the neck). An EEG was re-taken 10 minutes after application of the CBD dose, and showed attenuated seizure focus (FIG. 10). The patient remains seizure free about 9 months after initiation of twice a day CBD treatment to the nuchal region, which is also helping his spastic weakness from the stroke. He was able to return to work as a beterinarian and do surgery, which was unexpected as his Rehab MD had previously advised him that we would have to retire.

Example 17

Figure 11:
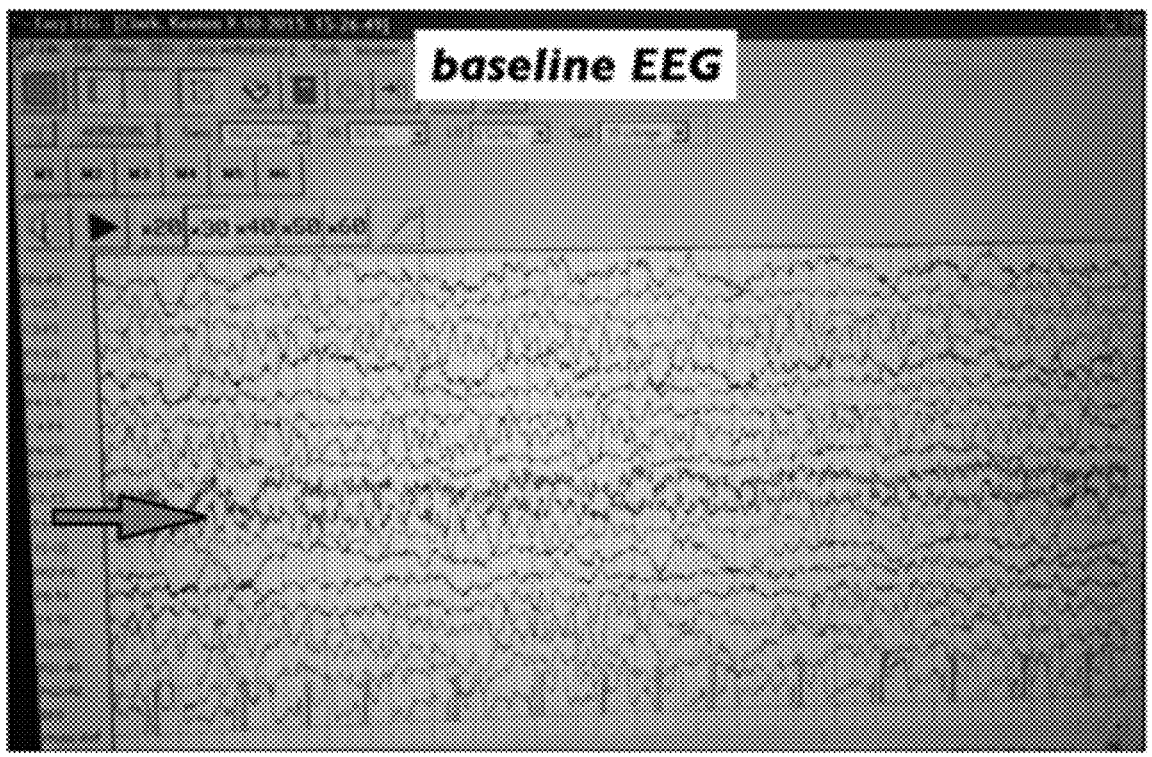
FIG. 11 is a pretreatment EEG of the patient of Example 17 showing cortical irritability on the left central region c/w potential for seizures.
Figure 12:
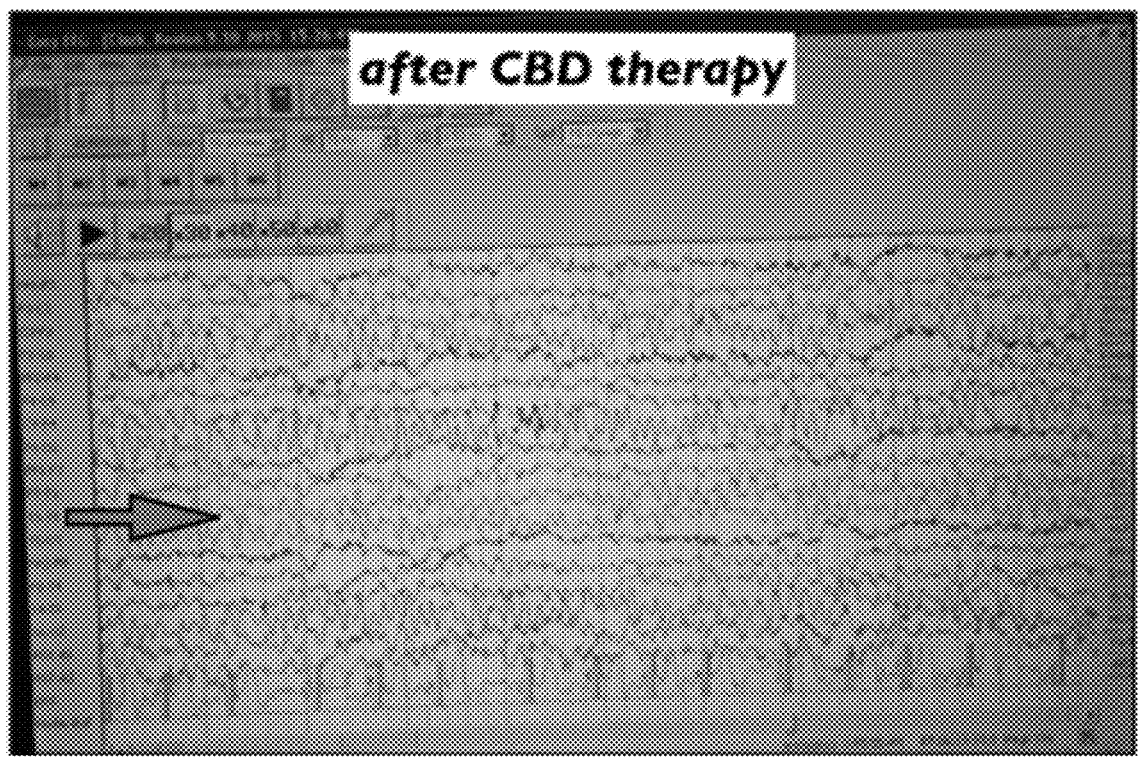
FIG. 12 is a post-treatment EEG of the patient of Example 17 showing attenuated seizure focus.

In Example 17, a 7 year old male patient presented with atonic seizures. The patient would suddenly freeze and fall down (e.g., riding a bike, at school, etc.). FIG. 11 is a baseline EEG taken at the initial examination, showing cortical irritability on the left central region c/w potential for seizures.

Figure 13:
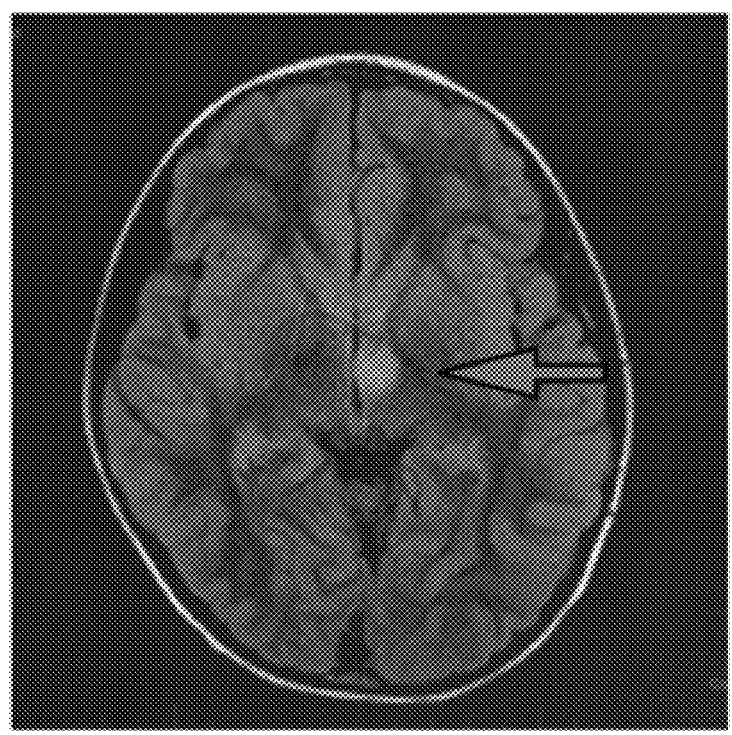
FIG. 13 is a post-treatment Brain MRI of the patient of Example 17 showing a left thalamic hamartoma.

The patient was treated with 1 g of 1.6% CBD cream to the nuchal (back of the neck). An EEG was re-taken 10 minutes after application of the CBD dose, and showed attenuated seizure focus. FIG. 13 is a brain MRI of the patient showing a left thalamic hamartoma, a benign developmental process, likely irritating the brain and causing his seizures. The patient has been seizure-free since initiating topical CBD therapy in the nuchal region in October 2015 and is only on CBD as a mediation for his seizures.

Example 18

In Example 18, 19 patients having a variety of conditions were treated with topical CBD as set forth in Table 7 below. The CBD was compounded in crystalline powder form rather than in CBD-oil form into the topical cream. The doses were 7.5 mg (0.75% topical CBD cream), 10 mg (1% topical CBD cream), 15 mg (1.5% topical CBD cream) or 20 mg (2% topical CBD cream).

TABLE 7

| Patient/Condition | Results |
| --- | --- |
| 1. 65 y/o male with chronic neck, back, and leg pain on narcotics. | After one application of 1% CBD to neck and back, pain in previous areas decreased additional 30% from prior baseline. |
| 2. 62 y/o female with anxiety and mood disorder. | After application of 1% CBD to back of neck, visibly improved mood and less anxiety. Became "giggly." |
| 3. 78 y/o male with lumbar degenerative disc disease with left leg weakness | After application of 1% CBD to lower back, improved strength of left leg and resolved back pain. |
| 4. 28 y/o female with post-concussive syndrome, with lethargy, cognitive dysfunction and abnormal EEG. | 1% CBD application to back of neck improved EEG disorganization and patient became more alert and spontaneous. |
| 5. 55 y/o male s/p remote stroke with spastic right hemiparesis and expressive aphasia. | Within several minutes of 1% topical CBD application to back of neck and right forearm, spasticity improved with better movement of affected extremity. |

TABLE 7-continued

| Patient/Condition | Results |
|---|---|
| 6. 24 y/o female with neck and back pain. | Pain and pressure went down 50% within 1 minute of applying 1% topical CBD to neck and back. |
| 7. 61 y/o female with long history of neck and back pain, headaches on narcotics and using 3% oil-based CBD topical cream. | 1% CBD application to back of neck improved pain within three minutes. Stated worked better than oil-based CBD she had been using. |
| 8. 29 y/o male with anxiety and left shoulder pain, smokes marijuana daily for relief of symptoms. | 1% topical CBD to neck and left shoulder reduced anxiety and decreased shoulder pain 20% within a few minutes. |
| 9. 81 y/o female with cognitive dysfunction and back pain. | Applied 0.75% topical CBD to neck and 1% to back with patient feeling more alert and responsive, back pain diminished. |
| 10. 20 y/o male with frontal head injury, agitation, and hallucinations of oil-based CBD topical cream, Lamictal. | 1.5% powdered topical CBD cream had more pronounced effect on anxiety and agitation. |
| 11. 24 y/o female s/p auto accident with neck tension and pain, | 1.5% topical CBD reduced neck tension and pain, improved range of motion. |
| 12. 72 y/o female with severe back and lower extremity neuropathic pain, | 2% topical CBD cream to lower back relieved back and lower extremity neuropathic pain. |
| 13. 80 y/o female with Parkinson's disease and tremors of head and left upper extremity. | 1% topical CBD applied to back of neck resulted in less anxiety, reduced tremors and improved gait with arm swing. |
| 14. 87 y/o female with cervical spondylosis, tremors of left hand. | topical CBD 1% to back of neck improved range of motion and reduced tremors. |
| 15. 56 y/o male s/p head injury with cognitive problems, focus issues, mood swings. | 1% topical CBD to neck resulted in improved focus, clearer thinking, and reduced anxiety. |
| 16. 84 y/o female with multi-infarct state, dementia, and agitation with anxiety. | 1% topical CBD cream to back of neck improved agitation and patient became more cooperative. |
| 17. 42 y/o female with neck tension, pain, and headaches. | 2% topical CBD cream to back of neck relieved neck pain and tension from 8 of 10 to 2 in few minutes. |
| 18. 58 y/o female s/p numerous facial plastic surgeries with neuropathic pain over left eye brow. | 1.5% topical CBD cream to the left eye brow and back of neck reduced anxiety and relieved neuropathic pain. Had been using oil based CBD cream. |
| 19. 67 y/o female with strokes, s/p concussion, with anxiety and cognitive problems. | Had been using 3% topical oil-based CBD cream. 1.5% powdered CBD cream further relieved anxiety and improved demeanor. |

Example 19

Several combinations of CBD and traditional compounds were formulated for topical therapy. These combinations are outlined below using either 2% or 3% CBD, made with 99.5% pure hemp-derived CBD.

The formula for 60 gram batch of 3% CBDerm is: CBD crystals 1.8 grams, Glycerine 3 ml, Liposomal base QS 60 grams. The formula for 60 gram batch of 2% CBDerm is: CBD crystals 1.2 grams, Glycerine 3 ml, Liposomal base QS 60 grams.

The above 2% and 3% CBD products are combined with traditionally used pharmaceutical compounds to produce the following:
  2% CBD+5 mg melatonin for insomnia.
  2% CBD+Apomorphine 2 mg for Parkinson's disease, tremors, dystonia.
  2% CBD+10 mg phentermine for ADD/ADHD and Tourette's.
  2% CBD+25 mg milnacipran (Savella®) for anxiety & panic attacks, mood disorders.
  2% CBD+4-AP (4-amino pyridine) 5 mg for DPN & other peripheral neuropathic conditions.
  2% CBD+4-AP 5 mg+apomorphine 2 mg for spasticity and spasms.
  2% CBD+sumatriptan 25 mg+\−tizanidine 5 mg (optional active ingredient) for migraine, tension headache.

Results:
The following 14 examples demonstrate the enhanced therapeutic effect experienced when topical CBD is added to topical traditional pharmaceutical compounds, or vice versa.

68 y/o male with MS spasticity, weakness, and cognitive slowing on long-term topical 4-amino pyridine. When topical CBD added to 4-AP, reported thinking more clearly, more focused, improved fluidity of gait, and "overall feeling better."

94 y/o male with Parkinson's disease, peripheral neuropathy, and gait problems on topical apomorphine. When CBD added to regimen, walking improved and moving more smoothly.

78 y/o female with tremors and chronic headaches on topical apomorphine. With the addition of topical CBD to the topical drug regimen, tremors improved with improved handwriting; headaches also resolved.

69 y/o female with tremors and left arm weakness on topical apomorphine. Adding topical CBD to apomorphine cream improved left arm strength and alleviated tremors.

64 y/o female with MS and spasticity of 4-amino pyridine topical cream, experienced improved spasticity and gait with addition of topical CBD to 4-AP.

67 y/o female with MS and spasticity on 4-amino pyridine topical cream, walked more smoothly with combination with 3% CBD topical cream.

77 y/o male with diabetic neuropathy and pain on combination of 4-amino pyridine, methyl cobalamin, methyl folate, and 5-pyridoxal phosphate for some time, experienced 80% additional improvement in pain and neuropathic symptoms with adding 3% CBD to topical regimen.

69 y/o male with familial tremors stable on long term regimen of topical apomorphine, tremors improved slightly more with addition of topical CBD.

44 y/o female s/p cervical fusion and neck pain on narcotics long term, with CBD 3% and apomorphine combination, had improved range of motion of neck with additional reduction in pain.

78 y/o female with neck pain, with combination topical cream of 3% CBD and apomorphine, had improved neck movement with less spasm.

54 y/o female with thoracic disc protrusion and transverse myelitis, had improvement in lower extremity spasticity, sensory symptoms, and decreased thoracic pain after using CBD and 4-amino pyridine combination.

70 y/o male with head injury, PTSD, cervical fusion, and gait disorder, had been on 3% CBD cream for number of months. With addition of apomorphine to the topical formula, he had improved sense of well-being, improved gait, and decreased neck pain and headache. He will be using the combination topical cream on a regular basis twice daily to the back of neck, "BON."

79 y/o female s/p strokes with dementia, failed back syndrome, and gait disturbance, had been using topical CBD for pain applied to neck and back. With 4-amino pyridine added to added to topical preparation, the patient experienced more alertness, spontaneity, and improved gait. She is now using the combination CBD and 4-AP topical cream going forward.

50 y/o female with ADHD, impulsivity, chronic migraines, experienced significantly improved ability to focus and being more calm and relaxed with combination topical cream of CBD and phentermine.

In view of positive results noted with topical combinations of the cannabinoid CBD with other traditional neuroactive compounds, various combinations were made available to patients for their medical conditions. The following chronic use combinations have been used in accordance with the present invention, administered topically at the back of the neck:

3% CBD and 5 mg melatonin for insomnia: 11 patients;
3% CBD and 2 mg apomorphine for spasticity, muscle spasm, tremor and Parkinson's disease: 2 patients;
3% CBD and 5 mg 4-aminopyridine for stroke, MS, demyelinating disorders, and peripheral neuropathy: 13 patients;
3% CBD and 25 mg sumatriptan for migraine attacks: 1 patient;
3% CBD and 25 mg minacipran for seizures with aniety and panic attacks: 2 patients; and
3% CBD and 10 mg phentermine for ADD/ADHD: 2 patients.

From the foregoing, it is apparent a synergistic therapeutic process occurs when a cannabinoid, such as CBD, is combined to a traditional pharmaceutical agent and the topical combination used to treat a medical condition. Whether this occurs only with the method of the present invention because of its unique nature of action through cell surface receptors on cutaneous free nerve-endings is not known at this time. With systemic drug deliveries, widespread dispersion and activation of drugs through the blood may not be conducive to a synergistic effect. On the contrary, systemic drug-drug interactions and side effects may occur.

At this point, it is unclear whether observed enhanced therapeutic efficacy is on the basis of cannabinoids enhancing specific functions of traditional compounds, such as neurotransmitter release and binding; the result of extraneous actions attributable only to cannabinoids; or, a combination of both processes. In light of the fact that cannabinoids exert many other therapeutic influences than influencing neurotransmitter release and binding, it is likely that the explanation will be it is a combined effect. It is clear, however, that the method described herein of topical administration of a Cannabinoid(s) along with a second therapeutically active agent provides an additional powerful treatment option for several difficult neurological and neuropsychiatric conditions. It should also be noted this enhancement of therapeutic benefits through combining of a traditional pharmacologic agent with CBD (or other cannabinoid) is different from "Entourage Effect," which is combining various ratios of different cannabinoids (for example, CBD-THC combinations) to achieve different effects.

CONCLUSION

The examples provided above are not meant to be exclusive. Many other variations of the present invention would be obvious to those skilled in the art, and are contemplated to be within the scope of the appended claims.

The active agents may be incorporated into the topical formulations in therapeutically equivalent amounts. The actual dose of an active agent (relative potency) may be determined based on a comparative dose to a therapeutically effective dose of an active agent described herein. However, it is noted that the differences in oral doses may not directly correspond to the differences in doses that are therapeutically effective via transdermal delivery of the serotonin agonist. Factors such as metabolism of the serotonin agonist, the ability of the drug to pass through the skin, among others, may affect the amount of serotonin agonist necessary to provide a therapeutic effect. One skilled in the art would readily understand this and adjust for the same.

The hypotheses of the inventor provided throughout the specification are for possible explanation purposes only, and are not meant to be limiting in any way.

The invention claimed is:

1. A method of treating a disease state or condition in human, comprising topically applying onto the surface of the skin in an area extending from behind one ear to the other ear of the mammal and below the hairline at the back of the neck of a human patient administering a unit dose of a cannabinoid drug(s) and a second therapeutically active drug in therapeutically effective amounts formulated in a mousse, cream, gel or ointment that allows for the drug to be immediately absorbable and available for the free nerve endings of the trigeminal nervous system which reside under the skin surface to treat the disease state or condition, to provide regional neuro-affective therapy to the human patient.

2. The method of claim 1, wherein the cannabinoid drug(s) and the second therapeutically active drug are administered such that they are absorbed in an area of the skin where the afferent components of trigeminal nerve system, cervical sympathetic nerves, and vagus nerve are located.

3. The method of claim 1, wherein the cannabinoid drug(s) comprise a mixture of pharmaceutically acceptable cannabinoids, such that the mixture provides substantially no psychoactive effect or no psychoactive effect.

4. The method of claim 1, wherein the cannabinoid drug(s) comprises at least about 80% cannabidiol.

5. The method of claim 1, wherein the topical pharmaceutical formulation comprises a pharmaceutically acceptable aqueous based carrier.

6. The method of claim 5, wherein the cannabinoid drug(s) in the pharmaceutical formulation comprises at least about 80% cannabidiol.

7. The method of claim 1, wherein the condition is diabetic peripheral neuropathy and the second therapeutically active drug is 4-aminopyridine.

8. The method of claim 1, wherein the condition is selected from the group consisting of benign essential/familial tremor, tremor related to MS, chronic encepahalopathies, congenital CNS degeneration conditions/cerebral palsy, cerebellar degeneration syndromes, and spasticity conditions, and a peripheral neuropathic condition and the second therapeutically active drug is 4-aminopyridine.

9. The method of claim 1, wherein the condition is spasticity and/or spasms and the second therapeutically active drug is 4-aminopyridine.

10. The method of claim 1, further comprising a third therapeutically active drug which is a skeletal muscle relaxant.

11. The method of claim 10, wherein the skeletal muscle relaxant is tizanidine.

12. The method of claim 1, wherein the cannabinoid drug(s) comprises cannabidiol.

13. The method of claim 6, wherein the aqueous based pharmaceutically acceptable carrier comprises ethoxydiglycol, water, glycerin, $C_{12-15}$ alkyl benzoate, glyceryl stearate, dimethicone, cetearyl alcohol, cetearyl glucoside, polyacrylamide, cetyl alcohol, magnesium aluminum silicate, xanthan gum, aloe vera (aloe barbadensis), tocopheryl acetate (vitamin E acetate), prunus amygdalus amara (bitter almond) kernel oil, *Vitis vinifera* (grape) seed extract, *Triticum vulgare* (wheat) germ oil, retinyl palmitate (vitamin A palmitate), ascorbyl palmitate (vitamin C palmitate), pro-lipo multi-emulsion liposomic system, tetrasodium EDTA, phenoxyethanol, and sodium hydroxymethylglycinate.

14. The method of claim 4, wherein cannabidiol is incorporated into the pharmaceutically acceptable carrier from a CBD-oil.

15. The method of claim 4, wherein cannabidiol incorporated into the pharmaceutically acceptable carrier is a purified crystalline CBD.

16. The method of claim 1, wherein the unit dose comprises from about 3 mg to about 50 mg cannabidiol.

17. The method of claim 4, wherein the unit dose comprises from about 3 mg to about 50 mg cannabidiol.

18. The method of claim 7, wherein the unit doses comprises from about 1 mg to about 40 mg of 4-aminopyridine.

19. The method of claim 7, wherein the unit doses comprises from about 2 mg to about 10 mg 4-aminopyridine.

* * * * *